(12) United States Patent  
Iijima et al.

(10) Patent No.: US 7,998,956 B2  
(45) Date of Patent: Aug. 16, 2011

(54) BENZOXAZINES AND RELATED NITROGEN-CONTAINING HETEROBICYCLIC COMPOUNDS USEFUL AS MINERALOCORTICOID RECEPTOR MODULATING AGENTS

(75) Inventors: Toru Iijima, Osaka (JP); Yasuo Yamamoto, Osaka (JP); Hidenori Akatsuka, Osaka (JP); Takayuki Kawaguchi, Osaka (JP)

(73) Assignee: Mitsubishi Tanabe Pharma Corporation, Osaka (JP)

( * ) Notice: Subject to any disclaimer, the term of this patent is extended or adjusted under 35 U.S.C. 154(b) by 387 days.

(21) Appl. No.: 12/162,779

(22) PCT Filed: Feb. 1, 2007

(86) PCT No.: PCT/JP2007/052165  
§ 371 (c)(1),  
(2), (4) Date: Jul. 30, 2008

(87) PCT Pub. No.: WO2007/089034  
PCT Pub. Date: Aug. 9, 2007

(65) Prior Publication Data  
US 2009/0023716 A1    Jan. 22, 2009

(30) Foreign Application Priority Data

Feb. 2, 2006  (JP) ................. 2006-025403  
Oct. 10, 2006  (JP) ................. 2006-275917

(51) Int. Cl.  
C07D 265/36   (2006.01)  
C07D 413/04   (2006.01)  
A61K 31/538   (2006.01)  
A61K 31/5415  (2006.01)

(52) U.S. Cl. .................... 514/230.5; 544/105  
(58) Field of Classification Search .............. 544/105; 514/230.5  
See application file for complete search history.

(56) References Cited

U.S. PATENT DOCUMENTS 5,420,126 A   5/1995  Matsumoto et al.  
6,300,342 B1  10/2001  Heckel et al.

FOREIGN PATENT DOCUMENTS

CN  1051910 A   6/1991  
DE  197 27 117 A1  1/1999  
EP  0 432 893 A2  6/1991  
WO  WO-97/17333 A1  5/1997  
WO  WO-99/00371 A1  1/1999  
WO  WO-01/57003 A1  8/2001  
WO  WO-2004/067529 A1  8/2004  
WO  WO-2006/077821 A1  7/2006

OTHER PUBLICATIONS

Hogale et al. Journal of the Indian Chemical Society (1985), 62(6), 471-2.*  
STN International Search Results dated Aug. 24, 2010.  
Asinex Platinum Collection, Chemicals Accession No. 846556-34-1; Chemical Name: N-(4-benzyl-3-oxo-3,4-dihydro-2H-benzo[1,4]oxazin-7-yl)-4-methyl-benzenesulfonamide; Mar. 22, 2005.  
Asinex Platinum Collection, Chemicals Accession No. 846556-41-0; Chemical Name: N-[4-[[[4-(2-fluorobenzyl)-3-oxo-3,4-dihydro-2H-benzo[1,4]oxazin-7-yl]amino]sulfonyl]-phenyl]acetamide; Feb. 21, 2005.  
Asinex Platinum Collection, Chemicals Accession No. 846556-44-3; Chemical Name: N-[4-[[[4-(4-fluorobenzyl)-3-oxo-3,4-dihydro-2H-benzo[1,4]oxazin-7-yl]amino]sulfonyl]phenyl]acetamide; Feb. 21, 2005.

* cited by examiner

*Primary Examiner* — Kahsay T Habte  
(74) *Attorney, Agent, or Firm* — Birch, Stewart, Kolasch & Birch, LLP

(57) ABSTRACT

The present invention relates to a compound, useful as a mineralocorticoid receptor-modulating agent, of the following formula [I]:

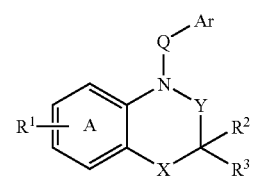

[I]

wherein Ring A is a benzene ring optionally having a substituent(s) other than $R^1$ etc, $R^1$ is a group of the formula: $R^aSO_2NH$— etc, $R^a$ is an alkyl group etc, $R^2$ and $R^3$ are each a hydrogen atom, a phenyl group, an optionally substituted alkyl group etc, X is an oxygen atom etc, Y is a group of the formula: —C(=O)— etc, Ar is an optionally substituted aryl group or an optionally substituted heteroaryl group, Q is a single bond, an alkylene group etc, or a pharmaceutically acceptable salt thereof.

22 Claims, No Drawings

BENZOXAZINES AND RELATED NITROGEN-CONTAINING HETEROBICYCLIC COMPOUNDS USEFUL AS MINERALOCORTICOID RECEPTOR MODULATING AGENTS

TECHNICAL FIELD

The present invention relates to nitrogen-containing heterobicyclic compounds having an affinity to mineralocorticoid receptor (MR) and useful for prevention or treatment of various diseases or disease states associated with such receptor, and a MR-modulating agent comprising such a compound.

BACKGROUND ART

A physiologically active low-molecular weight hydrophobic substance such as a steroid hormone shows its activities as a ligand through its specific nuclear receptor. The nuclear steroid hormone receptors constitute a gene superfamily and the receptors work as a ligand-dependent transcription factor and hence regulate (activate or inhibit) the expression of the target genes at the level of transcription. Such receptors include mineralocorticoid receptor (MR), glucocorticoid receptor (GR), androgen receptor (AR), estrogen receptor (ER) and progesterone receptor (PR). The ligand of said steroid hormone receptors, e.g., a mineralocorticoid (aldosterone) or a glucocorticoid (cortisol and the like) exhibits various physiological activities via respective receptor (Journal of Endocrinology, 2001; 169: p. 437-445).

MR-specific ligand, aldosterone, is one of mediators in renin-angiotensin-aldosterone system (RAAS). Formerly, aldosterone has been considered to be nothing but a hormone which is produced only in adrenal glands and acts on distal urinary tubule to regulate water and sodium metabolism. However, recent studies proved that aldosterone is produced in various tissues such as heart, blood vessels, brain and the like and its receptors are widely distributed in cardiovascular tissues and the like. Besides, aldosterone is not only a risk hormone showing various impeding effects (e.g., cardiac fibrosis/necrosis, potentiation of catecholamine activity, deterioration of baroreceptor response). In the recent large scale clinical trials (RALES and EPHESUS), it was confirmed that the concomitant use of an aldosterone receptor antagonist (eplerenone or spironolactone) with a conventional medicament such as an ACE inhibitor and the like significantly reduced hospitalization and mortality rate in patients with severe heart failure and significantly ameliorate the prognosis of patients with acute cardiac infarction (New England Journal of Medicine, 2003; 341: p. 709-717, New England Journal of Medicine, 2003; 348: p. 1309-1321). In this regard, it is considered that effective blockade of such hormone is important to establish the therapy of the cardiovascular diseases associated with aldosterone and its receptors.

As mentioned above, any ligands having an affinity to MR and activity of modulating the receptor function, namely repressors, antagonists, agonists, partial antagonists or partial agonists, may be useful as medicaments for prevention or treatment of the diseases or disease states associated with aldosterone. On the other hand, a steroidal MR-ligand such as spironolactone or eplerenone has been often associated with specific and serious side effects (e.g., gynecomastia, irregular menses, erectile dysfunction), and therefore it has been desired to develop a compound having safety as a medicament without such side effects.

Up to now, 6H-dibenzo[b,e]oxepine derivatives (WO2005/066161), dihydro-pyridine derivatives (WO2005/097118), dibenzo[b,d]pyrane derivatives (Bioorganic and Medicinal Chemistry Letters, 2004; 14: p. 2079-2082) and the like have been known as a non-steroidal ligand having an affinity to MR. However, no benzoxazine-sulfonamide derivative having MR-modulating activity (e.g., MR-antagonizing activity) has been reported. On the other hand, some benzoxazine-sulfonamide derivatives have been disclosed in the following references (WO97/017333, EP432893A, WO2001/057003, WO99/000371).

DISCLOSURE OF INVENTION

The object of the present invention is to provide novel nitrogen-containing heterobicyclic compounds having a mineralocorticoid receptor-modulating activity and useful as a medicine.

The present invention relates to a novel nitrogen-containing heterobicyclic compound of the following formula [I]:

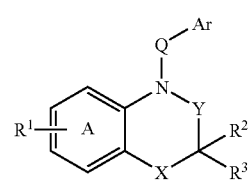

wherein Ring A is a benzene ring optionally having a substituent(s) other than $R^1$ or a nitrogen-containing 6-membered aromatic heterocyclic ring optionally having a substituent(s) other than $R^1$, $R^1$ is a group of the formula: $R^aSO_2NH$—, $R^aSO_2NH$—$CH_2$— or $(R^b)(R^c)NSO_2$—, $R^a$ is an alkyl group, a cycloalkyl group, an amino group optionally substituted by an alkyl group(s), an optionally substituted aryl group, or an optionally substituted heteroaryl group, $R^b$ and $R^c$ are the same or different and are each a hydrogen atom, an alkyl group or a cycloalkyl group, $R^2$ and $R^3$ are the same or different and are each a hydrogen atom, a halogen atom, an optionally substituted alkyl group, an alkenyl group, a carboxyl group, an alkoxycarbonyl group, an optionally substituted carbamoyl group or an optionally substituted aryl group, or both $R^2$ and $R^3$ combine each other together with the adjacent carbon atom to form a saturated or unsaturated cyclic group (said cyclic group optionally containing the same or different one or two heteroatom(s) selected from an oxygen atom, a sulfur atom and a nitrogen atom), X is an oxygen atom, a sulfur atom, a methylene group or a group of the formula: —$NR^4$—, $R^4$ is a hydrogen atom, an alkyl group, an optionally substituted aralkyl group or an acyl group, Y is a group of the formula: —C(=O)—, —C(=S)— or —CH($R^5$)—, $R^5$ is a hydrogen atom, an alkyl group or an optionally substituted aryl group, Ar is an optionally substituted aryl group or an optionally substituted heteroaryl group, and Q is a single bond, an alkylene group or an alkenylene group, or a pharmaceutically acceptable salt thereof, excluding N-(4-benzyl-3-oxo-3,4-dihydro-2H-1,4-benzoxazin-7-yl) (p-toluenesulfonamide);

N-[4-(2-fluorobenzyl)-3-oxo-3,4-dihydro-2H-1,4-benzoxazin-7-yl][4-(N-acetylamino)benzenesulfonamide];

N-[4-(4-fluorobenzyl)-3-oxo-3,4-dihydro-2H-1,4-benzoxazin-7-yl][4-(N-acetylamino)benzenesulfonamide];

N-[4-(7-amidinonaphthalen-2-yl)methyl-3-oxo-3,4-dihydro-2H-1,4-benzoxazin-7-yl]benzenesulfonamide;

N-[4-(7-amidinonaphthalen-2-yl)methyl-3-oxo-3,4-dihydro-2H-1,4-benzoxazin-7-yl](p-methoxyphenylsulfonamide);

N-[4-(7-amidinonaphthalen-2-yl)methyl-3-oxo-3,4-dihydro-2H-1,4-benzoxazin-7-yl](6-bromonaphthalene-2-yl)sulfonamide;

N-[4-(7-amidinonaphthalen-2-yl)methyl-3-oxo-3,4-dihydro-2H-1,4-benzoxazin-7-yl](5-quinolylsulfonamide); and N-[2,2-dimethyl-4-(1-oxidopyridin-2-yl)-3,4-dihydro-2H-1,4-benzoxazin-6-yl]-methanesulfonamide, or relates to a pharmaceutical composition comprising as an active ingredient the compound [I] mentioned above or a pharmaceutically acceptable salt thereof.

Besides, the present invention relates to a mineralocorticoid receptor-modulating agent comprising a compound of the following formula [I]:

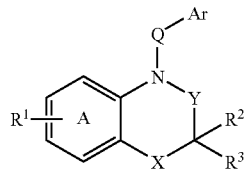

wherein the symbols are the same as defined above or a pharmaceutically acceptable salt thereof.

Furthermore, the present invention relates to a pharmaceutical composition comprising as an active ingredient a compound of the following formula [I-a]:

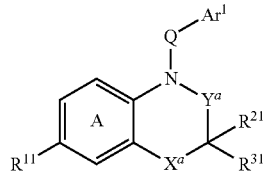

wherein Ring A is a benzene ring optionally having a substituent(s) other than $R^{11}$ or a nitrogen-containing 6-membered aromatic heterocyclic ring optionally having a substituent(s) other than $R^{11}$, $R^{11}$ is a group of the formula: $R^{aa}SO_2NH—$, $R^{aa}SO_2NH—CH_2—$ or $(R^b)(R^c)NSO_2—$, $R^{aa}$ is an alkyl group, a cycloalkyl group, an amino group optionally substituted by one or two alkyl group(s), a phenyl group or a 5- or 6-membered monocyclic heteroaryl group, $R^b$ and $R^c$ are the same or different and are each a hydrogen atom, an alkyl group or a cycloalkyl group, one of $R^{21}$ and $R^{31}$ is a hydrogen atom, a halogen atom or an alkyl group, and another is a hydrogen atom, an alkyl group, an alkoxycarbonyl group, a phenyl group or a halogenophenyl group, or $R^{21}$ and $R^{31}$ combine each other together with the adjacent carbon atom to form a saturated or unsaturated cyclic group (said cyclic group optionally containing the same or different one or two heteroatom(s) selected from an oxygen atom, a sulfur atom and a nitrogen atom), $X^a$ is an oxygen atom, a sulfur atom, a methylene group or a group of the formula: $—NH—$, $Y^a$ is a group of the formula: $—C(=O)—$, $—C(=S)—$ or $—CH(R^{51})—$, $R^{51}$ is a hydrogen atom or a phenyl group, $Ar^1$ is (a) a phenyl (or naphthyl) group optionally substituted by one to three group(s) selected from a halogen atom, a hydroxyl group, a cyano group, a nitro group, an allyl group optionally substituted by one to three halogen atom(s), a hydroxyalkyl group, an acyloxyalkyl group, an alkoxy group optionally substituted by one to three halogen atom(s), an alkoxycarbonylalkoxy group, an alkylthio group, an alkylenedioxy group optionally substituted by one to two halogen atom(s), an amino group optionally substituted by one or two alkyl group(s), an acylamino group, a cycloalkyl group and an alkylsulfonyl group;

(b) a thienyl group optionally substituted by one to two group(s) selected from a halogen atom and a trihalogenoalkyl group, said thienyl group being optionally fused to a benzene ring;

(c) a pyridyl group optionally substituted by one to two group(s) selected from a halogen atom, a nitro group, an alkyl group and a trihalogenoalkyl group;

(d) a pyrimidinyl group optionally substituted by a halogen atom;

(e) a quinolyl group;

(f) a pyridazinyl group optionally substituted by a halogen atom;

(g) a pyrrolyl group;

(h) a furyl group optionally fused to a benzene ring;

(i) a thiazolyl group optionally fused to a benzene ring; or (j) an imidazolyl group optionally fused to a benzene ring and optionally substituted by an alkyl group, and Q is a single bond, an alkylene group or an alkenylene group, or a pharmaceutically acceptable salt thereof.

BEST MODE TO CARRY OUT INVENTION

In the compound of the present invention [I]/[I-a], when the Ring A is a nitrogen-containing 6-membered aromatic heterocyclic ring, such heterocyclic ring includes a 6-membered aromatic heterocyclic ring containing one or two nitrogen atom(s) such as a pyridine ring, a pyrazine ring, a pyrimidine ring, a pyridazine ring and the like. Among them, a pyridine ring is preferable.

The Ring A may be substituted by the same or different and one to three group(s), other than $R^1$, and examples of such substituent(s) include a group(s) selected from (a) a halogen atom, (b) an alkyl group (said alkyl group being optionally substituted by one to three group(s) selected from a halogen atom, a hydroxyl group, an alkoxy group, an amino group, a monoalkylamino group and a dialkylamino group), (c) a hydroxyl group, (d) an alkoxy group, (e) an amino group (said amino group being optionally substituted by one or two group(s) selected from an alkyl group and an acyl group), (f) a cyano group, (g) a carboxyl group, (h) an alkoxycarbonyl group, (i) an alkenyl group optionally substituted by an alkoxy group, (j) an alkanoyl group, (k) a cycloalkyl group and (l) a carbamoyl group (said carbamoyl group being optionally substituted by one or two alkyl group(s)).

In case that the above substituent in Ring A contains an acyl group (e.g., an acylamino group), examples of said acyl group include a group of the formula: $R^x$—CO— formed by removing a hydroxyl group from a carboxyl group in a carboxylic acid compound of the following formula:

$$R^x\text{—COOH}$$

in which $R^x$ is an alkyl group, an alkyloxy group, an aryl group or an aralkyloxy group. Said acyl group may be an alkanoyl group such as a formyl group, an acetyl group, a propionyl group, a pivaloyl group and the like, an alkoxycarbonyl group such as a methoxycarbonyl group, an ethoxycarbonyl group, a tert-butoxycarbonyl group and the like, an arylcarbonyl group such as a benzoyl group and an aralkyloxycarbonyl group such as a benzyloxycarbonyl group and the like.

In case that $R^a$ or Ar in the compound [I] is an aryl (or heteroaryl) group, examples of such aryl (or heteroaryl) group include a 5- to 10-membered mono- or bicyclic aryl (or heteroaryl) group such as a phenyl group, a naphthyl group, a thienyl group, a pyrrolyl group, a furyl group, a thiazolyl group, an oxazolyl group, an imidazolyl group, a pyrazolyl group, a pyridyl group, a pyridazinyl group, a pyrimidinyl group, a pyrazinyl group, a benzofuranyl group, a benzoxazolyl group, a benzothienyl group, a benzothiazolyl group, a benzimidazolyl group, a quinolyl group, an isoquinolyl group and the like. Among them, preferable examples may be a 6- to 10-membered monocyclic or bicyclic aryl group such as a phenyl group or a naphthyl group or a 5- to 10-membered monocyclic or bicyclic heteroaryl group containing one to two heteroatom(s) selected from an oxygen atom, a sulfur atom and a nitrogen atom, and particularly preferred examples include a phenyl group, a thienyl group, a pyrrolyl group, a pyridyl group, a pyrimidinyl group, a pyridazinyl group, a benzothienyl group and a benzofuranyl group.

Said aryl (or heteroaryl) group in $R^a$ or Ar may be substituted by one to three group(s) selected from (a) a halogen atom (e.g., fluorine atom, chlorine atom, bromine atom, iodine atom), (b) a hydroxyl group, (c) an alkyl group optionally substituted by one to three halogen atom(s) (e.g., methyl group, ethyl group, propyl group, tert-butyl group, trifluoromethyl group, difluoromethyl group and the like), (d) a hydroxyalkyl group (e.g., a hydroxymethyl group, a hydroxyethyl group), (e) an acyloxyalkyl group (e.g., a benzoyloxymethyl group), (f) an alkoxy group optionally substituted by one to three halogen atom(s) (e.g., a methoxy group, an ethoxy group, a propoxy group, a tert-butoxy group, a trifluoromethoxy group), (g) an alkoxycarbonylalkoxy group (e.g., a tert-butoxycarbonylmethoxy group), (h) an alkylthio group (e.g., methylthio group, ethylthio group), (i) an alkylenedioxy group optionally substituted by one to two halogen atom(s) (e.g., a methylenedioxy group, an ethylenedioxy group, a difluoromethylenedioxy group), (j) an amino group optionally substituted by one to two alkyl group(s) (e.g., an amino group, a dimethylamino group), (k) an acylamino group (e.g., an alkanoylamino group such as an acetylamino group), (l) a cycloalkyl group (e.g., a cyclopropyl group, a cyclopentyl group) and (m) an alkylsulfonyl group (e.g., a methylsulfonyl group, an ethylsulfonyl group). Examples of the protecting group of said amino group include an alkoxycarbonyl group such as methoxycarbonyl group, ethoxycarbonyl group, tert-butoxycarbonyl group and the like and an aralkyloxycarbonyl group such as benzyloxycarbonyl group and the like. Examples of the acyl group mentioned above include a group of the formula: $R^x$—CO— and among them, preferable example may be an alkanoyl group such as an acetyl group, an arylcarbonyl group such as a benzoyl group and the like.

In case that $R^2$ and $R^3$ in the compound [I] are an aryl group, examples of such aryl group include a 6- to 10-membered mono- or bicyclic aryl group such as a phenyl group, a naphthyl group and the like. Among them, a phenyl group is preferable. Said aryl group may be substituted by one or two halogen atom(s) (e.g., fluorine atom, chlorine atom, bromine atom or iodine atom).

In case that $R^2$ and $R^3$ in the compound [I] combine each other together with the adjacent carbon atom to form a saturated or unsaturated cyclic group, examples of such cyclic group include a saturated or unsaturated, $C_{3-8}$ monocyclic group such as (a) a cycloalkyl group (e.g., cyclopropyl group, cyclobutyl group, cyclopentyl group, cyclohexyl group and the like), (b) a cycloalkenyl group (e.g., cyclopropenyl group, cyclobutenyl group, cyclopentenyl group and the like) or (c) a saturated or unsaturated 5- or 8-membered, nitrogen-, oxygen- or sulfur-containing heteromono- or heterobicyclic group. Among them, a $C_{3-8}$ cycloalkyl group is preferable.

In case that $R^4$ in the compound [I] is an aralkyl group, such aralkyl group may be a mono- or bicyclic $C_{6-10}$ aryl-$C_{1-6}$ alkyl group such as a benzyl group, a phenethyl group, a 3-phenylpropyl group, a (1-naphthyl)methyl group, a 2-(1-naphthyl)ethyl group and the like. Among them, a benzyl group is preferable. The aryl moiety in said aralkyl group may be substituted by a halogen atom and the like.

The acyl group in $R^4$ may be a group of the formula: $R^x$—CO— including an alkanoyl group such as acetyl group, propionyl group, pivaloyl group and the like, an alkoxycarbonyl group such as methoxycarbonyl group, ethoxycarbonyl group, tert-butoxycarbonyl group and the like, and an aralkyloxycarbonyl group such as benzyloxycarbonyl group and the like.

Examples of the aryl group in $R^5$ include a 6- to 10-membered monocyclic or bicyclic aryl group such as a phenyl group, a naphthyl group and the like. Among them, a phenyl group is preferable. Said aryl group may be substituted by one or two halogen atom(s).

Among the compounds [I] of the present invention, preferred examples include a compound in which X is oxygen atom, a sulfur atom, a methylene group or a group of the formula: —NH—.

Among the compounds mentioned above, more preferred compound may be a compound of the following formula [I-a]:

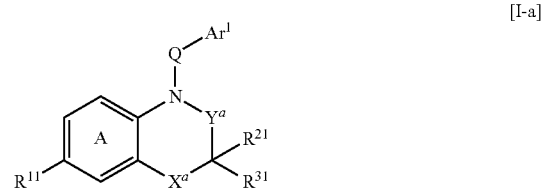

[I-a]

wherein the symbols are the same as defined above or a pharmaceutically acceptable salt thereof.

Further preferred examples include a compound [I-a] in which Ring A is a benzene ring optionally substituted by a group, other than $R^{11}$, selected from a halogen atom, a hydroxyl group, a $C_{1-4}$ alkyl group, a trihalogeno-$C_{1-4}$ alkyl group, a hydroxy-$C_{1-4}$ alkyl group, a $C_{1-4}$ alkoxy-$C_{1-4}$ aryl group, a $C_{1-4}$ alkoxy group, an amino group, a $C_{2-4}$ alkenyl group, a $C_{2-5}$ alkanoyl group and a $C_{3-8}$ cycloalkyl group, $R^{11}$ is a $C_{1-4}$ alkylsulfonylamino group, a $C_{3-6}$ cycloalkylsulfonylamino group, a $C_{1-4}$ alkylaminosulfonyl group, a $C_{1-4}$ alkylsulfonylamino-methyl group, an aminosulfonylamino group, a di($C_{1-4}$ alkyl)amino-sulfonylamino group or a mono ($C_{1-4}$ alkyl)amino-sulfonyl group, one of $R^{21}$ and $R^{31}$ is a hydrogen atom or a $C_{1-4}$ alkyl group and another is a hydrogen atom, a halogen atom, a $C_{1-4}$ alkyl group or a phenyl group or both of them combine each other to form a $C_{3-8}$ cycloalkyl group, $X^a$ is an oxygen atom, a sulfur atom, a methylene group or a group of the formula: —NH—, $Ar^1$ is (a) a phenyl group optionally substituted by one to three group(s) selected from a halogen atom, a hydroxyl group, a cyano group, a nitro group, a $C_{1-4}$ alkyl group, a $C_{1-4}$ alkyl group substituted by one to three halogen atom(s), a hydroxy-$C_{1-4}$ alkyl group, an acyloxy-$C_{1-4}$ alkyl group, a $C_{1-4}$ alkoxy group, a $C_{1-4}$ alkoxy group substituted by one to three halogen atom(s), a $C_{3-8}$ cycloalkyl group, a $C_{1-4}$ alkylthio group, an amino group optionally substituted by one or two $C_{1-4}$ alkyl group(s), a $C_{2-5}$ alkanoylamino group, a $C_{1-4}$ alkylenedioxy group and a $C_{1-4}$ alkylenedioxy group substituted by one or two halogen atom(s); (b) a naphthyl group; (c) a thienyl (or benzothienyl) group optionally substituted by one to two group(s) selected from a halogen atom and a trihalogeno-$C_{1-4}$ alkyl group; (d) a pyridyl group optionally substituted by one to two group(s) selected from a halogen atom, a nitro group, a $C_{1-4}$ alkyl group and a trihalogeno-$C_{1-4}$ alkyl group; or (e) a benzofuranyl group, and Q is a single bond or a $C_{1-4}$ alkylene group and $Y^a$ is a group of the formula: —C(=O)—, —C(=S)— or —CH$_2$—.

Among the above-mentioned compounds, examples of particularly preferred compound [I-a] include those in which:
(1) both of $R^{21}$ and $R^{31}$ are a hydrogen atom;
(2) $R^{21}$ is a hydrogen atom and $R^{31}$ is a $C_{1-4}$ alkyl group;
(3) $R^{21}$ is a hydrogen atom or a $C_{1-4}$ alkyl group and $R^{31}$ is a phenyl group;
(4) both of $R^{21}$ and $R^{31}$ are a $C_{1-4}$ alkyl group;
(5) $R^{21}$ is a hydrogen atom and $R^{31}$ is a halogen atom; or
(6) $R^{21}$ and $R^{31}$ combine together with the adjacent carbon atom to form a $C_{3-8}$ cycloalkyl group.

The above-mentioned particularly preferred compound include a compound selected from the group consisting of:
N-(3-oxo-2,4-diphenyl-3,4-dihydro-2H-1,4-benzoxazin-7-yl)methanesulfonamide;
N-[4-(4-fluorophenyl)-3-oxo-2-phenyl-3,4-dihydro-2H-1,4-benzoxazin -7-yl]methanesulfonamide;
N-[4-(4-chlorophenyl)-3-oxo-2-phenyl-3,4-dihydro-2H-1,4-benzoxazin-7-yl]methanesulfonamide;
N-(2,2-dimethyl-3-oxo-4-phenyl-3,4-dihydro-2H-1,4-benzoxazin-7-yl)methanesulfonamide;
N-[4-(4-fluorophenyl)-2,2-dimethyl-3-oxo-3,4-dihydro-2H-1,4-benzoxazin -7-yl]methanesulfonamide;
N-[4-(4-chlorophenyl)-2,2-dimethyl-3-oxo-3,4-dihydro-2H-1,4-benzoxazin -7-yl]methanesulfonamide;
N-[4-(3,4-difluorophenyl)-2,2-dimethyl-3-oxo-3,4-dihydro-2H-1,4-benzoxazin -7-yl]methanesulfonamide;
N-[4-(4-fluoro-3-methylphenyl)-2,2-dimethyl-3-oxo-3,4-dihydro-2H-1,4-benzoxazin-7-yl]methanesulfonamide;
N-[4-(3-chloro-4-fluorophenyl)-2,2-dimethyl-3-oxo-3,4-dihydro-2H-1,4-benzoxazin-7-yl]methanesulfonamide;
N-[4-(4-methoxyphenyl)-2,2-dimethyl-3-oxo-3,4-dihydro-2H-1,4-benzoxazin -7-yl]methanesulfonamide;
N-[4-(4-fluorophenyl)-2,2-dimethyl-3-oxo-3,4-dihydro-2H-1,4-benzoxazin -7-yl]ethanesulfonamide;
N-[4-(5-fluoropyridin-2-yl)-2,2-dimethyl-3-oxo-3,4-dihydro-2H-1,4-benzoxazin -7-yl]methanesulfonamide;
N-(4-benzyl-2,2-dimethyl-3-oxo-3,4-dihydro-2H-1,4-benzoxazin -7-yl)methanesulfonamide;
N-(4-benzyl-3-oxo-3,4-dihydro-2H-1,4-benzoxazin-7-yl) methanesulfonamide;
N-[4-(4-fluorophenyl)-2-methyl-3-oxo-3,4-dihydro-2H-1,4-benzoxazin -7-yl]methanesulfonamide;
4-(4-fluorophenyl)-N,2,2-trimethyl-3-oxo-3,4-dihydro-2H-1,4-benzoxazine -7-sulfonamide;
N-[4-(5-chloro-2-thienyl)-2,2-dimethyl-3-oxo-3,4-dihydro-2H-1,4-benzoxazin -7-yl]methanesulfonamide;
N'-[4-(4-fluorophenyl)-2,2-dimethyl-3-oxo-3,4-dihydro-2H-1,4-benzoxazin -7-yl]-N,N-dimethylsulfamide;
N-[4-(4-fluorophenyl)-2,2-dimethyl-3,4-dihydro-2H-1,4-benzoxazin -7-yl]methanesulfonamide;
N-[2,2-dimethyl-3-oxo-4-(3-thienyl)-3,4-dihydro-2H-1,4-benzoxazin -7-yl]methanesulfonamide;
N-[4-(4-fluorophenyl)-3-oxo-3,4-dihydrospiro[1,4-benzoxazine-2,1'-cyclobutan]-7-yl]methanesulfonamide;
N-[1-(4-fluorophenyl)-3,3-dimethyl-2-oxo-1,2,3,4-tetrahydroquinoxalin -6-yl]methanesulfonamide;
N-[4-(4-fluoro-3-trifluoromethyl)phenyl]-2,2-dimethyl-3-oxo-3,4-dihydro-2H -1,4-benzoxazin-7-yl]methanesulfonamide;
N-[2,2-dimethyl-4-(4-methylphenyl)-3-oxo-3,4-dihydro-2H-1,4-benzoxazin -7-yl]methanesulfonamide;
N-[4-(4-fluorophenyl)-3-oxo-3,4-dihydrospiro[1,4-benzoxazine-2,1'-cyclopropan]-7-yl]methanesulfonamide;
N-[2,2-diethyl-4-(4-fluorophenyl)-3-oxo-3,4-dihydro-2H-1,4-benzoxazin -7-yl]methanesulfonamide;
N-[2-ethyl-4-(4-fluorophenyl)-3-oxo-3,4-dihydro-2H-1,4-benzoxazin -7-yl]methanesulfonamide;
N-[2,2-dimethyl-3-oxo-4-[(4-trifluoromethyl)phenyl]-3,4-dihydro-2H-1,4-benzoxazin-7-yl]methanesulfonamide;
N-[4-(4-fluorophenyl)-2,2-dimethyl-3-oxo-3,4-dihydro-2H-1,4-benzoxazin -7-yl]sulfamide;
N-[4-(2,4-difluorophenyl)-2,2-dimethyl-3-oxo-3,4-dihydro-2H-1,4-benzoxazin-7-yl]methanesulfonamide;
N-[4-(4-fluorophenyl)-2,2-dimethyl-3-thioxo-3,4-dihydro-2H-1,4-benzoxazin-7-yl]methanesulfonamide;
N-[4-(4-fluoro-2-methylphenyl)-2,2-dimethyl-3-oxo-3,4-dihydro-2H-1,4-benzoxazin-7-yl]methanesulfonamide;
N-[4-(4-chloro-3-methoxyphenyl)-2,2-dimethyl-3-oxo-3,4-dihydro-2H-1,4-benzoxazin-7-yl]methanesulfonamide;
N-[4-(4-fluoro-3-methoxyphenyl)-2,2-dimethyl-3-oxo-3,4-dihydro-2H-1,4-benzoxazin-7-yl]methanesulfonamide;
4-(4-fluoro-3-methylphenyl)-N,2,2-trimethyl-3-oxo-3,4-dihydro-2H-1,4-benzoxazine-7-sulfonamide;
N-[4-[3-(dimethylamino)-4-fluorophenyl]-2,2-dimethyl-3-oxo-3,4-dihydro-2H -1,4-benzoxazin-7-yl]methanesulfonamide;
N-[4-(3-chloro-4-fluorophenyl)-3-oxo-3,4-dihydro-2H-1,4-benzoxazin-7-yl]-methanesulfonamide;
N-[4-(2-chloro-4-fluorophenyl)-2,2-dimethyl-3-oxo-3,4-dihydro-2H-1,4-benzoxazin-7-yl]methanesulfonamide;
N-[4-(4-chloro-2-fluorophenyl)-2,2-dimethyl-3-oxo-3,4-dihydro-2H-1,4-benzoxazin-7-yl]methanesulfonamide;
N-[4-(4-chloro-2-methylphenyl)-2,2-dimethyl-3-oxo-3,4-dihydro-2H-1,4-benzoxazin-7-yl]methanesulfonamide;
N-[4-(4-bromophenyl)-2,2-dimethyl-3-oxo-3,4-dihydro-2H-1,4-benzoxazin -7-yl]methanesulfonamide;
N-[4-(4-fluorophenyl)-2,2,6-trimethyl-3-oxo-3,4-dihydro-2H-1,4-benzoxazin -7-yl]methanesulfonamide;
N-[6-amino-4-(4-fluorophenyl)-2,2-dimethyl-3-oxo-3,4-dihydro-2H-1,4-benzoxazin-7-yl]methanesulfonamide;
N-[4-[3-(difluoromethyl)-4-fluorophenyl]-2,2-dimethyl-3-oxo-3,4-dihydro-2H -1,4-benzoxazin-7-yl]methanesulfonamide;

4-(4-chlorophenyl)-N,2,2-trimethyl-3-oxo-3,4-dihydro-2H-1,4-benzoxazine-7-sulfonamide;
N-[4-(4-chloro-2-cyanophenyl)-2,2-dimethyl-3-oxo-3,4-dihydro-2H-1,4-benzoxazin-7-yl]methanesulfonamide;
4-(4-bromophenyl)-N,2,2-trimethyl-3-oxo-3,4-dihydro-2H-1,4-benzoxazine-7-sulfonamide;
N-[4-(5-chloropyridin-2-yl)-2,2-dimethyl-3-oxo-3,4-dihydro-2H-1,4-benzoxazin-7-yl]methanesulfonamide;
N-[5-chloro-4-(4-fluorophenyl)-2,2-dimethyl-3-oxo-3,4-dihydro-2H-1,4-benzoxazin-7-yl]methanesulfonamide;
N-[4-(4-bromo-2-methylphenyl)-2,2-dimethyl-3-oxo-3,4-dihydro-2H-1,4-benzoxazin-7-yl]methanesulfonamide;
N-[4-[4-chloro-3-(trifluoromethyl)phenyl]-2,2-dimethyl-3-oxo-3,4-dihydro-2H-1,4-benzoxazin-7-yl]methanesulfonamide;
N-[4-[3-fluoro-4-(trifluoromethyl)phenyl]-2,2-dimethyl-3-oxo-3,4-dihydro-2H-1,4-benzoxazin-7-yl]methanesulfonamide;
N-[4-(4-chloro-3-fluorophenyl)-2,2-dimethyl-3-oxo-3,4-dihydro-2H-1,4-benzoxazin-7-yl]methanesulfonamide;
N-[4-(4-chloro-3-methylphenyl)-2,2-dimethyl-3-oxo-3,4-dihydro-2H-1,4-benzoxazin-7-yl]methanesulfonamide;
N-[4-(3-fluoro-4-methylphenyl)-2,2-dimethyl-3-oxo-3,4-dihydro-2H-1,4-benzoxazin-7-yl]methanesulfonamide;
4-(4-chloro-2-methylphenyl)-N,2,2-trimethyl-3-oxo-3,4-dihydro-2H-1,4-benzoxazine-7-sulfonamide;
N-[4-(2,4-dimethylphenyl)-2,2-dimethyl-3-oxo-3,4-dihydro-2H-1,4-benzoxazin-7-yl]methanesulfonamide;
N-[4-(3-chloro-4-methylphenyl)-2,2-dimethyl-3-oxo-3,4-dihydro-2H-1,4-benzoxazin-7-yl]methanesulfonamide;
N-[4-(3,4-difluoro-5-methoxyphenyl)-2,2-dimethyl-3-oxo-3,4-dihydro-2H-1,4-benzoxazin-7-yl]methanesulfonamide;
N-[4-(3,4-dichlorophenyl)-2,2-dimethyl-3-oxo-3,4-dihydro-2H-1,4-benzoxazin-7-yl]methanesulfonamide;
N-[2,2-dimethyl-4-(2-naphthyl)-3-oxo-3,4-dihydro-2H-1,4-benzoxazin-7-yl]-methanesulfonamide;
N-[4-(4-fluoro-2,6-dimethylphenyl)-2,2-dimethyl-3-oxo-3,4-dihydro-2H-1,4-benzoxazin-7-yl]methanesulfonamide;
N-[5-bromo-4-(4-fluorophenyl)-2,2-dimethyl-3-oxo-3,4-dihydro-2H-1,4-benzoxazin-7-yl]methanesulfonamide;
N-[4-(5-chloro-2-methylphenyl)-2,2-dimethyl-3-oxo-3,4-dihydro-2H-1,4-benzoxazin-7-yl]methanesulfonamide;
N-[5-chloro-4-(4-chlorophenyl)-2,2-dimethyl-3-oxo-3,4-dihydro-2H-1,4-benzoxazin-7-yl]methanesulfonamide;
N-[4-(4-fluorophenyl)-2,2,5-trimethyl-3-oxo-3,4-dihydro-2H-1,4-benzoxazin-7-yl]methanesulfonamide;
N-[4-(4-bromo-3-methylphenyl)-2,2-dimethyl-3-oxo-3,4-dihydro-2H-1,4-benzoxazin-7-yl]methanesulfonamide;
N-[4-(2,2-difluoro-1,3-benzodioxol-5-yl)-2,2-dimethyl-3-oxo-3,4-dihydro-2H-1,4-benzoxazin-7-yl]methanesulfonamide;
N-(4-mesityl-2,2-dimethyl-3-oxo-3,4-dihydro-2H-1,4-benzoxazin-7-yl)-methanesulfonamide;
N-[4-(2,6-dimethylphenyl)-2,2-dimethyl-3-oxo-3,4-dihydro-2H-1,4-benzoxazin-7-yl]methanesulfonamide;
N-[4-(4-chloro-2,6-dimethylphenyl)-2,2-dimethyl-3-oxo-3,4-dihydro-2H-1,4-benzoxazin-7-yl]methanesulfonamide;
N-[4-(5-bromo-3-methylpyridin-2-yl)-2,2-dimethyl-3-oxo-3,4-dihydro-2H-1,4-benzoxazin-7-yl]methanesulfonamide;
N-[5-fluoro-4-(4-fluorophenyl)-2,2-dimethyl-3-oxo-3,4-dihydro-2H-1,4-benzoxazin-7-yl]methanesulfonamide;
N-[4-(3,5-dichloropyridin-2-yl)-2,2-dimethyl-3-oxo-3,4-dihydro-2H-1,4-benzoxazin-7-yl]methanesulfonamide;
N-[4-(4-fluoro-2,3-dimethylphenyl)-2,2-dimethyl-3-oxo-3,4-dihydro-2H-1,4-benzoxazin-7-yl]methanesulfonamide;
N-[4-(3-chloro-2-methylphenyl)-2,2-dimethyl-3-oxo-3,4-dihydro-2H-1,4-benzoxazin-7-yl]methanesulfonamide;
N-[4-(5-fluoro-2-methylphenyl)-2,2-dimethyl-3-oxo-3,4-dihydro-2H-1,4-benzoxazin-7-yl]methanesulfonamide;
N-[2,2-dimethyl-3-oxo-4-(1-phenylethyl)-3,4-dihydro-2H-1,4-benzoxazin-7-yl]methanesulfonamide;
N-[2,2-dimethyl-4-(3-methylbenzyl)-3-oxo-3,4-dihydro-2H-1,4-benzoxazin-7-yl]methanesulfonamide;
N-[2,2-dimethyl-4-[2-methyl-5-(trifluoromethyl)phenyl]-3-oxo-3,4-dihydro-2H-1,4-benzoxazin-7-yl]methanesulfonamide;
N-[2,2-dimethyl-3-oxo-4-(2,4,6-trifluorophenyl)-3,4-dihydro-2H-1,4-benzoxazin-7-yl]methanesulfonamide;
2-chloro-5-[2,2-dimethyl-7-[(methylsulfonyl)amino]-3-oxo-2,3-dihydro-4H-1,4-benzoxazin-4-yl]benzyl benzoate;
N-[4-(4-chloro-2-methoxy-5-methylphenyl)-2,2-dimethyl-3-oxo-3,4-dihydro-2H-1,4-benzoxazin-7-yl]methanesulfonamide;
N-[4-(6-chloro-2,2-difluoro-1,3-benzodioxol-5-yl)-2,2-dimethyl-3-oxo-3,4-dihydro-2H-1,4-benzoxazin-7-yl]methanesulfonamide;
N-[2,2-dimethyl-4-(3-methyl-5-nitropyridin-2-yl)-3-oxo-3,4-dihydro-2H-1,4-benzoxazin-7-yl]methanesulfonamide;
N-[4-(5-chloro-3-methylpyridin-2-yl)-2,2-dimethyl-3-oxo-3,4-dihydro-2H-1,4-benzoxazin-7-yl]methanesulfonamide;
N-[4-[4-fluoro-2-(trifluoromethyl)phenyl]-2,2-dimethyl-3-oxo-3,4-dihydro-2H-1,4-benzoxazin-7-yl]methanesulfonamide;
N-[2,2-dimethyl-4-[2-methyl-4-(trifluoromethyl)phenyl]-3-oxo-3,4-dihydro-2H-1,4-benzoxazin-7-yl]methanesulfonamide;
N-[4-(4-fluorophenyl)-2,2-dimethyl-3-oxo-5-vinyl-3,4-dihydro-2H-1,4-benzoxazin-7-yl]methanesulfonamide;
N-[4-(4-chlorophenyl)-5-fluoro-2,2-dimethyl-3-oxo-3,4-dihydro-2H-1,4-benzoxazin-7-yl]methanesulfonamide;
N-[4-(5-chloropyridin-2-yl)-5-fluoro-2,2-dimethyl-3-oxo-3,4-dihydro-2H-1,4-benzoxazin-7-yl]methanesulfonamide;
N-[4-[3-chloro-5-(trifluoromethyl)pyridin-2-yl]-2,2-dimethyl-3-oxo-3,4-dihydro-2H-1,4-benzoxazin-7-yl]methanesulfonamide;
N-[4-(3-chlorophenyl)-2,2-dimethyl-3-oxo-3,4-dihydro-2H-1,4-benzoxazin-7-yl]methanesulfonamide;
N-[4-[5-bromo-6-methylpyridin-2-yl]-2,2-dimethyl-3-oxo-3,4-dihydro-2H-1,4-benzoxazin-7-yl]methanesulfonamide;
N-[5-fluoro-4-(5-fluoropyridin-2-yl)-2,2-dimethyl-3-oxo-3,4-dihydro-2H-1,4-benzoxazin-7-yl]methanesulfonamide;
N-[2,2-dimethyl-3-oxo-4-[5-(trifluoromethyl)-2-thienyl]-3,4-dihydro-2H-1,4-benzoxazin-7-yl]methanesulfonamide;
N-[4-(6-chloro-4-methylpyridin-3-yl)-2,2-dimethyl-3-oxo-3,4-dihydro-2H-1,4-benzoxazin-7-yl]methanesulfonamide;
N-[4-(5-bromopyridin-2-yl)-2,2-dimethyl-3-oxo-3,4-dihydro-2H-1,4-benzoxazin-7-yl]methanesulfonamide;
N-[4-[4-chloro-3-(hydroxymethyl)phenyl]-2,2-dimethyl-3-oxo-3,4-dihydro-2H-1,4-benzoxazin-7-yl]methanesulfonamide;
N-[4-(6-bromo-5-methylpyridin-3-yl)-2,2-dimethyl-3-oxo-3,4-dihydro-2H-1,4-benzoxazin-7-yl]methanesulfonamide;
N-[4-(6-chloro-2-methylpyridin-3-yl)-2,2-dimethyl-3-oxo-3,4-dihydro-2H-1,4-benzoxazin-7-yl]methanesulfonamide;

N-{2,2-dimethyl-3-oxo-4-[5-(trifluoromethyl)pyridin-2-yl]-3,4-dihydro-2H-1,4-benzoxazin-7-yl}methanesulfonamide;
N-{2,2-dimethyl-4-[3-methyl-6-(trifluoromethyl)pyridin-2-yl]-3-oxo-3,4-dihydro-2H-1,4-benzoxazin-7-yl}methanesulfonamide;
N-[4-(5-chloro-3-fluoropyridin-2-yl)-2,2-dimethyl-3-oxo-3,4-dihydro-2H-1,4-benzoxazin-7-yl]methanesulfonamide;
N-[4-(3-chlorophenyl)-5-fluoro-2,2-dimethyl-3-oxo-3,4-dihydro-2H-1,4-benzoxazin-7-yl]methanesulfonamide;
N-[4-(5-bromopyridin-2-yl)-5-fluoro-2,2-dimethyl-3-oxo-3,4-dihydro-2H-1,4-benzoxazin-7-yl]methanesulfonamide;
N-[4-(5-chloro-3-methylpyridin-2-yl)-5-fluoro-2,2-dimethyl-3-oxo-3,4-dihydro -2H-1,4-benzoxazin-7-yl]methanesulfonamide;
N-{5-fluoro-2,2-dimethyl-3-oxo-4-[5-(trifluoromethyl)pyridin-2-yl]-3,4-dihydro-2H-1,4-benzoxazin-7-yl}methanesulfonamide;
N-[4-(5-fluoro-3-methylpyridin-2-yl)-2,2-dimethyl-3-oxo-3,4-dihydro-2H-1,4-benzoxazin-7-yl]methanesulfonamide;
N-[4-(5-chloro-3-fluoropyridin-2-yl)-5-fluoro-2,2-dimethyl-3-oxo-3,4-dihydro -2H-1,4-benzoxazin-7-yl]methanesulfonamide;
N-[4-[4-chloro-3-(hydroxymethyl)phenyl]-5-fluoro-2,2-dimethyl-3-oxo-3,4-dihydro-2H-1,4-benzoxazin-7-yl]methanesulfonamide;
2-chloro-5-[5-fluoro-2,2-dimethyl-7-[(methylsulfonyl)amino]-3-oxo-2,3-dihydro-4H-1,4-benzoxazin-4-yl]benzyl benzoate;
N-[4-(2,6-dimethylpyridin-3-yl)-2,2-dimethyl-3-oxo-3,4-dihydro-2H-1,4-benzoxazin-7-yl]methanesulfonamide;
N-[5-cyclopropyl-4-(4-fluorophenyl)-2,2-dimethyl-3-oxo-3,4-dihydro-2H-1,4-benzoxazin-7-yl]methanesulfonamide;
N-[5-fluoro-4-[3-fluoro-4-(trifluoromethyl)phenyl]-2,2-dimethyl-3-oxo-3,4-dihydro-2H-1,4-benzoxazin-7-yl]methanesulfonamide;
N-[5-fluoro-2,2-dimethyl-3-oxo-4-[4-(trifluoromethyl)phenyl]-3,4-dihydro-2H -1,4-benzoxazin-7-yl]methanesulfonamide;
N-[5-fluoro-4-[4-fluoro-3-(trifluoromethyl)phenyl]-2,2-dimethyl-3-oxo-3,4-dihydro-2H-1,4-benzoxazin-7-yl]methanesulfonamide;
N-[4-(3-chloro-4-fluorophenyl)-5-fluoro-2,2-dimethyl-3-oxo-3,4-dihydro-2H -1,4-benzoxazin-7-yl]methanesulfonamide;
N-[4-(3,4-difluorophenyl)-5-fluoro-2,2-dimethyl-3-oxo-3,4-dihydro-2H-1,4-benzoxazin-7-yl]methanesulfonamide;
N-[5-fluoro-4-(5-fluoro-6-methylpyridin-2-yl)-2,2-dimethyl-3-oxo-3,4-dihydro -2H-1,4-benzoxazin-7-yl]methanesulfonamide;
N-[4-(6-chloro-2-methylpyridin-3-yl)-5-fluoro-2,2-dimethyl-3-oxo-3,4-dihydro -2H-1,4-benzoxazin-7-yl]methanesulfonamide;
N-[4-3-chloro-2-fluorophenyl)-5-fluoro-2,2-dimethyl-3-oxo-3,4-dihydro-2H -1,4-benzoxazin-7-yl]methanesulfonamide;
N-[4-(5-fluoro-6-methylpyridin-2-yl)-2,2-dimethyl-3-oxo-3,4-dihydro-2H-1,4-benzoxazin-7-yl]methanesulfonamide;
N-[4-(benzothien-2-yl)-2,2-dimethyl-3-oxo-3,4-dihydro-2H-1,4-benzoxazin -7-yl]methanesulfonamide;
N-[4-(benzofuran-2-yl)-2,2-dimethyl-3-oxo-3,4-dihydro-2H-1,4-benzoxazin -7-yl]methanesulfonamide;
N-[4-[2-chloro-6-(trifluoromethyl)pyridin-3-yl]-2,2-dimethyl-3-oxo-3,4-dihydro-2H-1,4-benzoxazin-7-yl]methanesulfonamide;
N-[4-(4-fluorophenyl)-5-(methoxymethyl)-2,2-dimethyl-3-oxo-3,4-dihydro-2H -1,4-benzoxazin-7-yl]methanesulfonamide;
N-[2,2-dimethyl-4-[3-methyl-5-(trifluoromethyl)pyridin-2-yl]-3-oxo-3,4-dihydro-2H-1,4-benzoxazin-7-yl]methanesulfonamide;
N-[2,2-dimethyl-4-[2-methyl-6-(trifluoromethyl)pyridin-3-yl]-3-oxo-3,4-dihydro-2H-1,4-benzoxazin-7-yl]methanesulfonamide;
N-[2,2-dimethyl-4-[2-methyl-5-(trifluoromethyl)pyridin-3-yl]-3-oxo-3,4-dihydro-2H-1,4-benzoxazin-7-yl]methanesulfonamide;
N-[5-ethyl-4-(4-fluorophenyl)-2,2-dimethyl-3-oxo-3,4-dihydro-2H-1,4-benzoxazin-7-yl]methanesulfonamide;
N-[5-fluoro-2,2-dimethyl-3-oxo-4-[5-(trifluoromethyl)-2-thienyl]-3,4-dihydro -2H-1,4-benzoxazin-7-yl]methanesulfonamide;
N-[5-fluoro-4-(5-fluoro-3-methylpyridin-2-yl)-2,2-dimethyl-3-oxo-3,4-dihydro -2H-1,4-benzoxazin-7-yl]methanesulfonamide;
N-[4-(6-chloro-2,2-difluoro-1,3-benzodioxol-5-yl)-5-fluoro-2,2-dimethyl-3-oxo -3,4-dihydro-2H-1,4-benzoxazin-7-yl]methanesulfonamide;
N-[4-(2,2-difluoro-1,3-benzodioxol-5-yl)-5-fluoro-2,2-dimethyl-3-oxo-3,4-dihydro-2H-1,4-benzoxazin-7-yl]methanesulfonamide;
N-[4-(5-bromo-3-methylpyridin-2-yl)-5-fluoro-2,2-dimethyl-3-oxo-3,4-dihydro -2H-1,4-benzoxazin-7-yl]methanesulfonamide;
N-[5-fluoro-2,2-dimethyl-4-(3-methyl-5-(trifluoromethyl)pyridin-2-yl]-3-oxo -3,4-dihydro-2H-1,4-benzoxazin-7-yl]methanesulfonamide;
N-[4-(4-chloro-2-methylphenyl)-5-fluoro-2,2-dimethyl-3-oxo-3,4-dihydro-2H -1,4-benzoxazin-7-yl]methanesulfonamide;
N-[4-(3-amino-4-fluorophenyl)-2,2-dimethyl-3-oxo-3,4-dihydro-2H-1,4-benzoxazin-7-yl]methanesulfonamide;
N-[4-(4-fluoro-2-methoxyphenyl)-2,2-dimethyl-3-oxo-3,4-dihydro-2H-1,4-benzoxazin-7-yl]methanesulfonamide;
4-(3-chloro-4-fluorophenyl)-N,2,2-trimethyl-3-oxo-3,4-dihydro-2H-1,4-benzoxazine-7-sulfonamide;
N-{2,2-dimethyl-3-oxo-4-[3-(trifluoromethyl)phenyl]-3,4-dihydro-2H-1,4-benzoxazin-7-yl}methanesulfonamide; and
N-{2,2-dimethyl-4-[2-methyl-3-(trifluoromethyl)phenyl]-3-oxo-3,4-dihydro-2H -1,4-benzoxazin-7-yl}methanesulfonamide;
or a pharmaceutically acceptable salt thereof.

When the compound [I] of the present invention has an asymmetric carbon atom(s) in its molecule, it may exist in the form of a stereoisomer thereof (diastereoisomers, optical isomers) owing to said asymmetric carbon atom(s) thereof, and the present invention also includes either one of the stereoisomers and a mixture thereof.

The nitrogen-containing heterobicyclic compounds [I] of the present invention can be useful for prevention or treatment of various diseases/disease states caused by or associated with MR and/or aldosterone. Such diseases include the following diseases (1) to (6):

(1) Circulation disorders or blood-related disorders: essential hypertension; secondary hypertension (e.g., renovascular hypertension, hypertension due to excessive body fluid); pulmonary hypertension; hypotension; abnormal circadian rhythm in blood pressure; heart failure (e.g., acute heart failure, chronic heart failure, congestive heart failure); angina pectoris; cardiac infarction, cardiomyopathy; cardiac hypertrophy; cardiomyositis; myocardial/vascular fibrosis; myocardial ischemia; baroreceptor dysfunction; arrhythmias; tachycardia; cerebrovascular accidents (CVA) and sequelae thereof; transient ischemic attack (TIA); stroke; cerebrovascular dementia; hypertensive encephalopathy; cerebral infarction; cerebral edema; cerebral circulation disorders; peripheral circulation disorders including Raynoud's disease and Buerger's disease; intermittent claudication; venous function disorders; arteriosclerosis (e.g., coronary artery screlosis, cerebrovascular screlosis, peripheral vascular screlosis); vascular hyperplasia; vascular hyperplasia/occlusion after interventions including percutaneous transluminal coronary angioplasty (PTCA); vascular reocclusion/restenosis after bypass graft (e.g., CABG); rejection after organ transplantation; thrombosis; deep vein thrombosis; obstructive peripheral circulation disorders; obstructive arteriosclerosis; occlusive thromboangiitis; thrombocytopenia; erythrocytosis; multi organ insufficiency; vascular endothelium dysfunction; or kidney disorders (e.g., renal insufficiency, nephritis, glomerulonephritis, IgA nephropathy, progressive nephropathy, glomerulosclerosis, diabetic nephropathy, thrombotic microangiopathy, diseases complicated to dialysis, radionephropathy); vascular purpura; autoimmune hemolytic anemia; disseminated intravascular coagulation (DIC); multiple myelomatosis and the like;

(2) Metabolic diseases: hyperglycemia/diabetes mellitus and diseases complicated thereto (e.g., diabetic nephrosis, diabetic retinopathy, diabetic neuropathy); metabolic syndrome or metabolic disorders (e.g., hyperlipidemia, hypercholesterolemia, obesity, hyperuricemia, hypokalemia, hypernatremia, glucose intolerance); and the like;

(3) Central nervous system or neurodegenerative disorders: neural disorders caused by stroke, cerebral infarction, cranial trauma, spinal cord injury or brain edema; perception disorders/impairment; autonomic nervous dysfunction/impairment; multiple screlosis; memory disorders; consciousness disorders; mood disorders including depression and bipolar disorder; anxiety disorder; personality disorder; amnesia; dementia; epilepsy; alcohol dependency; Alzheimer's disease; Parkinson's disease; amyotrophic lateral sclerosis; and the like;

(4) Inflammatory or allergic diseases: rheumatoid arthritis; gout; hylotropic gonitis; osteoarthritis; periosteal inflammation; bursitis; ankylosing myelitis; atopic dermatitis; contact dermatitis; psoriasis; allergic rhinitis; hay fever; asthma; urticaria; bronchitis; inflammatory pulmonary diseases (e.g., pneumonia, chronic obstructive pulmonary disease, interstitial pneumonia; *Pneumocystis carinii* pneumonia; pulmonary tuberculosis; pulmonary sarcoidosis); inflammatory bowel disease (e.g., Crohn's disease, ulcerative colitis); collagenosis (e.g., systemic lupus erythematosus, pachyderma, polyarteritis); meningitis; Wegener's granulomatosis; rheumatic fever; post operative/traumatic inflammation; pharyngitis; cystitis; anaphylaxis; tendinitis; conjunctivitis; inflammatory ophthalmic diseases; and the like;

(5) Endocrine diseases: primary or secondary aldosteronism; pseudo-aldosteronism; Bartter's syndrome and the like;

(6) Other diseases including topical diseases: hepatic diseases (e.g., hepatitis, cirrhosis); portal hypertension; digestive organ diseases (e.g., gastritis, gastric ulcer, gastric cancer, post-operative gastric disorder, esophageal ulcer, rupture of gastro-esophageal varix, colon polyp, pancreatitis, biliary calculus, piles and the like); prostatic disorders (e.g., prostatic hyperplasia, prostate cancer); bone disorders (e.g., tissue damage caused by bone fracture, osteoporosis, osteomalacia, bone Behcet disease); cancer/tumor (malignant melanoma, leukemia, malignant lymphoma, gastric cancer, intestinal cancer); cachexia; metastasis of cancer; female diseases (e.g., climacteric suffering, gestosis, endometriosis, hysteromyoma, ovarian diseases, mammary gland diseases); infection; septic shock; endotoxin shock; glaucoma; increased occular tension; Meniere disease; dysphagia; sleep apnea; myasthenia gravis; dyalysis hypotension; chronic fatigue syndrome and the like.

The compounds [I] of the present invention include those having potent MR-antagonizing activity (aldosterone-antagonizing activity) and such a compound or a pharmaceutically acceptable salt thereof is particularly useful for prevention or treatment (including its use as diuretics) of various diseases/disease states caused by or associated with hyperactivity of MR and/or increase in aldosterone level, such as cardiovascular diseases including hypertension, heart failure, cardiac infarction, angina pectoris, cardiac hypertrophy, cardiomyositis, cardiac/vascular fibrosis, baroreceptor dysfunction, increased body fluid and arrhythmia, or endocrine diseases including primary/secondary aldosteronism, Addison's disease, Cushing's syndrome and Bartter's syndrome.

The compound [I] of the present invention can be clinically used either in the free form or in the form of a pharmaceutically acceptable salt thereof. The pharmaceutically acceptable salt of the compound includes a salt with an inorganic acid such as hydro-chloride, sulfate, phosphate or hydrobromide, or a salt with an organic acid such as acetate, fumarate, oxalate, citrate, methanesulfonate, benzenesulfonate, tosylate or maleate.

The compound [I] or a pharmaceutically acceptable salt thereof includes either intramolecular salt or an additive thereof, and solvates or hydrates thereof.

The present compound [I] or a pharmaceutically acceptable salt thereof, in the form of such compound itself or in the form of a pharmaceutical composition comprising the compound and a pharmaceutically acceptable carrier, can be administered either orally or parenterally. The formulation of such pharmaceutical composition should not be limited and includes any conventional preparations such as tablets, granules, capsules, powders, injections, inhalants or suppositories.

The dose of the compound [I] of the present invention or a pharmaceutically acceptable salt thereof may vary in accordance with the administration routes, and the ages, weights and conditions of the patients. For example, when administered parenterally, it is usually in the range of about 0.001 to 10 mg/kg/day, preferably in the range of about 0.01 to 1 mg/kg/day. When administered orally, it is usually in the range of about 0.01 to 100 mg/kg/day, preferably in the range of 0.1 to 10 mg/kg/day.

A compound [I] of the present invention can be used solely or in combination with one or more other medicaments depending the diseases to be treated and the like. Examples of such medicament include those as follows:

(a) antihypertensive agents: angiotensin-converting enzyme inhibitors (e.g., enalapril maleate, imidapril hydrochloride, captopril, cilazapril, lisinopril, delapril hydrochloride, temocapril hydrochloride, benazepril hydrochloride, perindopril erbumine, fosinopril sodium, quinapril hydrochloride, moexipril hydrochloride, ramipril, trandorapril, alacepril); angiotensin II receptor blockers (e.g., losartan potassium, candesartan cylexetil, varsartan, irbesartan, telmisartan, olmesartan medoxomil, eprosartan mesylate, forasartan); β-blockers (e.g., atenolol, betaxolol hydrochloride, bisoplolol fumarate, metoprolol tartrate, metprolol succinate, propranolol hydrochloride, nadolol, timolol maleate, acebutolol hydrochloride, penbutolol sulfate, pindolol, carteolol hydrochloride, nipradilol); α/β-blockers (e.g., carvedilol, labetalol hydrochloride); calcium antagonists (e.g., amlodipine besylate, ferodipine, isradipine, nifedipine, nicardipine hydrochloride, nisoldipine, nitrendipine, benidipine, manidipine hydrochloride, efonidipine hydrochloride, diltiazem hydrochloride); $\alpha_1$-blockers (doxazosin mesylate, prazosin hydrochloride, terazosin hydrochloride); central $\alpha_2$-agonists or other centrally active agent (clonidine hydrochloride, reserpine, methyldopa); vasodilators (hydralazine hydrochloride, minoxidil) and the like, (b) diuretics: thiazide diuretics (e.g., chlorothiazide, hydrochlorothiazide, benzylhydrochlorothiazide, hydroflumethiazide, trichloromethiazide, polythiazide, chlorthalidone, indapamide, metolazone); loop diuretics (e.g., bumetanide, furosemide, tolusemide, mefruside, etacrynic acid); potassium-sparing diuretics (e.g., amiloride hydrochloride, triamterene) and the like, (c) agents for heart failure: nitrates (e.g., nitroglycerin); digitalis (e.g., digoxin, digitoxin); cathecolamines (e.g., dobutamine hydrochloride, denopamine); endotheline antagonists (e.g., bosentan); phosphodiesterase inhibitors (e.g., milrinone lactate, amrinone, olprinone); neutral endopeptidase inhibitors (e.g., fasidotril); atrial natriuretic peptides and the like, (d) anti-arrhythmic agents: sodium channel blockers (e.g., procainamide hydrochloride, flecainide acetate, quinidine sulfate); potassium channel blockers (e.g., amiodarone hydrochloride); calcium channel blockers (e.g., verapamil hydrochloride) and the like, (e) agents for hyperlipidemia: HMG-CoA reductase inhibitors (e.g., pravastatin sodium, atorvastatin calcium, simvastatin, cerivastatin, lovastatin, fluvastatin sodium, rosuvastatin calcium, pitavastatin calcium); fibrate derivatives (e.g., bezafibrate, feno-fibrate, clynofibrate, clofibrate, gemfibrozil); squalene synthetase inhibitors and the like, (f) anti-thrombotic agents: anti-coagulation agents (e.g., warfarin sodium, heparin sodium, antithrombin III); thrombolytic agents (e.g., urokinase, t-PA); anti-platelet agents (e.g., aspirin, ticropidin hydrochloride, sulfinpyrazone, dipyridamol, cilostazole) and the like, (g) agents for diabetes mellitus/diabetes-complicated diseases: insulin, alpha-glucosidase inhibitors (e.g., voglibose, acarbose, miglitol, emiglitate); biguanides (e.g., metformin hydrochloride, buformin hydrochloride, fenformin hydrochloride); insulin resistance-improving agents (e.g., pioglitazone, troglitazone, rosiglitazone); insulin secretion-promoting agents (e.g., sulfonylurea derivatives such as tolbutamide, glibenclamide, gliclazide, gliclopiramide, chlorpropamide, glimepiride, glybuzide, glibuzole, tolazamide and acetohexamide); amiline antagonists (e.g., pramlintide); aldose reductase inhibitors (e.g., epalrestat, tolrestat, zenarestat, fidarestat, minalrestat, zopolrestat); neurorophic factors (e.g., nerve-growth factors/NGF); AGE inhibitors (e.g., pimagedin, piratoxatine); neurorophic factor production-promoting agents and the like, (h) anti-obesity agents: centrally acting anti-obesity agents (e.g., magindol, fenfluramin, dexfenflurami, sibutramin); pancreatic lipase inhibitors (e.g., orlistat); beta-3 agonists (e.g., SB-226552, BMS-196085, SR-5611-A); anorexigenic peptides (e.g., reptin); cholecystokinin receptor agonists (e.g., lintitript) and the like, (i) non steroidal anti-inflammatory agents: acetaminophen, ibuprofen, ketoprofen, ethenzamide, naproxen, dichlofenac, loxoprofen and the like, (j) chemotherapeutics: metabolism antagonists (5-fluorouracil, methotrexate); anti-cancer agents (e.g., vincristine, taxole, cysplatin) and the like, or (k) immuno-modulating agents: immunosuppressants (e.g., cyclosporin, tacrolimus, azathiopurin); immunostimulants: (e.g., crestin, rentinan, schizophyllan); cytokines (e.g., interleukin-1, interferon); cyclooxygenase inhibitors (e.g., indomethacin, selecoxib, valdecoxib, meloxicam); anti-TNFα antibody (e.g., infliximab) and the like.

When the compound [I] is used in a combination with other medicaments, the form of administration include (1) administration of a single dosage form (a fixed dose combination) containing the compound [I] and such other medicaments, and (2) concomitant administration of a dosage form containing the compound [I] and a dosage form containing such other medicament(s). In case of (2) mentioned above, the route and time of the administration may varied among the dosage forms.

The compound of the present invention [I] can be prepared by the following methods but should not be construed to be limited thereto.

Method A:

Among the compounds [I] of the present invention, a compound in which $R^1$ is a group of the formula: $R^aSO_2NH$—, namely a compound of the following formula [I-A]:

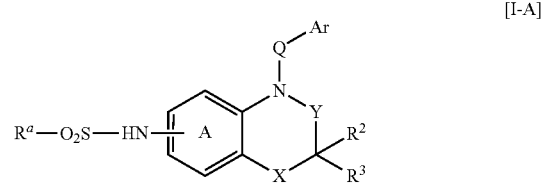

[I-A]

wherein the symbols are the same as defined above or a pharmaceutically acceptable salt thereof can be prepared by reacting a compound of the formula [II-A]:

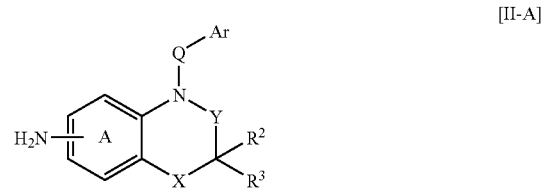

[II-A]

wherein the symbols are the same as defined above with a compound of the formula [a]:

$R^aSO_2$-Hal  [a]

wherein Hal is a halogen atom and the other symbol is the same as defined above.

Examples of the halogen atom in the compound [a] include a chlorine atom, bromine atom and the like.

The reaction of the compound [II-A] with the compound [a] can be carried out in an appropriate solvent or without solvent in the presence or absence of a base.

Examples of the solvent include any inert solvent which does not disturb the reaction, such as a halogenated aliphatic hydrocarbon including chloroform, dichloromethane and dichloro-ethane, an aromatic hydrocarbon including benzene, toluene and xylene, an ether including diethylether, diisopropylether, tetrahydrofuran, dioxane and 1,2-dimethoxy-ethane, an ester including ethyl acetate, an amide including N,N-dimethylformamide, N,N-dimethylacetamide and 1,3-dimethyl-2-imidazolidinone, a nitrile including acetonitrile, dimethylsulfoxide, pyridine, 2.6-lutidine, a mixture thereof or a combination of water and such solvent. Among these, examples of the preferable solvent include dichloromethane, chloroform, toluene, xylene, tetrahydrofuran, dioxane, N,N-dimethyl-formamide, N,N-dimethylacetamide, 1,3-dimethyl-2-imidazolidinone and pyridine, and the more preferable solvent may be dichloromethane, chloroform, tetrahydrofuran or pyridine. The base may be an organic base or an inorganic base. The organic base may be a tri(alkyl)amine such as triethylamine, tributylamine, diisopropylethylamine and the like, a tertiary cyclic amine such as 1,4-diazabicyclo[2.2.2]octane, 1,5-diazabicyclo[4.3.0]non-5-en, 1,8-diazabicyclo[5.4.0]undec-7-en and the like, an amine including N,N-dimethylanilline, N,N-diethylanilline, 4-dimethylaminopyridine and the like, pyridine, 2,6-lutidine, 2,3,5-collidine and the like. The inorganic base may be an alkali metal carbonate such as sodium carbonate, potassium carbonate, cesium carbonate and the like, an alkali earth metal carbonate such as calcium carbonate and the like, an alkali metal hydrogencarbonate such as sodium hydrogencarbonate, potassium hydrogencarbonate and the like, and an alkali metal hydroxide such as sodium hydroxide, potassium hydroxide, lithium hydroxide and the like. Among them, pyridine, triethylamine or an alkali metal carbonate is preferable.

In the above-mentioned reaction process, the compound [a] can be used in an amount of 1 to 10 moles, preferably 1 to 2 moles per one mole of the compound [II-A]. The base can be used in an amount of 1 to 10 moles, preferably 1 to 2 moles per one mole of the compound [II-A]. The reaction can be carried out under cooling to heating, preferably under ice-cooling to room temperature.

Besides, among the compounds [I], a compound of the following formula [I-A2]:

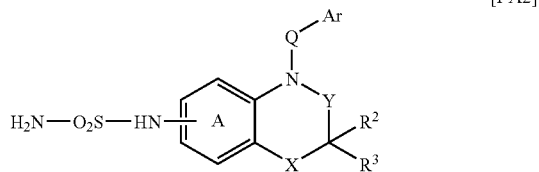

wherein the symbols are the same as defined above can be also prepared by reacting a compound [II-A] with an isocyanate compound of the formula [a-2]:

wherein the symbol is the same as defined above. The present reaction can be carried out in an appropriate solvent in the presence of a base. Examples of the solvent include any inert solvent which does not disturb the reaction, such as a mixture of an ether including tetrahydrofuran and water and the like. The base may be those mentioned above such as an amine including triethylamine and the like. In the above-mentioned reaction, the compound [a-2] can be used in an amount of 1 to 5 moles, preferably 2 to 3 moles per one mole of the compound [II-A]. The base and water can be used in an amount of 1 to 5 moles, preferably 2 to 3 moles per one mole of the compound [II-A]. The reaction can be carried out at −78° C. to 30° C., preferably −78° C. to room temperature.

Furthermore, among the compounds [I], a compound in which $R^1$ is a group of the formula: $R^aSO_2NH-CH_2-$ (compound [I-A3]) can be prepared by removing an aminoprotecting group ($G^1$) in a conventional manner from a compound of the following formula [II-A3]:

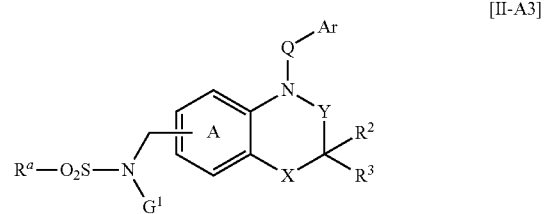

wherein the symbols are the same as defined above.

Method B:

Among the compounds [I] of the present invention, a compound in which $R^1$ is a group of the formula: $(R^b)(R^c)NSO_2-$ (compound [I-B]) can be prepared by reacting a sulfonylhalide compound of the formula [II-B]:

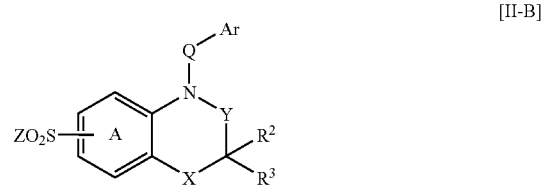

wherein Z is a halogen atom and the other symbols are the same as defined above with an amine compound of the formula [b]:

wherein the symbols are the same as defined above.

Examples of the halogen atom in the compound [II-B] include chlorine atom, bromine atom and the like. The reaction of the compound [II-B] with the compound [b] can be carried out in the same manner as exemplified in the reaction of the compound [II-A] with the compound [a] mentioned above.

Method C:

Among the compounds [I] of the present invention, a compound in which Y is a group of the formula: —C(=S)—, namely a compound of the formula [I-C]:

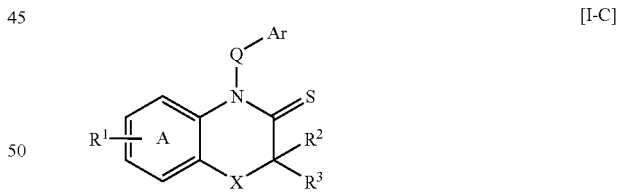

wherein the symbols are the same as defined above, can be also prepared by reacting a corresponding compound [I] in which Y is a group of the formula: —C(=O)—, namely a compound of the formula [I-D]:

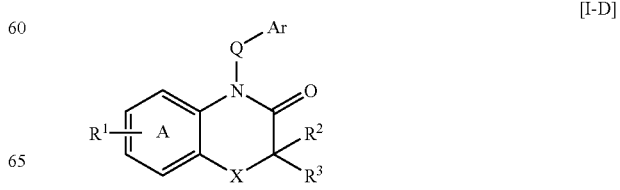

wherein the symbols are the same as defined above with a thionation reagent (e.g., diphosphorus pentasulfide, bis(trimethylsilyl)sulfide, Lawesson's reagent and the like) in a solvent. Examples of the solvent include any inert solvent which does not disturb the reaction, such as an ether mentioned above and the like and among them, dioxane or tetrahydrofuran is preferable. In the present reaction, the thionation reagent can be used in an amount of 0.5 to 5 moles, preferably 0.5 to 2 moles per one mole of the compound [I-D]. The reaction can be carried out at room temperature to 120° C., preferably at room temperature to 60° C.

Method D:

Among the compounds [I] of the present invention, a compound in which X is a group of the formula: —CH$_2$— and Y is a group of the formula: —C(=O)—, namely a compound of the formula [I-E]:

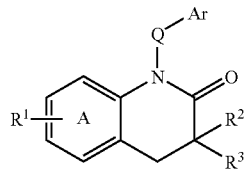

[I-E]

wherein the symbols are the same as defined above, can be also prepared by reducing a compound of the following formula [II-E]:

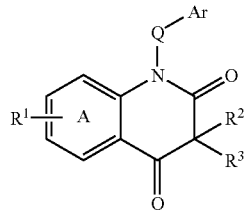

[II-E]

wherein the symbols are the same as defined above.

The present reaction can be conducted in a solvent in the presence of a reducing agent. Examples of the solvent include any inert solvent which does not disturb the reaction, such as a halogenated hydrocarbon including chloroform and the like, an organic acid including trifluoroacetic acid and the like, boron trifluoride-ether complex and a mixture thereof. The reducing agent may be triethylsilane and the like. In the present reaction, the reducing agent can be used in an amount of 3 to 30 moles, preferably 5 to 20 moles per one mole of the compound [I-E]. The reaction can be carried out under ice-cooling to 100° C., preferably at 50° C. to 60° C.

The objective compound [I] of the present invention can be also prepared by further converting the substituent(s) in R$^1$ or Ar of the compound [I] as obtained in Methods (A) to (D) mentioned above to the other desired substituent(s). The further conversion process can be selected according to the kinds of the objective substituent(s), and may be carried out, for example, in the following methods.

Method (a): A compound [I] having a mono- or di-alkylamino group (or a mono- or di-alkylamino-containing group) can be prepared by:

(i) reacting a corresponding compound [I] having as a substituent(s) a primary or secondary amino group (or a primary or secondary amino-containing group) with a desired alkylhalide in an appropriate solvent in the presence of a base, or (ii) reacting a corresponding compound [I] having as a substituent(s) a halogen atom (or a halogen-containing group) with a mono- or di-alkylamine in a solvent in the presence or absence of a catalyst (e.g., a palladium catalyst such as palladium acetate), an additive (e.g., a phosphine compound such as triphenylphosphine) and a base (e.g., an alkali metal carbonate such as potassium carbonate), or (iii) reacting a corresponding compound [I] having as a substituent(s) a primary or secondary amino group (or a primary or secondary amino-containing group) with an aldehyde compound (e.g., formaldehyde) in the presence of a reducing agent (e.g., sodium borohydride).

Method (b): A compound [I] having an acylamino group (or an acylamino-containing group) can be prepared by:

(i) reacting a corresponding compound [I] having as a substituent(s) a halogen atom (or a halogen-containing group) with an amide compound of the formula [c]:

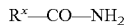

R$^x$—CO—NH$_2$    [c]

wherein the symbol is the same as defined above in the same manner as described in Method (a)-(ii) mentioned above or (ii) a corresponding compound [I] having as a substituent(s) an amino group (or an amino-containing group) with an acylating agent of the formula [c-1]:

R$^x$—CO-Hal    [c-1]

wherein the symbol is the same as defined above in the presence of a base (e.g., pyridine).

Method (c): A compound [I] having as a substituent(s) a hydroxyl group (or a hydroxyl-containing group) can be prepared by (i) treating (dealkylating) a corresponding compound [I] having as a substituent(s) an alkoxy group (or an alkoxy-containing group) in a solvent with boron tribromide and the like, or (ii) hydrolyzing a corresponding compound [I] having as a substituent(s) an acyloxy group such as a benzoyloxy group in the presence of a base (e.g., sodium hydroxide).

Method (d): A compound [I] having as a substituent(s) an alkoxy group (or an alkoxy-containing group) can be prepared by:

(i) reacting a corresponding compound [I] having as a substituent(s) a hydroxyl group (or a hydroxyl-containing group) with an alkylhalide in an appropriate solvent, or (ii) reacting a corresponding compound [I] having as a substituent(s) a hydroxyl group (or a hydroxyl-containing group) with an alkanol in an appropriate solvent in the presence or absence of a base (e.g., an alkali metal carbonate such as potassium carbonate) and in the presence of an activating agent (e.g., diethyl azodicarboxylate) and a tri-substituted phosphine compound, or (iii) reacting a corresponding compound [I] having as a substituent(s) a halogen atom (or a halogen-containing group) with an alkanol in an appropriate solvent in the presence of a catalyst (e.g., a palladium catalyst such as palladium acetate) and in the presence or absence of an additive (e.g., a phosphine compound such as triphenyl phosphine, racemic 2-(di-tert-butylphosphino)-1,1'-binaphthyl) and a base (e.g., an alkali metal carbonate such as potassium carbonate, cesium carbonate).

Method (e): A compound [I] having as a substituent(s) a methyl group can be prepared by reacting a corresponding compound [I] having as a substituent(s) a halogen atom with a trimethylboroxin in a solvent in the presence of a palladium catalyst (e.g., [1,1-bis(triphenylphosphino)ferrocene]dichloropalladium (II), tetrakis(triphenylphosphin)-palladium(0)) and in the presence or absence of a base (e.g., potassium carbonate).

Method (f): A compound [I] having as a substituent(s) a hydroxyalkyl group (or a methyl-containing group) can be prepared by hydrolyzing a corresponding compound [I] having as a substituent(s) an acyloxyalkyl group in a solvent (e.g., methanol, tetrahydrofuran) with a base (e.g., sodium hydroxide). Besides, the compound [I] having as a substituent(s) a hydroxymethyl group can be also prepared by reacting a corresponding compound [I] having as a substituent(s) a vinyl group with ozone and then treating the reaction product with a reducing agent (e.g., sodium borohydride). The compound [I] having as a substituent(s) a hydroxyethyl group can be also prepared by treating a corresponding compound [I] having as a substituent(s) a vinyl group with a borane reagent (e.g., borane-dimethylsulfide complex) and treating the reaction product with an aqueous hydrogen peroxide solution.

Method (g): A compound [I] having as a substituent(s) an amino group can be prepared by subjecting a corresponding compound [I] having as a substituent(s) a nitro group to a catalytic reduction with a palladium catalyst and the like.

Method (h): A compound [I] having as a substituent(s) an ethyl group can be prepared by subjecting a corresponding compound [I] having as a substituent(s) a vinyl group to a catalytic hydrogenation in the presence of a palladium catalyst (e.g., palladium-carbon) and the like.

Method (i): A compound [I] having as a substituent(s) a cyano group can be prepared by reacting a corresponding compound [I] having as a substituent(s) a halogen atom with zinc cyanide in the presence of a palladium catalyst (e.g., tetrakis(triphenylphosphine)palladium(0)) and the like.

Method (j): A compound [I] having as a substituent(s) a cycloalkyl group can be prepared by reacting a corresponding compound [I] having as a substituent(s) a halogen atom with a cycloalkylboronic acid in the presence of a palladium catalyst (e.g., tetrakis(triphenylphosphine)palladium(0)) and a base (e.g., potassium phosphate).

Method (k): A compound [I] having as a substituent(s) a trifluoromethyl group can be prepared by reacting a corresponding compound [I] having as a substituent(s) an iodine atom with ethyl 2,2-difluoro-2-(fluorosulfonyl)acetate in the presence of a copper salt (e.g., copper(I) bromide). Meanwhile, the compound [I] having as a substituent(s) an iodine atom can be prepared by treating a corresponding compound [I] with an iodination agent (e.g., bis(pyridine)iodonium tetrafluoroborate).

If necessary, the objective compound [I] of the present invention can be converted to a pharmaceutically acceptable salt and the conversion to said salt may be conducted by a conventional manner.

The synthetic intermediate of the present invention, the compound [II-A] and the compound [II-B], can be prepared by, for example, the following manners.

Among the intermediate compounds [II-A], a compound in which X is an oxygen atom or a sulfur atom and Y is a group of the formula: —C(=O)—, namely a compound of the following formula [II-a]:

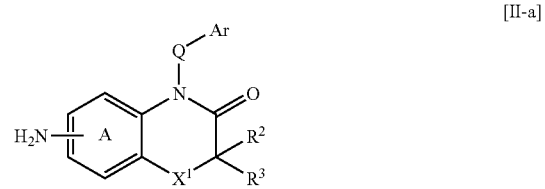

[II-a]

wherein $X^1$ is an oxygen atom or a sulfur atom and the other symbols are the same as defined above can be prepared in accordance with a manner as illustrated in the following reaction scheme A.

Reaction Scheme A1:

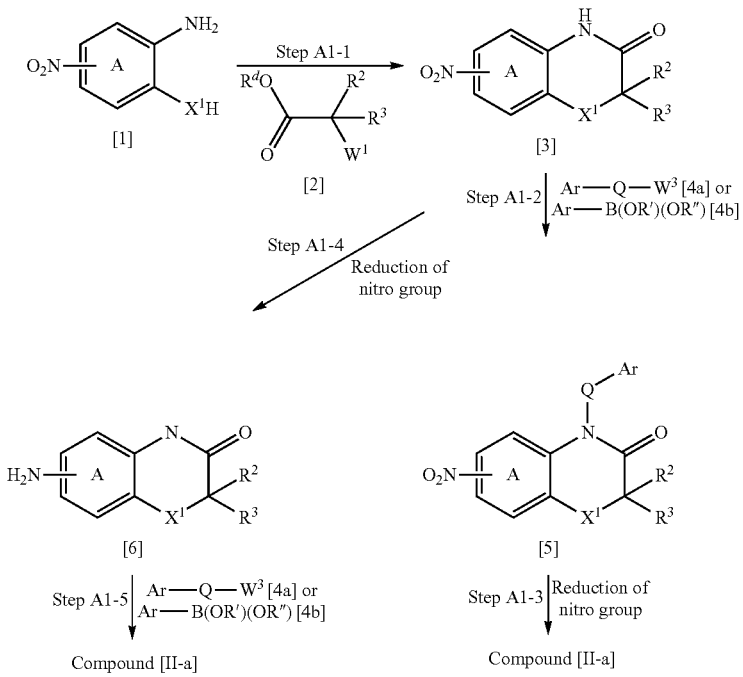

In the reaction scheme mentioned above, $R^d$ is a hydrogen atom or an alkyl group, R' and R" are a hydrogen atom or an alkyl group or both of them combine each other at their termini to form an alkylene group, $W^1$ and $W^3$ are a halogen atom and the other symbols are the same as defined above.

Step A1-1:

The reaction of the compound [1] with the compound [2] can be carried out in a solvent in the presence of a base. Examples of $W^1$ in the compound [2] include bromine atom, chlorine atom and the like, and examples of $R^d$ include a hydrogen atom or an alkyl group such as methyl group, ethyl group and the like. Examples of the solvent include any inert solvent which does not disturb the reaction, such as an halogenated aliphatic hydrocarbon including chloroform, dichloromethane and dichloroethane, an aromatic hydrocarbon including benzene, toluene and xylene, an ether including diethylether, diisopropylether, tetrahydrofuran, dioxane and 1,2-dimethoxyethane, an amide including N,N-dimethylformamide, N,N-dimethylacetamide and 1,3-dimethyl-2-imidazolidinone, a nitrile including acetonitrile, an alcohol including methanol, ethanol, isopropanol, n-butanol and tert-butanol, a ketone including acetone and 2-butanone, dimethylsulfoxide, pyridine, 2.6-lutidine and the like, a mixture thereof, or a combination of water and such solvent. Among these, examples of the preferable solvent include N,N-dimethylformamide, N,N-dimethylacetamide, 1,3-dimethyl-2-imidazolidinone, ethanol, acetone and the like. Examples of the base include an alkali metal fluoride such as potassium fluoride, sodium fluoride and the like, an alkali metal hydride such as sodium hydride and the like, an alkali metal alkoxide such as potassium tert-butoxide and the like, an alkali metal carbonate such as sodium carbonate, potassium carbonate, cesium carbonate and the like, an alkali metal hydroxide such as sodium hydroxide, potassium hydroxide, lithium hydroxide and the like, a trialkylamine such as triethylamine, tributylamine, diisopropylethylamine and the like, and a tertiary cyclic amine such as 1,4-diazabicyclo[2.2.2]octane, 1,5-diazabicyclo[4.3.0]non-5-en, 1,8-diazabicyclo[5.4.0]-undec-7-en and the like.

In the above-mentioned reaction process, the compound [2] can be used in an amount of 1 to 5 moles, preferably 1 to 2 moles per one mole of the compound [1]. The base can be used in an amount of 1 to 5 moles, preferably 1 to 2 moles per one mole of the compound [1]. The reaction can be carried out under cooling to heating, preferably at room temperature to a boiling point of the reaction mixture.

Step A1-2:

(a) The reaction of the compound [3] with the compound [4a] in which Q is a single bond or an alkenylene group can be carried out in a solvent in the presence of a copper salt, a base and an additive. Examples of the solvent include any inert solvent which does not disturb the reaction, such as an aromatic hydrocarbon including benzene, toluene and xylene, an ether including diisopropylether, tetrahydrofuran, dioxane and 1,2-dimethoxyethane, an alcohol including methanol, ethanol, 1-propanol and 2-propanol, an amide including N,N-dimethylformamide, N,N-dimethylacetamide, 1,3-dimethyl-2-imidazolidinone and 1-methyl-2-pyrrolidinone, a nitrile including acetonitrile, dimethylsulfoxide, pyridine, 2.6-lutidine and the like, or a mixture thereof. Among these, examples of the preferable solvent include toluene, xylene, tetrahydrofuran, dioxane, N,N-dimethylformamide, N,N-dimethylacetamide, 1,3-dimethyl-2-imidazolidinone, 1-methyl-2-pyrrolidinone, dimethylsulfoxide and the like. Examples of the copper salt include copper iodide, copper(I) oxide, copper sulfate, copper chloride, copper acetate, copper thiophen-2-carboxylate and the like. Examples of the base include an alkali metal phosphate such as potassium phosphate and the like, an alkali metal carbonate such as sodium carbonate, potassium carbonate, cesium carbonate and the like, an alkali metal acetate such as cesium acetate and the like, an alkali metal fluoride such as potassium fluoride and the like, an alkali metal alkoxide such as sodium tert-butoxide and the like, and an alkali metal hydroxide such as sodium hydroxide and the like. Examples of the additive include a diamine such as N,N'-dimethylethylenediamine, ethylenediamine, N,N'-dimethylcyclohexane-1,2-transdiamine, N,N'-cyclohexane-1,2-transdiamine, o-phenylenediamine and the like, an amino acid such as glycine, N-methylglycine, N,N-dimethylglycine, proline and the like, an aminoalcohol such as prolinol and the like, and 1.10-phenanthroline. In the above-mentioned reaction process, the copper salt can be used in an amount of 0.01 to 3.0 moles, preferably 0.01 to 0.3 moles per one mole of the compound [3]. The base can be used in an amount of 1 to 10 moles, preferably 1 to 2 moles per one mole of the compound [3]. The additive can be used in an amount of 0.01 to 5.0 moles, preferably 0.02 to 0.6 moles per one mole of the compound [3]. The reaction can be carried out at 50 to 250° C., preferably at 80 to 150° C.

(b) The reaction of the compound [3] with the compound [4a] in which Q is an alkylene group can be carried out in a solvent in the presence of a base. Examples of the solvent include any inert solvent which does not disturb the reaction, such as an ether including tetrahydrofuran, dioxane and 1,2-dimethoxyethane, an amide including N,N-dimethylformamide, N,N-dimethylacetamide and 1,3-dimethyl-2-imidazolidinone, dimethylsulfoxide, pyridine, 2.6-lutidine and the like, a mixture thereof, or a combination of water and such solvent. Among these, examples of the preferable solvent include N,N-dimethylformamide, N,N-dimethylacetamide, 1,3-dimethyl-2-imidazolidinone, dimethylsulfoxide and the like. The base may be an alkali metal hydride such as sodium hydride and the like, an alkali metal alkoxide such as potassium tert-butoxide, sodium methoxide and the like, a lithium amide, an alkyl lithium, an alkylmagnesium halide, an alkali metal carbonate such as sodium carbonate, potassium carbonate, cesium carbonate and the like, an alkali metal hydroxide such as sodium hydroxide, potassium hydroxide, lithium hydroxide and the like, a trialkylamine such as triethylamine, tributylamine, diisopropylethylamine and the like, and a tertiary cyclic amine such as 1,4-diazabicyclo[2.2.2]octane, 1,5-diazabicyclo[4.3.0]non-5-en, 1,8-diazabicyclo[5.4.0]-undec-7-en and the like. In the above-mentioned reaction process, the compound [4a] can be used in an amount of 1 to 5 moles, preferably 1 to 2 moles per one mole of the compound [3]. The base can be used in an amount of 1 to 5 moles, preferably 1 to 2 moles per one mole of the compound [3]. The reaction can be carried out under cooling to heating, preferably under ice-cooling to a boiling point of the reaction mixture.

(c) The reaction of the compound [3] with the arylboronic acid compound [4b] can be carried out in a solvent in the presence of a catalyst and a base and in the presence or absence of an additive. Examples of the boronic acid compound [4b] include those in which R' and R" are a hydrogen atom or an alkyl group such as a methyl group, an ethyl group, a propyl group, a butyl group and the like, or both of them combine each other at their termini to form an alkylene group such as an ethylene group, a propylene group, a 1,1,2,2-tetramethylethylene group and the like, and among them, a compound [4b] in which R' and R" are a hydrogen atom (or a corresponding boroxin compound of the formula: $[ArBO]_3$) is preferable. Examples of the solvent include any inert solvent which does not disturb the reaction, such as a halogenated aliphatic hydrocarbon (e.g., chloroform, dichloromethane, dichloroethane and the like), an ether (e.g., diethylether, diisopropylether, tetrahydrofuran, dioxane, 1,2-dimethoxyethane and the like), an ester (e.g., ethyl acetate and the like), an amide (e.g., N,N-dimethylformamide, N,N-dimethylacetamide, 1,3-dimethyl-2-imidazolidinone and the like), an alcohol (e.g., methanol and the like), dimethylsulfoxide and the like, or a mixture comprising two or more solvent mentioned above, among them, dichloromethane is preferable. The catalyst may be copper(I) acetate, copper(I) chloride and the like, and among them, copper(I) acetate is preferable. Examples of the base include triethylamine, pyridine and the like. The additive may be Molecular sieves-4A, an oxidizing agent (e.g., pyridine N-oxide, 2,2,6,6-tetramethylpiperidine 1-oxyl (TEMPO), 4-methylmorpholine N-oxide) and the like. In the above-mentioned reaction process, the compound [4b] can be used in an amount of 1 to 5 moles, preferably 1 to 2 moles per one mole of the compound [3]. The catalyst can be used in an amount of 0.1 to 2 moles, preferably 1 to 1.5 moles per one mole of the compound [3]. The base can be used in an amount of 0.1 to 5 moles, preferably 1 to 2 moles per one mole of the compound [3]. The additive can be used in an amount of 0 to 1.5 moles per one mole of the compound [3]. The reaction can be carried out at room temperature to a temperature under heating, preferably at room temperature.

Step A1-3:

The reduction of nitro group in the compound [5] can be carried out in a solvent in the presence of a reducing agent. Examples of the solvent include any inert solvent which does not disturb the reaction, such as water, an alcohol including methanol, ethanol, and propanol, an ester including ethyl acetate, an amide including N,N-dimethylformamide, N,N-dimethylacetamide and 1,3-dimethyl-2-imidazolidinone, a nitrile including acetonitrile, an ether including tetrahydrofuran, dioxane and 1,2-dimethoxy-ethane, a mixture thereof, or a combination of water and such solvent. Among them, ethyl acetate, ethanol or a mixture of water and such solvent is preferable. The reducing agent may be a metal such as tin, iron or zinc, or a metal salt such as tin chloride and the like. Meanwhile, depending on the kind of the reducing agent, a mineral acid such as hydrochloric acid or ammonium chloride may be added to the reaction system. In the above-mentioned reaction process, the reducing agent can be used in an amount of 1 to 5 moles, preferably 1 to 2 moles per one mole of the compound [5]. The reaction can be carried out under cooling to heating, preferably at room temperature to a boiling point of the reaction mixture.

Besides, the reduction of the compound [5] can be carried out by hydrogenating it in a solvent in the presence of a metal catalyst. Examples of the solvent include any inert solvent which does not disturb the reaction, such as an alcohol, an ether, a halogenated aliphatic hydrocarbon, an aromatic hydrocarbon, an amide or an ester mentioned above, or an organic acid such as formic acid, acetic acid, propionic acid or trifluoroacetic acid, or a mixture thereof. The metal catalyst may be palladium carbon, Raney-nickel, Raney-cobalt, platinum oxide and the like. Meanwhile, depending the kind of the reducing agent, a mineral acid such as hydrochloric acid may be added to the reaction system. The reaction can be carried out under cooling to heating, preferably at $-10°$ C. to a boiling point of the reaction mixture.

Step A1-4:

The reduction of nitro group in the compound [3] can be carried out in the same manner as described in Step A1-3.

Step A1-5:

The reaction of the compound [6] with the compound [4a] or the compound [4b] can be carried out in the same manner as described in Step A1-2, respectively.

Meanwhile, the compound [3] can be also prepared by treating a compound of the formula [1a]:

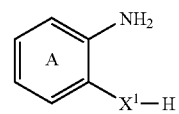

[1a]

wherein the symbols are the same as defined above and a compound [2] in the same manner as described in the above reaction step A1-1 to give a compound of the formula [3a]:

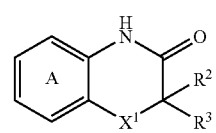

[3a]

wherein the symbols are the same as defined above and then treating said product [3a] in a solvent (e.g., acetic acid) with nitric acid.

Moreover, among the compound [3], a compound of the following formula [31]:

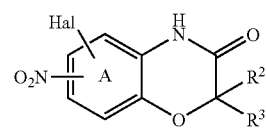

[31]

wherein Hal is a halogen atom and the other symbols are the same as defined above can be also prepared in a manner as illustrated in the following reaction scheme A2

Reaction Scheme A2:

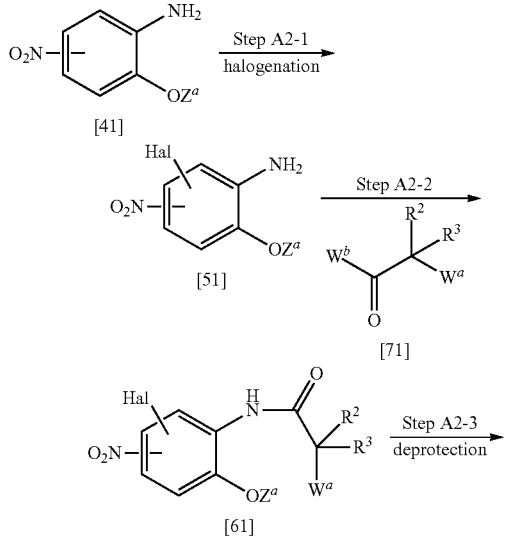

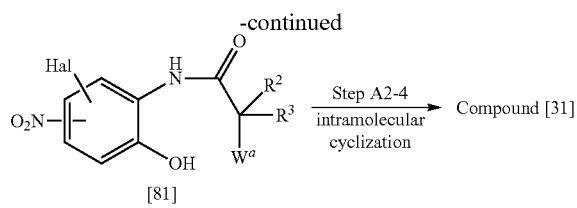

In the above reaction scheme, $OZ^a$ is a protected hydroxyl group, $W^a$ and $W^b$ are a halogen atom and the other symbols are the same as defined above.

Step A2-1

The halogenation of the compound [41] can be carried out in a solvent in the presence of a halogenating agent. Examples of the solvent include any inert solvent which does not disturb the reaction, such as an aliphatic hydrocarbon including chloroform, an amide including N,N-dimethylformamide and the like. The halogenating agent may be N-bromosuccinimide, N-chlorosuccinimide, bromine and the like. In the present reaction, the halogenating agent can be used in an amount of 1 to 1.5 moles, preferably 1 to 1.1 moles per one mole of the compound [41]. The reaction can be carried out at 0° C. to 30° C., preferably at 0° C. to 5° C.

Step A2-2

The reaction of the compound [51] and the compound [71] can be carried out in a solvent in the presence of a base. Examples of the solvent include any inert solvent which does not disturb the reaction, such as an aliphatic hydrocarbon including chloroform, an ether including tetrahydrofuran and the like. The base may be an amine including pyridine, a tertiary amine including triethylamine and the like. In the present reaction, the compound [71] can be used in an amount of 1 to 5 moles, preferably 1 to 2 moles per one mole of the compound [51]. The base can be used in an amount of 2 to 3 moles per one mole of the compound [51], preferably equimolar of the compound [71]. The reaction can be carried out at 0° C. to 30° C., preferably at 15° C. to 25° C.

Step A2-3

The removal of the protecting group $Z^a$ from the compound [61] can be carried out in a conventional manner. For example, in case that the protecting group $Z^a$ is an alkoxyalkyl group such as a methoxymethyl group and the like, said protecting group can be removed by treating the compound [61] with an acid (e.g., hydrochloric acid, trifluoroacetic acid) in a solvent (e.g., dichloromethane, water, tetrahydrofuran, dioxane).

Step A2-4

The intramolecular cyclization of the compound [81] can be carried out in a solvent in the presence of a base. Examples of the solvent include any inert solvent which does not disturb the reaction, such as an amide including N,N-dimethylformamide, a ketone including acetone and the like. The base may be an alkali metal carbonate including potassium carbonate, sodium hydride and the like. In the present reaction, the base can be used in an amount of 1 to 3 moles, preferably 2 to 3 moles per one mole of the compound [81]. The reaction can be carried out at 30° C. to 60° C., preferably at 50° C. to 60° C.

Meanwhile, the intermediate compound [5] can be prepared in a manner as illustrated in the following reaction scheme A3.

Reaction Scheme A3:

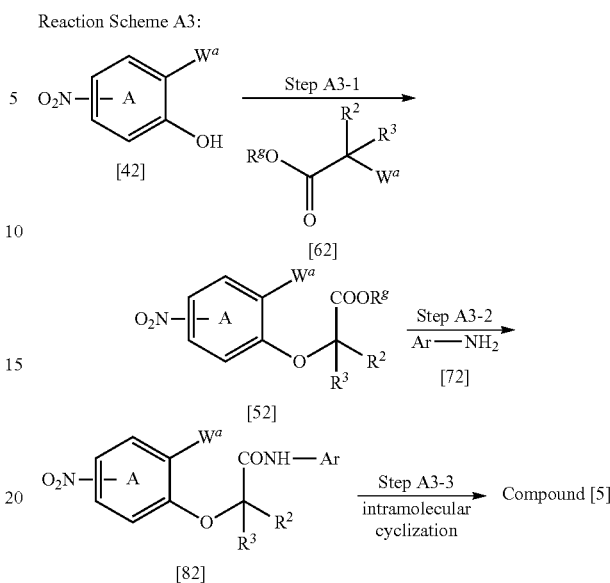

In the above reaction scheme, $R^g$ is an alkyl group and the other symbols are the same as defined above.

Step A3-1:

The reaction of the compound [42] with the compound [62] can be carried out in a solvent in the presence of a base. Examples of the solvent include any inert solvent which does not disturb the reaction, such as an amide including N,N-dimethylformamide, a ketone including acetone, a nitrile including acetonitrile and the like. The base may be an alkali metal carbonate including potassium carbonate, cesium carbonate, sodium hydride and the like. In the present reaction, the compound [62] can be used in an amount of 1 to 4 moles, preferably 1 to 1.2 moles per one mole of the compound [42]. The base can be used in an amount of 1 to 2 moles, preferably 1 to 1.3 moles per one mole of the compound [42]. The reaction can be carried out at room temperature to 60° C., preferably at room temperature.

Step A3-2:

The reaction of the compound [52] with the compound [72] can be carried out in a solvent in the presence of an activating agent for amidation. Examples of the solvent include any inert solvent which does not disturb the reaction, such as dichloromethane, chloroform and the like. The activating agent for amidation may be a trialkylaluminum such as trimethylaluminum and the like. In the present reaction, the compound [72] can be used in an amount of 1 to 6 moles, preferably 1 to 4 moles per one mole of the compound [52]. The activating agent for amidation can be used in an amount of 1 to 6 moles, preferably 1 to 4 moles per one mole of the compound [52]. The reaction can be carried out at room temperature to 70° C., preferably at room temperature to 40° C.

Meanwhile, the compound [82] can be prepared by subjecting the compound [52] to a conventional hydrolysis to give a corresponding carboxylic acid compound and then reacting said carboxylic acid compound or a reactive derivative thereof (e.g., a corresponding acid halide) with the compound [72] in a solvent (e.g., tetrahydrofuran) in the presence of a base (e.g., n-butyl lithium, lithium bis(trimethylsilyl) amide, pyridine).

Step A3-3:

The intramolecular cyclization of the compound [82] can be carried out in a solvent in the presence or absence of copper salt and in the presence of a base. Examples of the solvent include any inert solvent which does not disturb the reaction, such as an amine including pyridine, an amide including N,N-dimethylformamide, dimethylsulfoxide and the like. The copper salt may be copper(I) iodide, copper(I) bromide, copper(I) chloride and the like. The base may be an alkali metal phosphate such as potassium phosphate, an alkali metal carbonate such as potassium carbonate, sodium carbonate, cesium carbonate and the like, sodium hydride, potassium tert-butoxide and the like. In the present reaction, the copper salt can be used in an amount of 0 to 10 moles, preferably 0 to 4 moles per one mole of the compound [82]. The base can be used in an amount of 1 to 3 moles, preferably 1 to 1.5 moles per one mole of the compound [82]. The reaction can be carried out at room temperature ° C. to 150° C., preferably at a boiling point of the reaction mixture.

Among the intermediate compounds [II-a], a compound of the following formula [II-a2]:

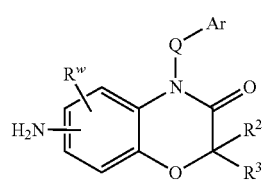

[II-a2]

wherein $R^W$ is an alkenyl group optionally substituted by an alkoxy group or an alkanoyl group and the other symbols are the same as defined above can be prepared by reacting the compound of the following formula [5a].

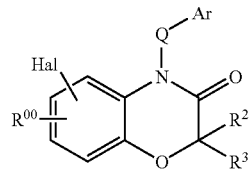

[5a]

wherein $R^{00}$ is an amino group or a nitro group and the other symbols are the same as defined above with a trialkyltin compound of the following formula [x]:

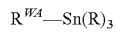  $R^{WA}$—Sn(R)$_3$     [x]

wherein $R^{WA}$ is an alkenyl group optionally substituted by an alkoxy group and R is an alkyl group in a solvent (e.g., dioxane, toluene) in the presence of a catalyst (e.g., a palladium catalyst such as dichlorobis(triphenylphosphine)palladium(II), tetrakis(triphenylphosphine)paladium(0)) followed by treating said product with a reducing agent in case that $R^{00}$ of the product is a nitro group, and if required, hydrolyzing the product in the presence of an acid (e.g., hydrochloric acid).

Furthermore, the compound [II-a] can be also prepared in accordance with the manner as described in the following reaction scheme B1.

Reaction Scheme B1:

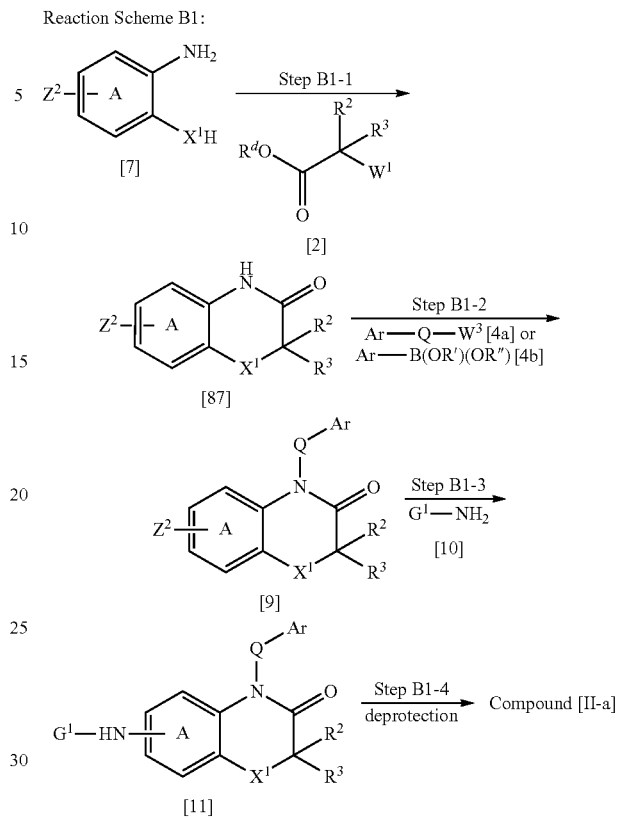

In the above reaction scheme, $Z^2$ is a removing group, $G^1$ is an amino-protecting group, and the other symbols are the same as defined above.

Step B1-1:

Examples of the removing group ($Z^2$) in the compound [7] include a halogen atom such as chlorine atom, iodine atom, bromine atom and the like, trifluoromethanesulfonyloxy group, p-toluenesulfonyloxy group and p-toluenesulfonyloxy group. The present reaction step can be carried out in the same manner as described in the above-mentioned Step A1-1.

Meanwhile, among the compounds [8], a compound of the formula [83]:

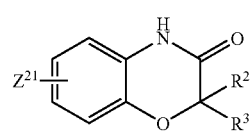

[83]

wherein $Z^{21}$ is a halogen atom and the other symbols are the same as defined above can be prepared by reacting a compound of the formula [43]:

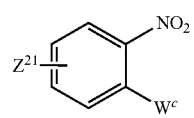

[43]

wherein $W^c$ is a halogen atom and the other symbol is the same as defined above with a compound of the formula [53]:

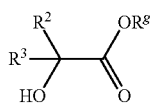

wherein the symbols are the same as defined above in a solvent (e.g., tetrahydrofuran) in the presence of a base (e.g., sodium hydride) to give a compound of the formula [63]:

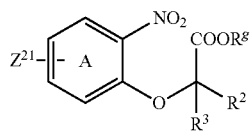

wherein the symbols are the same as defined above and then subjecting said product [63] to intramolecular cyclization in a solvent (e.g., ethyl acetate) in the presence of a reducing agent (e.g., tin(II) chloride).

Step B1-2:

The present reaction step can be carried out in the same manner as described in the above-mentioned Step A1-2.

Step B1-3:

Examples of the amino-protecting group ($G^1$) in the compound [10] include an aralkyloxycarbonyl group such as benzyloxycarbonyl group, an alkoxycarbonyl group such as tert-butoxycarbonyl group and the like. The reaction of the compound [9] with the compound [10] can be carried out in a solvent in the presence of a base and a transition metal catalyst. Examples of the solvent include any inert solvent which does not disturb the reaction, such as an alcohol, an aromatic hydrocarbon or dioxane, and among them, tert-butanol, toluene, xylene or dioxane is preferable. Examples of the base include those mentioned above such as an alkali metal carbonate, an alkali metal phosphate and an alkali metal phenoxide, and among them, potassium carbonate, cesium carbonate, potassium phosphate or sodium phenoxide and the like is preferable. The transition metal catalyst may be those mentioned above such as a palladium catalyst and among them, palladium acetate, tri(dibenzylideneacetone)dipalladium, dichlorobis(triphenylphosphine)palladium and the like is preferable. Meanwhile, if necessary, a ligand such as a phosphine compound (e.g., triphenylphosphine, 2-dicyclohexylphosphino-2',4',6'-triisopropyl-1,1'-biphenyl, tri-tert-butylphosphine and the like) and an activating agent such as an arylboronic acid compound (e.g., phenylboronic acid and the like) can be used in the present reaction. In the above reaction process, the compound [10] can be used in an amount of 1 to 10 moles, preferably 1 to 3 moles per one mole of the compound [9]. The base can be used in an amount of 1 to 10 moles, preferably 1 to 3 moles per one mole of the compound [9]. The transition metal catalyst (or the ligand) can be used in an amount of 0.01 to 0.5 mole, preferably 0.01 to 0.2 mole per one mole of the compound [9]. The activating agent can be used in an amount of 0.005 to 0.3 mole per one mole, preferably 0.005 to 0.05 mole per one mole of the compound [9]. The reaction can be carried out at 60 to 150° C., preferably at 80 to 120° C.

Step B1-4:

The present reaction step can be carried out depending on the kinds of the protecting group ($G^1$) by, for example, treatment with an acid or a base. Instantly, when $G^1$ is tert-butoxycarbonyl group, the removal of said protecting group can be carried out by treating the compound [11] with an acid (e.g., hydrochloric acid, trifluoroacetic acid) in a solvent. Examples of the solvent include any inert solvent which does not disturb the reaction mentioned above, such as an alcohol, a halogenated aliphatic hydrocarbon, an ester, an ether or an organic acid, or a mixture thereof. The reaction can be carried out under cooling to heating, preferably under ice-cooling to room temperature.

Among the intermediate compounds [II-A], a compound in which X is oxygen atom or sulfur atom and Y is a group of the formula: —$CH_2$—, namely a compound of the following formula [II-b]:

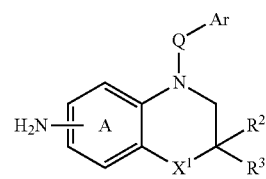

wherein the symbols are the same as defined above can be prepared by, for example, (i) subjecting the compound [II-a] to reducing reaction of 3-carbonyl group, or (ii) subjecting the compound [5] to reducing reaction of 3-carbonyl group followed by treating the product in the same manner as described in Step A1-3 to reduce the nitro group in Ring A.

The reduction of the 3-carbonyl group in the compound [II-a] or the compound [5] can be carried out in a solvent in the presence of a reducing agent. Examples of the solvent include any inert solvent which does not disturb the reaction mentioned above, such as an ether. The reducing agent may be borane-dimethylsulfide complex, diborane, borane-tetrahydrofuran complex, borane-1,4-oxathian complex, borane-dimethylanilline complex, borane-4-methylmorpholine complex, lithium aluminum hydride and the like. The reducing agent can be used in an amount of 0.5 to 5 moles, preferably 1 to 3 moles per one mole of the compound [II-a] or the compound [5]. The reaction can be carried out under cooling to heating, preferably at −10° C. to a boiling point of the reaction mixture.

Among the intermediate compounds [II-A], a compound in which X is oxygen atom or sulfur atom and Y is a group of the formula: —CH($R^5$)—, $R^5$ is an alkyl group or an optionally substituted aryl group and Q is a single bond or an alkenylene group, namely a compound of the following formula [II-c]:

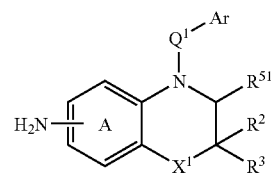

wherein $R^{51}$ is an alkyl group or an optionally substituted aryl group, $Q^1$ is a single bond or an alkenylene group and the other symbols are the same as defined above, can be prepared, for example, by (i) reacting the above compound [1] with a compound of the formula [12]:

[12]

wherein the symbols are the same as defined above under the same condition as described in the above Step A1-1 to give a compound of the formula [13]:

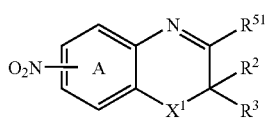
[13]

wherein the symbols are the same as defined above, (ii) reducing the compound [13] to give a compound of the formula [14]:

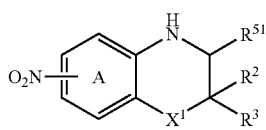
[14]

wherein the symbols are the same as defined above, (iii) reacting the compound [14] with a compound of the formula [4aa]:

[4aa]

wherein $Z^a$ is a halogen atom and the other symbols are the same as defined above to give a compound of the formula [15]:

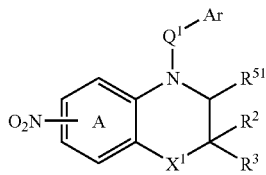
[15]

wherein the symbols are the same as defined above, and (iv) treating the compound [15] in the same manner as described in the above Step A1-3.

The reduction of the cyclic imine compound [13] can be carried out in a solvent in the presence of a reducing agent. Examples of the solvent include any inert solvent which does not disturb the reaction mentioned above, such as a halogenated aliphatic hydrocarbon, an ether, an ester, an amide, an alcohol, water or a mixture thereof. Among them, dichloromethane, dichloroethane, tetrahydrofuran, 1,2-dimethoxyethane, methanol, ethanol or propanol is preferable. The reducing agent may be a metal hydride such as sodium borohydride, sodium triacetoxyborohydride, sodium cyanoborohydride and the like. The reducing agent can be used in an amount of 0.5 to 5 moles, preferably 0.5 to 1 mole per one mole of the compound [13]. The reaction can be carried out under cooling to heating, preferably under ice-cooling to room temperature. Besides, the compound [14] can be also prepared by subjecting the compound [13] to catalytic hydrogenation in the presence of a transition metal catalyst. Such transition metal catalyst may be palladium-carbon, platinum-carbon, platinum oxide, Raney-nickel and the like.

The reaction of the compound [14] with the compound [4aa] can be carried out in a solvent in the presence of a base and a transition metal catalyst. Examples of the solvent include any inert solvent which does not disturb the reaction mentioned above, such as an aromatic hydrocarbon, an alcohol, an ether, an amide, dimethylsulfoxide or a mixture thereof. Among them, toluene or tert-butanol is preferable. The base may be that mentioned above such as an alkali metal carbonate, as alkali metal phosphate, an alkali metal alkoxide and the like. Among them, cesium carbonate is preferable. The transition metal catalyst may be palladium acetate, tris(dibenzylideneacetone)dipalladium, dichlorobis(triphenylphosphine)palladium and the like. If required, a ligand such as a phosphine compound (e.g., triphenylphosphine, 2-dicyclohexylphosphino-2',4',6'-triisopropyl-1,1'-biphenyl and the like) can be added to the reaction system. In the above-mentioned reaction process, the compound [4aa] can be used in an amount of 1 to 2 moles, preferably 1 to 1.5 moles per one mole of the compound [14]. The base can be used in an amount of 1 to 2 moles, preferably 1 to 1.5 moles per one mole of the compound [14]. The transition metal catalyst or the ligand can be used in an amount of 0.001 to 0.1 mole, preferably 0.005 to 0.01 mole per one mole of the compound [14]. The reaction can be carried out at room temperature to under heating, preferably under heating.

Among the intermediate compounds [II-A], a compound in which X is a group of the formula: —N(R$^4$)— and Y is a group of the formula: —C(=O)—, namely a compound of the formula [II-e]:

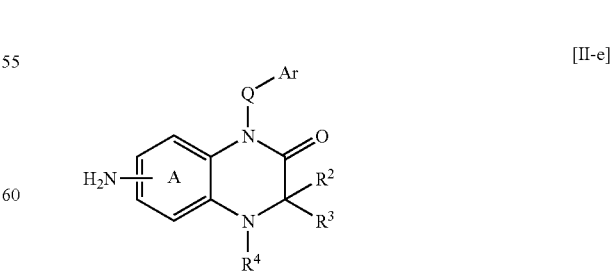
[II-e]

wherein the symbols are the same as defined above can be prepared in accordance with the manner as described in the following reaction scheme C.

Reaction Scheme C1:

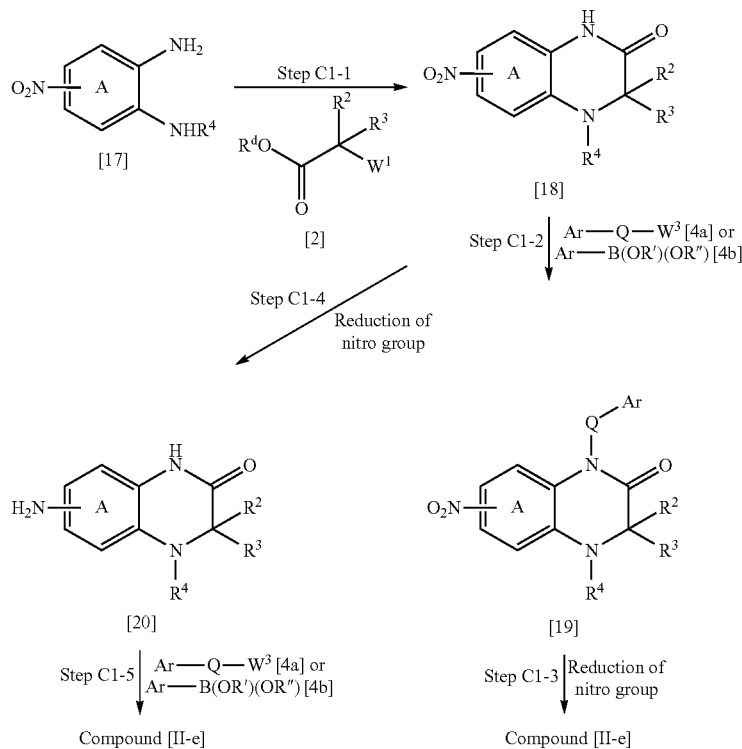

In the above reaction scheme, the symbols are the same as defined above.

Step C1-1:

The reaction of the compound [17] with the compound [2] can be carried out in the same manner as described in the above-mentioned Step A1-1. Besides, the compound [18] can be also prepared by treating a compound of the formula [17a]:

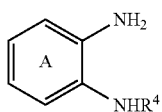

wherein the symbols are the same as defined above and the compound [2] in the same manner as described in the above reaction step A1-1 to obtain a compound of the formula [18a]:

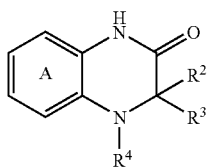

wherein the symbols are the same as defined above, and then treating the compound [18a] with nitric acid in a solvent (e.g., concentrated sulfuric acid).

Step C1-2:

The reaction of the compound [18] with the compound [4a] or the compound [4b] can be carried out in the same manner as described in the above-mentioned Step A1-2.

Step C1-3:

The reduction of the compound [19] can be carried out in the same manner as described in the above-mentioned Step A1-3.

Step C1-4:

The reduction of the compound [18] can be carried out in the same manner as described in the above-mentioned Step A1-3.

Step C1-5:

The reaction of the compound [20] with the compound [4a] or the compound [4b] can be carried out in the same manner as described in the above-mentioned Step A1-2.

Among the intermediate compounds [II-A], a compound in which Y is a group of the formula: —C(=S)—, namely a compound of the formula [II-f]:

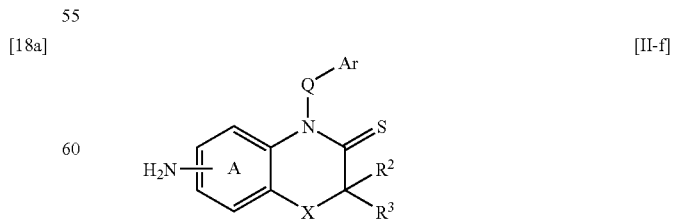

wherein the symbols are the same as defined above, can be prepared by, for example, reacting a compound of the following formula [II-g]:

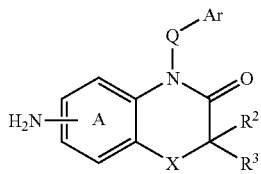

[II-g]

wherein the symbols are the same as defined above with a thionation agent in the same manner as described in Method C.

The intermediate compound of the following formula [II-A3]:

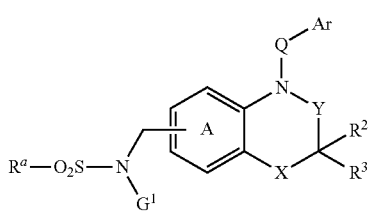

[II-A3]

wherein the symbols are the same as defined above can be prepared in a manner as described in the following reaction scheme D1.

Reaction Scheme D1:

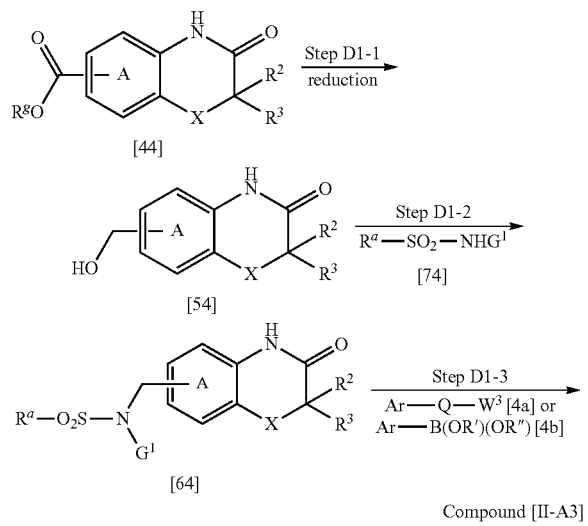

In the above reaction scheme, the symbols are the same as defined above.

Step D1-1:

The reduction of the compound [44] can be carried out in a solvent in the presence of a reducing agent. Examples of the solvent include any inert solvent which does not disturb the reaction mentioned above, such as an ether including tetrahydrofuran and the like. The reducing agent may be diisobutylaluminum hydride and the like. The reducing agent can be used in an amount of 2 to 7 moles, preferably 4 to 5 moles per one mole of the compound [44]. The reaction can be carried out at −78° C. to 0° C., preferably at −78° C. to −50° C.

Step D1-2:

The reaction of the compound [54] with the compound [74] can be carried out in a solvent in the presence of an activating reagent. Examples of the solvent include any inert solvent which does not disturb the reaction mentioned above, such as an aromatic hydrocarbon including toluene, an ether including tetrahydrofuran and the like. The activating reagent may be cyanomethylene tri-n-butylphospholane, cyanomethylene trimethylphospholane and the like. In the present reaction, the compound [74] can be used in an amount of 1 to 5 moles, preferably 1.5 to 2 moles per one mole of the compound [54]. The activating reagent can be used in an amount of 1 to 5 moles, preferably 1.5 to 2 moles per one mole of the compound [54]. The reaction can be carried out at room temperature to 100° C., preferably at 50° C. to 80° C.

Step D1-3:

The reaction of the compound [64] with the compound [4a] or the compound [4b] can be conducted in the same manner as described in the above step A1-2.

The intermediate compound [II-E] of the present invention can be prepared in a manner as described in the following reaction scheme E1.

Reaction Scheme E1:

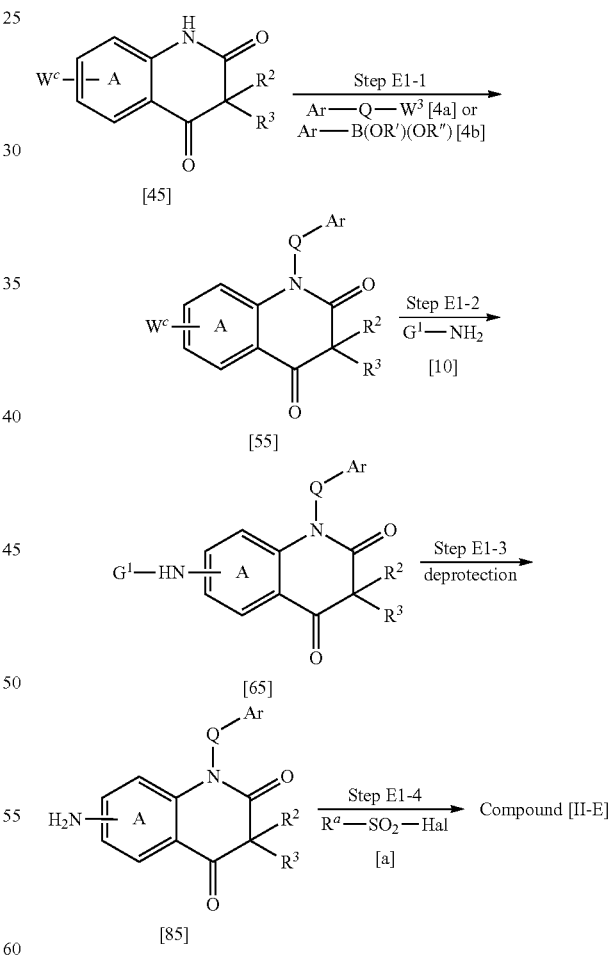

In the above reaction scheme, the symbols are the same as defined above.

Step E1-1:

The reaction of the compound [45] with the compound [4a] or the compound [4b] can be conducted in the same manner as described in the above step A1-2.

Step E1-2:

The reaction of the compound [55] with the compound [10] can be conducted in the same manner as described in the above step B1-3.

Step E1-3:

The removal of the protecting group from the compound [65] can be conducted in the same manner as described in the above step B1-4.

Step E1-4:

The reaction of the compound [85] with the compound [a] can be conducted in the same manner as described in the above Method A.

The intermediate compound [II-B] in the present invention can be prepared by, for example, (i) treating the above compound [II-A] with a diazotizing agent (e.g., a nitrite salt such as sodium nitrite, potassium nitrite) in a hydrogen halide solution (e.g., hydrochloric acid) to obtain a corresponding diazonium salt, and then (ii) reacting (sulfonylating) said diazonium salt with sulfur dioxide or a hydrogen sulfite salt (e.g., sodium hydrogen sulfite, potassium hydrogen sulfite) in a solvent in the presence of copper or its salt (e.g., copper(II) chloride, copper sulfate).

Examples of the solvent used in the above diazotization (i) include any inert solvent which does not disturb the reaction, such as acetic acid, hydrochloric acid, sulfuric acid or a mixture of water and such solvent. The diazotizing agent can be used in an amount of 1 to 5 moles, preferably 1 to 2 moles per one mole of the compound [II-A]. The reaction can be carried out under cooling to under heating, preferably under −10° C. to room temperature.

Examples of the solvent used in the above sulfonylation (ii) include any inert solvent which does not disturb the reaction, such as acetic acid, hydrochloric acid, sulfuric acid or a mixture of water and such solvent. The copper or a salt thereof can be used in an amount of 0.1 to 5 moles, preferably 0.1 to 2 moles per one mole of the product in the diazotization. The sulfur dioxide or a hydrogen sulfite salt can be used in an amount of 1 to 20 moles, preferably 1 to 5 moles per one mole of the product in the diazotization. The reaction can be carried out under cooling to under heating, preferably under −10° C. to room temperature.

Each of the starting materials or intermediate compounds including the compound [a] and the like in the above reactions (reactions described in Methods A to D, methods a to e and Reaction Scheme A1 to E1) is a known compound or a compound which can be prepared from a known material by using a conventional synthetic procedure in the organic chemistry.

Among the above mentioned compounds [II-A] or their precursor compounds of the following formula [III]:

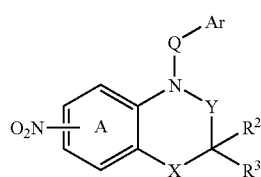

[III]

wherein the symbols are the same as defined above, a compound of the formula [ii]:

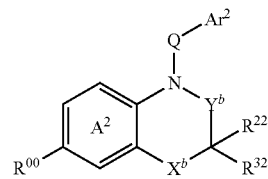

[ii]

wherein Ring $A^2$ is a benzene ring optionally substituted by, other than $R^{00}$, one to two group(s) selected from a halogen atom and an alkyloxy group, $R^{00}$ is a nitro group or an amino group, one of $R^{22}$ and $R^{32}$ is a hydrogen atom or an alkyl group and another is an alkyl group, a phenyl group or a halogenophenyl group, $X^b$ is an oxygen atom or a sulfur atom, $Y^b$ is a group of the formula: —C(=O)— or —CH($R^{52}$)—, $R^{52}$ is a hydrogen atom or a phenyl group, $Ar^2$ is a phenyl group optionally substituted by one to three group(s) selected from a halogen atom, a cyano group, an alkyl group, a trihalogenoalkyl group and an alkylenedioxy group optionally substituted by one to two halogen atom(s) and the other symbols are the same as defined above is useful as a synthetic intermediate, and also shows a high affinity to nuclear steroid receptors such as mineralocorticoid receptor (MR), glucocorticoid receptor (GR), androgen receptor (AR) and the like.

For example, in a biding assay with using mineralocorticoid receptors (MR) derived form rat kidney and $^3$H-aldosterone, 6-chloro-4-(4-fluorophenyl)-2,2-dimethyl -7-nitro-2H-1,4-benzoxizin-3(4H)-one or 4-(4-fluoro-2,6-dimethylphenyl)-6-iodo-2,2-dimethyl-7-nitro-2H-1,4-benzoxizin-3(4H)-one showed a Ki value less than 10 μM in binding of $^3$H-aldosterone to MR.

Besides, in a biding assay with using glucocorticoid receptors (GR) derived form rat liver and $^3$H-dexamethazone, each of the following compounds, 4-(4-fluorophenyl)-7-nitro-2-phenyl-2H-1,4-benzoxizin-3 (4H)-one, 4-benzyl-2,2-dimethyl-7-nitro-2H-1,4-benzoxizin-3(4H)-one, 4-(4-fluorophenyl)-2,2-dimethyl-7-nitro-3-phenyl-2H-1,4-benzoxizin-3(4H)-one, 4-(4-fluoro-3-methylphenyl)-2,2-dimethyl-7-nitro-2H-1,4-benzoxizin-3(4H)-one, 2,2-dimethyl-7-nitro-4-[(E)-2-phenylvinyl]-2H-1,4-benzoxizin-3(4H)-one, 4-benzyl-2-(4-chlorophenyl)-7-nitro-2H-1,4-benzoxizin-3 (4H)-one, 7-amino-4-benzyl-2-(4-chlorophenyl)-7-nitro-2H-1,4-benzoxizin-3(4H)-one and 4-(3-trifluoromethyl-4-methylphenyl)-2,2-dimethyl-7-nitro-2H-1,4-benzoxizin-3(4H)-one, showed a Ki value less than 10 μM in binding of $^3$H-dexamethazone to GR.

Furthermore, in a biding assay with using androgen receptors (AR) derived form rat prostate and $^3$H-methyltrienorone, 7-amino-4-(3,4-difluorophenyl)-2,2-dimethyl-2H -1,4-benzoxizin-3(4H)-one showed a Ki value less than 10 μM in binding of $^3$H-methyltrienorone to AR. Each biding assay was conducted in a similar manner as the procedure described in The Journal of Pharmacology and Experimental Therapeutics, 1987; 240:p. 650-656.

From the results of assay mentioned above, the compound [ii] or a pharmaceutically acceptable salt thereof can be useful as a ligand to the receptors (a modulator of the receptor activity) and therefore, useful as an agent for prophylaxis or treatment of a nuclear steroid hormone receptor-associated disease.

Throughout the present description and claims, the "halogen" means fluorine, chlorine, bromine or iodine, the "alkyl" means a straight or branched chain alkyl having 1 to 6 carbon atoms, preferably 1 to 4 carbon atoms, the "alkoxy" means a straight or branched chain alkoxy having 1 to 6 carbon atoms, preferably 1 to 4 carbon atoms, the "alkanoyl" means a straight or branched chain alkanoyl having 1 to 7 carbon atoms, preferably 2 to 5 carbon atoms, the "alkenyl" means a straight or branched chain alkenyl having 2 to 12 carbon atoms, preferably 2 to 6 carbon atoms, the "alkylene" means a straight or branched chain alkylene having 1 to 6 carbon atoms, preferably 1 to 4 carbon atom, the "alkenylene" means a straight or branched chain alkenylene having 2 to 6 carbon atoms, preferably 2 to 4 carbon atoms, the "alkylenedioxy" means a straight or branched chain alkylenedioxy having 1 to 6 carbon atoms, preferably 1 to 4 carbon atoms, the "cycloalkyl" means a cycloalkyl having 3 to 10 carbon atoms, preferably 3 to 8 carbon atom, the "cycloalkenyl" means a cycloalkenyl having 3 to 8 carbon atoms, preferably 3 to 7 carbon atoms, and the "aralkyl" means an aralkyl having 7 to 16 carbon atoms (a $C_{6-10}$ aryl-$C_{1-6}$ alkyl), preferably 7 to 10 carbon atoms (a $C_6$ aryl-$C_{1-4}$ alkyl).

EXAMPLES

The objective compound of the present invention obtained in each of the above-mentioned processes is exemplified in more detail by the following Examples but should not be construed to be limited thereto.

Example 1

To a solution of 7-amino-2,2-dimethyl-4-phenyl-2H-1,4-benzoxazin-3(4H)-one (compound obtained in Reference Example 1(3), 50 mg) in chloroform (2 mL) were added dropwise successively methanesulfonyl chloride (22 μL) and pyridine (30 μL) under ice-cooling and the mixture was stirred at room temperature for 18 hours. To the reaction mixture was added a saturated sodium hydrogencarbonate solution, and the mixture was extracted with chloroform. The organic layer was washed successively with water, 10% HCl solution and brine, dried over sodium sulfate and concentrated in vacuo. The resultant residue was purified by column chromatography on NH-silica gel (solvent; n-hexane/ethyl acetate=1/1→ethyl acetate) to give N-(2,2-dimethyl-3-oxo-4-phenyl-3,4-dihydro-2H-1,4-benzoxazin-7-yl)methanesulfonamide (55 mg) as a colorless powder. MS (APCI) m/z: 347 [M+H]$^+$ Examples 2 to 38

The corresponding materials were treated in the same manner as described in Example 1 to give compounds shown in the following Tables 1 to 8.

TABLE 1

| Ex. Nos. | Ar | R³ | Physicochemical properties etc. |
|---|---|---|---|
| 2 | phenyl | phenyl | powder<br>MS(APCI)m/z: 395[M + H]$^+$ |
| 3 | 3-fluorophenyl | phenyl | colorless powder<br>MS(APCI)m/z: 413[M + H]$^+$ |
| 4 | 4-fluorophenyl | phenyl | colorless powder<br>MS(APCI)m/z: 413[M + H]$^+$ |
| 5 | 2-fluorophenyl | phenyl | colorless powder<br>MS(APCI)m/z: 413[M + H]$^+$ |
| 6 | 4-chlorophenyl | phenyl | colorless powder<br>MS(APCI)m/z: 429/431[M + H]$^+$ |
| 7 | 4-fluorophenyl | H | powder<br>MS(APCI)m/z: 337[M + H]$^+$ |
| 8 | 4-fluorophenyl | CH₃ | powder<br>MS(APCI)m/z: 351[M + H]$^+$ |

TABLE 2

![Structure: benzoxazinone with Ar on N, two CH3 at position 2, and H3C-O2S-HN- substituent on benzene ring]

| Ex. Nos. | Ar | Physicochemical properties etc. |
|---|---|---|
| 9 | 4-F-C6H4- | pale pink powder<br>MS(APCI)m/z: 365[M + H]+ |
| 10 | 3,4-diF-C6H3- | pale yellow powder<br>MS(ESI)m/z: 381[M − H]− |
| 11 | 4-Cl-C6H4- | colorless powder<br>MS(APCI)m/z: 381[M + H]+ |
| 12 | 4-F-3-CH3-C6H3- | purple powder<br>MS(APCI)m/z: 379[M + H]+ |
| 13 | 3-Cl-4-F-C6H3- | pale red solid<br>MS(APCI)m/z: 399/401[M + H]+ |
| 14 | 4-CH3O-C6H4- | colorless solid<br>MS(APCI)m/z: 377[M + H]+ |
| 15 | 5-methyl-2-chlorothien-yl | colorless powder<br>MS(APCI)m/z: 387/389[M + H]+ |

TABLE 3

![Structure: benzoxazinone with N-benzyl, R3 at position 2, H3CO2SHN- on benzene ring]

| Ex. Nos. | R3 | Physicochemical properties etc. |
|---|---|---|
| 16 | phenyl | powder<br>MS(APCI)m/z: 409[M + H]+ |
| 17 | 4-Cl-C6H4- | colorless powder<br>MS(APCI)m/z: 443/445[M + H]+ |

TABLE 4

![Structure: benzoxazinone with N-O-Ar, R2 and R3 at position 2, H3C-O2S-HN- on benzene ring]

| Ex. Nos. | Ar—Q— | R2 | R3 | Physicochemical properties etc. |
|---|---|---|---|---|
| 18 | PhCH2CH2- | H | H | powder<br>MS(APCI)m/z: 333[M + H]+ |
| 19 | PhCH2CH2- | CH3 | CH3 | colorless powder<br>MS(APCI)m/z: 361[M + H]+ |
| 20 | 4-F-C6H4-CH2CH2- | CH3 | CH3 | colorless powder<br>MS(APCI)m/z: 379[M + H]+ |
| 21 | Ph-CH2CH2CH2- | CH3 | CH3 | colorless powder<br>MS(APCI)m/z: 375[M + H]+ |
| 22 | Ph-CH=CH-CH2- | CH3 | CH3 | colorless powder<br>MS(APCI)m/z: 373[M + H]+ |

TABLE 5

[Structure: benzoxazin-3-one core with Ar on N, R⁰ on ring, Rᵃ-O₂S-HN- on ring, 2,2-dimethyl]

| Ex. Nos. | Ar | R⁰ | Rᵃ | Physicochemical properties etc. |
|---|---|---|---|---|
| 23 | 6-fluoropyridin-3-yl (F-pyridine, 2-F, 5-yl) | H | CH₃ | pale pink powder MS(APCI)m/z: 366[M + H]⁺ |
| 24 | 4-fluorophenyl | H | C₂H₅ | white powder MS(APCI)m/z: 379[M + H]⁺ |
| 25 | 5-fluoro-2-methylpyridin-... (F-pyridine) | H | CH₃ | colorless powder MS(APCI)m/z: 366[M + H]⁺ |
| 26 | 4-fluorophenyl | H | 2-thienyl | white powder MS(APCI)m/z: 433[M + H]⁺ |
| 27 | 4-fluorophenyl | H | cyclopropyl | white powder MS(APCI)m/z: 391[M + H]⁺ |
| 28 | 4-fluorophenyl | Cl | CH₃ | colorless powder MS(APCI)m/z: 399/401[M + H]⁺ |
| 29 | 4-fluorophenyl | H | (CH₃)₂N— | white powder MS(APCI)m/z: 394[M + H]⁺ |

TABLE 6

[Structure: 3,4-dihydro-2H-benzoxazine core with Ar on N, R⁵ at 3-position, 2,2-dimethyl, H₃C-O₂S-HN- on ring]

| Ex. Nos. | Ar | R⁵ | Physicochemical properties etc. |
|---|---|---|---|
| 30 | 4-fluorophenyl | phenyl | powder MS(APCI)m/z: 427[M + H]⁺ |
| 31 | 4-fluorophenyl | H | powder MS(APCI)m/z: 351[M + H]⁺ |

TABLE 7

[Structure: Benzoxazinone core with Ar on N, two CH3 on carbon adjacent to O, and R^a—O2S—HN— substituent on the benzene ring]

| Ex. Nos. | Ar | R^a | Physicochemical properties etc. |
|---|---|---|---|
| 32 | 4-F-C6H4— | C6H5— | white powder MS(APCI)m/z: 427[M + H]+ |
| 33 | 4-F-C6H4— | (CH3)2CH— | white powder MS(APCI)m/z: 393[M + H]+ |
| 34 | 3-thienyl | CH3 | colorless powder MS(APCI)m/z: 353[M + H]+ |
| 35 | 4-F-3-(F3C)-C6H3— | CH3 | colorless powder MS(ESI)m/z: 431[M – H]– |

TABLE 8

[Structure: Benzoxazinone-like core with 4-fluorophenyl on N, R^2 and R^3 on carbon, X in ring, and H3C—O2S—HN— on benzene ring]

| Ex. Nos. | R^2 / R^3 | X | Physicochemical properties etc. |
|---|---|---|---|
| 36 | CH(CH3)—CH3 (isopropyl with methyl) | O | powder MS(APCI)m/z: 379[M + H]+ |
| 37 | spirocyclobutyl | O | powder MS(APCI)m/z: 377[M + H]+ |
| 38 | H, H (with isopropyl) | S | pale pink powder MS(APCI)m/z: 353[M + H]+ |

Example 39

7-Amino-4-(4-fluorophenyl)-2,2-dimethyl-2H-pyrido[3,2-b][1,4]oxazin-3(4H)-one (compound obtained in Reference Example 7(4), 113 mg) was treated in the same manner as described in Example 1 to give N-[4-(4-fluorophenyl)-2,2-dimethyl-3-oxo-3,4-dihydro-2H-pyrido[3,2-b][1,4]oxazin-7-yl]methanesulfonamide (98 mg) as colorless crystals. MS (APCI) m/z: 366 [M+H]+

Example 40

To a solution of N-[4-(4-methoxyphenyl)-2,2-dimethyl-3-oxo-3,4-dihydro-2H -1,4-benzoxazin-7-yl]methanesulfonamide (compound obtained in Example 14, 40 mg) in dichloromethane (5 mL) was added dropwise boron tribromide-dichloromethane solution (1.0 M, 0.32 mL) under cooling in dry ice-acetone bath. The reaction mixture was stirred at room temperature for 5.5 hours, and thereto was added an aqueous saturated sodium hydrogencarbonate solution. The mixture was extracted with chloroform and the organic layer was washed with brine, dried over sodium sulfate and concentrated in vacuo. The resultant residue was purified by column chromatography on silica gel (solvent; n-hexane/ethyl acetate=4/1→3/7) to give N-[4-(4-hydroxyphenyl)-2,2-dimethyl-3-oxo-3,4-dihydro-2H-1,4-benzoxazin-7-yl]methanesulfonamide (35 mg) as a colorless powder. MS (APCI) m/z: 363 [M+H]+

Example 41

(1) To a solution of 7-amino-4-(4-fluorophenyl)-2,2-dimethyl-2H-1,4-benzoxazin-3(4H)-one (compound obtained in Reference Example 15, 50 mg) in acetic acid (465 µL)/concentrated hydrochloric acid (570 µL) was added a solution of sodium nitrite (13.3 mg) in water (115 µL) under ice-cooling, and the mixture was stirred at the same temperature for 1.5 hours. To the reaction mixture was added a mixture of sodium hydrogen sulfite (182 mg), copper(II) chloride (23.5 mg), acetic acid (225 µL) and concentrated hydrochloric acid (115 µL) at the same temperature, and the mixture was stirred at room temperature for 2 hours. After ice-cooling, the reaction mixture was gradually poured to water with ice (15 mL) and extracted with ethyl acetate. The organic layer was washed with water, dried over sodium sulfate and concentrated in vacuo to give crude 4-(4-fluorophenyl)-2,2-dimethyl-3-oxo-3,4-dihydro-2H-1,4-benzoxazin-7-sulfonyl chloride.

(2) To a suspension of the compound obtained in the above step (1) in chloroform (2 mL) was added an aqueous 40% methylamine solution (1 mL) under ice-cooling, and the mixture was stirred at room temperature for 1 hour. To the reaction mixture was added chloroform, washed with water, dried over sodium sulfate and concentrated in vacuo. The resultant residue was purified by column chromatography on silica gel (solvent; n-hexane/ethyl acetate=9/1→1/1) to give 4-(4-fluorophenyl)-N,2,2-trimethyl-3-oxo-3,4-dihydro-2H-1,4-benzoxazine-7-sulfonamide (31 mg) as a colorless powder.
MS (APCI) m/z: 365 [M+H]$^+$ Example 42

7-Amino-4-(4-fluorophenyl)-2,2-dimethyl-2H-1,4-benzothiazin-3(4H)-one (compound obtained in Reference Example 28(3), 124 mg) was treated in the same manner as described in Example 1 to give N-[4-(4-fluorophenyl)-2,2-dimethyl-3-oxo -3,4-dihydro-2H-1,4-benzothiazin-7-yl]methanesulfonamide (149 mg) as a pink powder.
MS (APCI) m/z: 381 [M+H]$^+$ Example 43

A mixture of palladium acetate (1.3 mg), 2-dicyclohexylphosphino-2',4',6'-triisopropyl-1,1'-biphenyl (7.2 mg), phenylboronic acid (0.9 mg) and tert-butanol (2 mL) was stirred at room temperature for 20 minutes under argon atmosphere. To the reaction mixture were added N-[4-(3-chloro-4-fluorophenyl)-2,2-dimethyl-3-oxo-3,4-dihydro-2H-1,4-benzoxazin-7-yl]methanesulfonamide (compound obtained in Example 13, 60 mg), potassium carbonate (62 mg), tert-butyl carbamate (35 mg) and tert-butanol (5 mL), and the mixture was refluxed for 3 hours. To the reaction mixture were further added palladium acetate (1.3 mg), 2-dicyclohexylphosphino-2',4',6'-triisopropyl-1,1'-biphenyl (7.2 mg), potassium carbonate (62 mg) and tert-butyl carbamate (35 mg), and the mixture was further refluxed for 20 hours. After cooling, the reaction mixture was diluted with ethyl acetate, and the mixture was washed successively with water and brine, dried over sodium sulfate and concentrated in vacuo. The resultant residue was purified by column chromatography on silica gel (solvent; n-hexane/ethyl acetate =4/1→3/7) to give tert-butyl (5-{2,2-dimethyl-7-[(methylsulfonyl)amino]-3-oxo-2,3-dihydro-4H-1,4-benzoxazin-4-yl}-2-fluorophenyl)-carbamate (83 mg) as a colorless powder.
MS (APCI) m/z: 497 [M+NH$_4$]$^+$ Example 44

To a solution of the compound obtained in Example 43 (72 mg) in chloroform (5 mL) was added 4N HCl-ethyl acetate solution (10 mL), and the mixture was stirred at room temperature for 9 hours. To the reaction mixture was added an aqueous saturated sodium hydrogencarbonate solution, and the mixture was extracted with ethyl acetate. The organic layer was dried over sodium sulfate and concentrated in vacuo. The resultant residue was purified by column chromatography on silica gel (solvent; chloroform/methanol=100/1→9/1) to give N-[4-(3-amino-4-fluorophenyl)-2,2-dimethyl-3-oxo-2,3-dihydro-2H-1,4-benzoxazin-7-yl]methanesulfonamide (40 mg) as a colorless powder.
MS (APCI) m/z: 380 [M+H]$^+$ Example 45

6-Amino-1-(4-fluorophenyl)-3,3-dimethyl-3,4-dihydroquinoxalin-2(1H)-one (compound obtained in Reference Example 29(4), 62 mg) was treated in the same manner as described in Example 1 to give N-[1-(4-fluorophenyl)-3,3-dimethyl-2-oxo -1,2,3,4-tetrahydroquinoxalin-6-yl]methanesulfonamide (55 mg) as a colorless powder.
MS (APCI) m/z: 364 [M+H]$^+$ Example 46

To a suspension of N-[4-(4-fluorophenyl)-2,2-dimethyl-3-oxo-3,4-dihydro-2H -1,4-benzoxazin-7-yl]methanesulfonamide (compound of Example 9, 182 mg) in dioxane (10 mL) was added Lawesson's reagent (202 mg), and the mixture was stirred at room temperature for 2 hours and then stirred at 40° C. for 24 hours. The reaction mixture was diluted with chloroform and the mixture was filtered through a NH-silica gel pad and washed with ethyl acetate. The filtrate and the washings were combined and concentrated in vacuo. The resultant residue was purified by column chromatography on silica gel (solvent; n-hexane/ethyl acetate=19/1→3/2) to give N-[4-(4-fluorophenyl)-2,2-dimethyl-3-thioxo-3,4-dihydro-2H-1,4-benzoxazin-7-yl]methanesulfonamide (25 mg) as a yellow powder.
MS (APCI) m/z: 381 [M+H]$^+$ Example 47

(1) Tert-butyl [(2,2-dimethyl-3-oxo-3,4-dihydro-2H-1,4-benzoxazin-7-yl) -methyl](methylsulfonyl)carbamate (compound obtained in Reference Example 48(2), 200 mg) and 4-fluorophenylboronic acid (146 mg) were treated in the same manner as described in Reference Example 1(2) to give tert-butyl {[4-(4-fluorophenyl)-2,2-dimethyl-3-oxo-3,4-dihydro-2H-1,4-benzoxazin-7-yl]methyl}(methylsulfonyl) carbamate (50 mg) as a colorless powder.
MS (APCI) m/z: 479 [M+H]$^+$ (2) The compound obtained in the above step (1) (50 mg) was treated in the same manner as described in Example 44 to give N-{[4-(4-fluorophenyl)-2,2-dimethyl -3-oxo-3,4-dihydro-2H-1,4-benzoxazin-7-yl]methyl}methanesulfonamide (19 mg) as a colorless powder.
MS (APCI) m/z: 379 [M+H]$^+$ Example 48

To a solution of 3M sulfuric acid (4 μL) and 36% formamide solution (9.5 mg) in tetrahydrofuran (2 mL) was added a suspension of N-[4-(3-amino-4-fluorophenyl) -2,2-dimethyl-3-oxo-3,4-dihydro-2H-1,4-benzoxazin-7-yl]methanesulfonamide (compound obtained in Example 44; 20 mg) and sodium borohydride (1 mg) in tetrahydrofuran (3 mL) under cooling in ice/NaCl bath, and the mixture was stirred at room temperature for 1 hour. To the reaction mixture was added an aqueous saturated sodium hydrogencarbonate solution, and the mixture was extracted with ethyl acetate. The organic layer was washed with brine, dried over sodium sulfate and concentrated in vacuo. The residue was purified by column chromatography on silica gel (solvent; n-hexane/ethyl acetate=7/3→3/7) to give N-{4-[3-(dimethylamino)-4-fluorophenyl]-2,2-dimethyl-3-oxo-3,4-dihydro-2H-1,4-benzoxazin-7-yl}methanesulfonamide (10 mg) as a colorless powder.
MS (APCI) m/z: 408 [M+H]$^+$ Examples 49 to 106

The corresponding materials were treated in the same manner as described in Example 1 to give compounds shown in the following Tables 9 to 16.

TABLE 9

Structure: 4-Ar-7-(methanesulfonylamino)-2,2-dimethyl-2H-benzo[b][1,4]oxazin-3(4H)-one H₃C—O₂S—HN—[benzoxazinone with Ar on N, 2,2-diCH₃, 3-oxo]

| Example Nos. | Ar | Physicochemical properties etc. |
| --- | --- | --- |
| 49 | 2,4-difluorophenyl | colorless powder MS(APCI)m/z: 383[M + H]⁺ |
| 50 | 4-fluoro-2-methylphenyl | colorless powder MS(APCI)m/z: 379[M + H]⁺ |
| 51 | 4-(methylthio)phenyl (H₃CS-C₆H₄-) | colorless powder MS(APCI)m/z: 393[M + H]⁺ |
| 52 | 4-(trifluoromethyl)phenyl (F₃C-C₆H₄-) | colorless powder MS(ESI)m/z: 413[M − H]⁻ |
| 53 | 3-methoxyphenyl (H₃CO-C₆H₄-) | yellow powder MS(APCI)m/z: 377[M + H]⁺ |
| 54 | 4-methylphenyl (H₃C-C₆H₄-) | colorless powder MS(APCI)m/z: 361[M + H]⁺ |
| 55 | 4-fluoro-3-methoxyphenyl | colorless powder MS(APCI)m/z: 395[M + H]⁺ |
| 56 | 4-chloro-3-methoxyphenyl | colorless powder MS(APCI)m/z: 411/413[M + H]⁺ |

TABLE 10

Structure: 4-(4-fluorophenyl)-7-(methanesulfonylamino)-2-R²-2-R³-2H-benzo[b][1,4]oxazin-3(4H)-one

| Example Nos. | R²/R³ | Physiochemical properties etc. |
| --- | --- | --- |
| 57 | R² = R³ together: -C(CH₃)(C₂H₅)- (methyl, ethyl) | powder MS(APCI)m/z: 365[M + H]⁺ |
| 58 | -C(C₂H₅)(C₂H₅)- with additional CH₃ (diethyl, methyl quaternary) | powder MS(APCI)m/z: 393[M + H]⁺ |
| 59 | spirocyclopropyl with methyl | powder MS(APCI)m/z: 363[M + H]⁺ |
| 60 | spirocyclopentyl | powder MS(APCI)m/z: 391[M + H]⁺ |
| 61 | spirocyclohexyl | powder MS(APCI)m/z: 405[M + H]⁺ |

TABLE 11

Structure: 4-Ar-7-(methanesulfonylamino)-2-R²-2-R³-2H-benzo[b][1,4]oxazin-3(4H)-one

| Example Nos. | Ar | R² | R³ | Physicochemical properties etc. |
| --- | --- | --- | --- | --- |
| 62 | 4-fluorophenyl | CH₃ | EtOCO— | pale red powder MS(APCI)m/z: 423[M + H]⁺ |

TABLE 11-continued

[Structure: 4-Ar-7-(methanesulfonylamino)-2,3-dihydro-2,2-R²R³-benzo[1,4]oxazin-3-one]

H₃C—O₂S—HN—[benzoxazinone core with Ar on N, R², R³ on C2]

| Example Nos. | Ar | R² | R³ | Physicochemical properties etc. |
|---|---|---|---|---|
| 63 | 4-fluoro-2-methylphenyl (H₃C, F) | H | H | white powder<br>MS(APCI)m/z: 351[M + H]⁺ |
| 64 | pyridin-3-yl | CH₃ | CH₃ | pale yellow powder<br>MS(APCI)m/z: 348[M + H]⁺ |
| 65 | 2,3-dihydrobenzo[1,4]dioxin-6-yl | CH₃ | CH₃ | yellow powder<br>MS(APCI)m/z: 405[M + H]⁺ |
| 66 | 4-ethylphenyl (Et) | CH₃ | CH₃ | colorless powder<br>MS(APCI)m/z: 375[M + H]⁺ |
| 67 | 3-chloro-4-fluorophenyl (Cl, F) | H | H | white powder<br>MS(APCI)m/z: 371/373[M + H]⁺ |

Et: ethyl group

TABLE 12

[Structure: same benzoxazinone scaffold as above]

H₃C—O₂S—HN—[benzoxazinone core with Ar on N, R², R³ on C2]

| Example Nos. | Ar | R² | R³ | Physicochemical properties etc. |
|---|---|---|---|---|
| 68 | 2-chloro-4-fluoro-... (F, Cl) | CH₃ | CH₃ | colorless powder<br>MS(ESI)m/z: 397/399[M − H]⁻ |
| 69 | 2-methoxy-4-fluoro-... (F, OCH₃) | CH₃ | CH₃ | colorless powder<br>MS(APCI)m/z: 395[M + H]⁺ |
| 70 | 5-chlorothiophen-2-yl (Cl, S) | H | H | orange powder<br>MS(ESI)m/z: 357/359[M − H]⁻ |
| 71 | 4-chloro-2-fluoro-... (Cl, F) | CH₃ | CH₃ | white powder<br>MS(APCI)m/z: 399/401[M + H]⁺ |

TABLE 12-continued

Structure: H3C—O2S—HN-[benzoxazinone with Ar on N, R2 and R3 on C]

| Example Nos. | Ar | R² | R³ | Physicochemical properties etc. |
|---|---|---|---|---|
| 72 | 2-Cl, 5-CH3 phenyl (2-methyl-5-chlorophenyl) | CH₃ | CH₃ | colorless powder<br>MS(APCI)m/z: 395/397[M + H]⁺ |
| 73 | 4-Br phenyl (with methyl) | CH₃ | CH₃ | colorless powder<br>MS(APCI)m/z: 425/427[M + H]⁺ |
| 74 | 2-F, 3-CHF₂ phenyl (with methyl) | CH₃ | CH₃ | pale yellow powder<br>MS(APCI)m/z: 415[M + H]⁺ |

TABLE 13

Structure: H3C—O2S—HN-[benzoxazinone, Ar on N, 2,2-diCH₃]

| Example Nos. | Ar | Physicochemical properties etc. |
|---|---|---|
| 75 | 5-bromopyrimidin-2-yl | colorless powder<br>MS(APCI)m/z: 427/429[M + H]⁺ |
| 76 | 2-CH₃, 5-CN phenyl | red viscous oil<br>MS(APCI)m/z: 386[M + H]⁺ |
| 77 | 5-Cl, 2-CH₃, 3-CN phenyl | orange powder<br>MS(APCI)m/z: 406/408[M + H]⁺ |
| 78 | 5-chloropyridin-2-yl | pale yellow powder<br>MS(APCI)m/z: 382/384[M + H]⁺ |
| 79 | 5-Br, 2-CH₃ phenyl (with CH3) | green powder<br>MS(APCI)m/z: 439/441[M + H]⁺ |
| 80 | 2-CF₃, 4-Cl phenyl | yellow powder<br>MS(ESI)m/z: 447/449 [M − H]⁻ |

TABLE 13-continued

| Example Nos. | Ar | Physicochemical properties etc. |
|---|---|---|
| 81 | 3-F, 4-CF₃ phenyl | yellow powder<br>MS(ESI)m/z: 431[M − H]⁻ |

TABLE 14

Structure: H3C—O2S—HN-[benzoxazinone, Ar on N, 2,2-diCH₃]

| Example Nos. | Ar | Physicochemical properties etc. |
|---|---|---|
| 82 | 3-Cl, 4-F phenyl (with methyl) | colorless powder<br>MS(APCI)m/z: 399/401[M + H]⁺ |
| 83 | 3-CH₃, 4-Cl phenyl | pale brown powder<br>MS(APCI)m/z: 395/397[M + H]⁺ |

TABLE 14-continued

[Structure: Ar-N benzoxazinone with H3C—O2S—HN— substituent and 2,2-dimethyl groups]

| Example Nos. | Ar | Physicochemical properties etc. |
|---|---|---|
| 84 | 4-methyl-2-fluoro-5-methylphenyl (H3C, F substituents) | pale yellow powder<br>MS(APCI)m/z: 379[M + H]$^+$ |
| 85 | 2,4,5-trimethylphenyl | white powder<br>MS(APCI)m/z: 375[M + H]$^+$ |
| 86 | 4-methyl-2-chlorophenyl (H3C, Cl) | colorless powder<br>MS(APCI)m/z: 395/397[M + H]$^+$ |

TABLE 14-continued

[Structure: Ar-N benzoxazinone with H3C—O2S—HN— substituent and 2,2-dimethyl groups]

| Example Nos. | Ar | Physicochemical properties etc. |
|---|---|---|
| 87 | 4-cyclopropylphenyl | pale yellow powder<br>MS(APCI)m/z: 387[M + H]$^+$ |
| 88 | 3,4-difluoro-5-methylphenyl (H3C) | pale yellow powder<br>MS(APCI)m/z: 413[M + H]$^+$ |
| 89 | 3-trifluoromethyl-4-methylphenyl (F3C, H3C) | white powder<br>MS(APCI)m/z: 429[M + H]$^+$ |

TABLE 15

[Structure: Ar-N benzoxazinone with H3C—O2S—HN— substituent and 2,2-dimethyl groups]

| Example Nos. | Ar | Physicochemical properties etc. |
|---|---|---|
| 90 | 3-trifluoromethylphenyl (F3C) | white powder<br>MS(APCI)m/z: 415[M + H]$^+$ |
| 91 | 6-trifluoromethylpyridin-3-yl (F3C, N) | white powder<br>MS(APCI)m/z: 416[M + H]$^+$ |
| 92 | 3,4-dichlorophenyl (Cl, Cl) | pale pink powder<br>MS(APCI)m/z: 415/417[M + H]$^+$ |
| 93 | naphthalen-2-yl | yellow powder<br>MS(APCI)m/z: 397[M + H]$^+$ |
| 94 | 3-(methylsulfonyl)phenyl (H3CO2S) | yellow powder<br>MS(APCI)m/z: 425[M + H]$^+$ |
| 95 | 3-trifluoromethyl-2-methylphenyl (F3C, CH3) | white powder<br>MS(APCI)m/z: 429[M + H]$^+$ |

TABLE 15-continued

[Structure: 4-Ar-7-(methanesulfonylamino)-2,2-dimethyl-2H-1,4-benzoxazin-3(4H)-one]

| Example Nos. | Ar | Physicochemical properties etc. |
|---|---|---|
| 96 | 5-fluoro-2,3-dimethyl-1-(trifluoromethyl)phenyl (F, CH₃, CH₃, CF₃ substituted phenyl) | colorless powder MS(APCI)m/z: 393[M + H]⁺ |
| 97 | 4-chloro-2-methylphenyl (Cl, CH₃ substituted phenyl) | white powder MS(APCI)m/z: 395/397[M + H]⁺ |
| 98 | 3-(tert-butoxycarbonylmethoxy)phenyl (t-BuO-C(O)-CH₂-O- substituted phenyl) | colorless powder MS(APCI)m/z: 494[M + NH₄]⁺ | t-Bu: tert-butyl group

TABLE 16

[Structure: 4-Ar-7-(methanesulfonylamino)-2,2-dimethyl-2H-1,4-benzoxazin-3(4H)-one with R', R'', R''' substituents]

| Example Nos. | Ar | R' | R'' | R''' | Physicochemical properties etc. |
|---|---|---|---|---|---|
| 99 | 4-fluorophenyl | H | F | H | yellow powder MS(APCI)m/z: 383[M + H]⁺ |
| 100 | 4-fluorophenyl | H | CH₃ | CH₃ | yellow powder MS(APCI)m/z: 393[M + H]⁺ |
| 101 | 4-fluorophenyl | H | CH₃O | H | colorless powder MS(APCI)m/z: 395[M + H]⁺ |
| 102 | 4-fluorophenyl | H | CH₃ | H | colorless powder MS(APCI)m/z: 379[M + H]⁺ |
| 103 | 4-fluorophenyl | Cl | H | H | pale yellow powder MS(APCI)m/z: 399/401[M + H]⁺ |

TABLE 16-continued

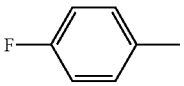

| Example Nos. | Ar | R' | R'' | R''' | Physicochemical properties etc. |
|---|---|---|---|---|---|
| 104 | 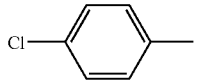 4-F-C6H4 | Br | H | H | pale yellow powder<br>MS(APCI)m/z: 443/445[M + H]+ |
| 105 |  4-Cl-C6H4 | Cl | H | H | colorless powder<br>MS(APCI)m/z: 415/417[M + H]+ |
| 106 | 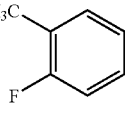 4-F-C6H4 | CH3 | H | H | colorless powder<br>MS(APCI)m/z: 379[M + H]+ |

Examples 107 to 113

The corresponding starting materials were treated in the same manner as described in Example 41 to give compounds shown in the following Table 17.

TABLE 17

| Example Nos. | Ar | (R$^c$)(R$^b$)N— | Physicochemical properties etc. |
|---|---|---|---|
| 107 | 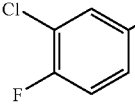 3-CH3-4-F-C6H3 | (CH3)NH— | red viscous oil<br>MS(APCI)m/z: 379[M + H]+ |
| 108 | 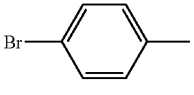 4-F-C6H4 | (C2H5)NH— | solid<br>MS(APCI)m/z: 379[M + H]+ |
| 109 | 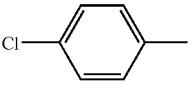 3-Cl-4-F-C6H3 | (CH3)NH— | yellow viscous oil<br>MS(APCI)m/z: 397/399[M + H]+ |
| 110 | 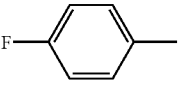 4-Br-C6H4 | (CH3)NH— | white powder<br>MS(APCI)m/z: 425/427[M + H]+ |
| 111 | 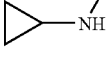 4-Cl-C6H4 | (CH3)NH— | colorless viscous oil<br>MS(APCI)m/z: 381/383[M + H]+ |
| 112 | 4-F-C6H4 | cyclopropyl-NH— | colorless viscous oil<br>MS(APCI)m/z: 391[M + H]+ |

TABLE 17-continued

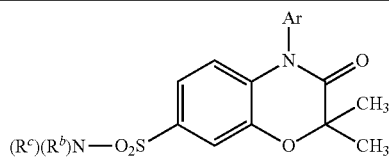

| Example Nos. | Ar | $(R^c)(R^b)N—$ | Physicochemical properties etc. |
|---|---|---|---|
| 113 | Cl-[dimethylphenyl with CH₃] | $(CH_3)NH—$ | white solid<br>MS(APCI)m/z: 395/397[M + H]⁺ |

Example 114

To a solution of chlorosulfonyl isocyanate (99 mg) in tetrahydrofuran (2 mL) was added dropwise tetrahydrofuran (0.5 mL) containing water (13 mg) under cooling in dry ice/acetone bath, and the mixture was stirred at the same temperature for 10 minutes. To the reaction mixture were added 4-(4-fluorophenyl)-7-amino-2,2-dimethyl -3,4-dihydro-2H-1,4-benzoxazin-3(4H)-one (compound obtained in Reference Example 14; 100 mg) and triethylamine (97 µL), and the mixture was stirred at the same temperature for 0.5 hour and stirred at room temperature for 2 hours. To the reaction mixture was added water, and the mixture was extracted with ethyl acetate. The organic layer was dried over sodium sulfate and concentrated in vacuo. The residue was purified by column chromatography on silica gel (solvent; n-hexane/ethyl acetate=9/1→2/1) and triturated with diethylether to give N-[4-(4-fluorophenyl)-2,2-dimethyl-3-oxo-3, 4-dihydro-2H-1,4-benzoxazin-7-yl]sulfamide (11 mg) as a colorless powder.

MS (APCI) m/z: 366 [M+H]⁺

Example 115

N-[4-(4-Fluoro-3-methoxyphenyl)-2,2-dimethyl-3-oxo-3, 4-dihydro-2H-1,4-benzoxazin-7-yl]methanesulfonamide (compound obtained in Example 55; 30 mg) was treated in the same manner as described in Example 40 to give N-[4-(4-fluoro-3-hydroxy-phenyl)-2,2-dimethyl-3-oxo-3,4-dihydro-2H-1,4-benzoxazin-7-yl]methanesulfonamide (17 mg) as colorless crystals.

MS (APCI) m/z: 381 [M+H]⁺

Example 116

To a solution of N-[4-(3-amino-4-fluorophenyl)-2,2-dimethyl-3-oxo-3,4-dihydro-2H-1,4-benzoxazin-7-yl]methanesulfonamide (compound obtained in Example 44; 13 mg) and pyridine (5.5 µL) in dichloromethane (5 mL) was added acetyl chloride (3.6 µL) under ice-cooling, and the mixture was stirred at the same temperature for 1 hour. The reaction mixture was purified by column chromatography on silica gel (solvent; chloroform to chloroform/methanol (9/1) and triturated with diisopropylether to give N-(5-{2,2-dimethyl-7-[(methanesulfonyl)amino]-3-oxo-2,3-dihydro-4H-1,4-benzoxazin-4-yl}-2-fluorophenyl)acetamide (10 mg) as a pale yellow powder.

MS (APCI) m/z: 422 [M+H]⁺

Example 117

N-[4-(4-Fluorophenyl)-6-methoxy-2,2-dimethyl-3-oxo-3, 4-dihydro-2H-1,4-benzoxazin-7-yl]methanesulfonamide (compound obtained in Example 101; 56 mg) was treated in the same manner as described in Example 40 to give N-[4-(4-fluoro phenyl)-6-hydroxy-2,2-dimethyl-3-oxo-3,4-dihydro-2H-1,4-benzoxazin-7-yl]methanesulfonamide (30 mg) as a colorless powder.

MS (APCI) m/z: 381 [M+H]⁺

Example 118

(1) Tert-butyl [7-amino-4-(4-fluorophenyl)-2,2-dimethyl-3-oxo-3,4-dihydro -2H-1,4-benzoxazin-6-yl]carbamate (compound obtained in Reference Example 50(4); 500 mg) was treated in the same manner as described in Example 1 to give tert-butyl {4-(4-fluorophenyl)-2,2-dimethyl-7-[(methylsulfonyl)amino]-3-oxo-3,4-dihydro-2H -1,4-benzoxazin-6-yl}carbamate (555 mg) as a colorless powder.

MS (APCI) m/z: 497 [M+NH₄]⁺

(2) The compound obtained in the above step (1) (525 mg) was treated in the same manner as described in Example 44 to give N-[6-amino-4-(4-fluorophenyl)-2,2-dimethyl-3-oxo-3, 4-dihydro-2H-1,4-benzoxazin-7-yl]methanesulfonamide (165 mg) as a pale yellow powder.

MS (APCI) m/z: 380 [M+H]⁺

Example 119

To a solution of the compound obtained in Reference Example 49(4) (60 mg) in trifluoroacetic acid (5 mL)-chloroform (1 mL) was added triethylsilane (93 mg), and the mixture was stirred at room temperature for 3 hour and at 50° C. for 24 hours. To the reaction mixture was added triethylsilane (93 mg), and the mixture was stirred at 70° C. for 24 hours. Thereto was further added triethylsilane (185 mg), and the mixture was stirred at 70° C. for 40 hours. After cooling, to the reaction mixture was added water, and the mixture was extracted with ethyl acetate. The organic layer was washed successively with water and brine, dried over sodium sulfate and concentrated in vacuo. The residue was purified by column chromatography on NH-silica gel (Chromatorex NH-silica gel; solvent; n-hexane/ethyl acetate=4/1 to 1/1) to give N-[1-(4-fluorophenyl)-3,3-dimethyl-2-oxo-1,2,3,4-tetrahydroquinolin-6-yl]methanesulfonamide (36 mg) as a colorless powder.

MS (APCI) m/z: 363 [M+H]⁺

Example 120

(1) To a solution of the compound obtained in Reference Example 57(2) (100 mg) in chloroform (15 nit) were added 10% palladium-carbon (75 mg, water content: ca. 50%) and a drop of conc. hydrochloric acid, and the mixture was stirred at room temperature under atmospheric pressure of hydrogen gas for 3 hours. The reaction mixture was diluted with 1,2-dimethoxyethane and filtered. The filtrate was concentrated in vacuo to give 7-amino-2-fluoro-4-(4-fluorophenyl)-2H-1, 4-benzoxazin -3(4H)-one hydrochloride as a crude product.

(2) The compound obtained in the above step (1) was treated in the same manner as described in Example 1 to give N-[2-fluoro-4-(4-fluorophenyl)-3-oxo-3,4-dihydro -2H-1,4-benzoxazin-7-yl]methanesulfonamide (9 mg) as a colorless powder.

Examples 121 to 162

The corresponding starting materials were treated in the same manner as described in Example 1 to give compounds shown in the following Tables 18 to 23.

TABLE 18

| Example Nos. | Ar | Physicochemical properties etc. |
|---|---|---|
| 121 | 4-Br, 3-CH₃-phenyl | colorless powder MS(APCI)m/z: 439/441[M + H]⁺ |
| 122 | 3-OCF₃-phenyl | orange powder MS(APCI)m/z: 431[M + H]⁺ |
| 123 | 2,2-difluoro-1,3-benzodioxol-5-yl | colorless powder MS(APCI)m/z: 427[M + H]⁺ |
| 124 | 3,4,5-trimethylphenyl | colorless powder MS(APCI)m/z: 389[M + H]⁺ |
| 125 | 2,3-dimethylphenyl | colorless powder MS(APCI)m/z: 375[M + H]⁺ |

TABLE 18-continued

| Example Nos. | Ar | Physicochemical properties etc. |
|---|---|---|
| 126 | 4-Cl-2,6-dimethylphenyl | colorless powder MS(APCI)m/z: 409/411[M + H]⁺ |
| 127 | 5-Br-2-methyl-3-methylpyridinyl | colorless powder MS(APCI)m/z: 440/442[M + H]⁺ |

TABLE 19

| Example Nos. | R' | Ar | Physicochemical properties etc. |
|---|---|---|---|
| 128 | F | 4-F-phenyl | pale pink powder MS(APCI)m/z: 383[M + H]⁺ |
| 129 | H | 3,5-diCl-2-methylpyridinyl | colorless powder MS(APCI)m/z: 416/418[M + H]⁺ |
| 130 | H | 4-F-2,3-dimethylphenyl | colorless powder MS(APCI)m/z: 393[M + H]⁺ |
| 131 | H | 2-Cl-3-methylphenyl | colorless powder MS(APCI)m/z: 395/397[M + H]⁺ |
| 132 | H | 4-F-2-methylphenyl | colorless powder MS(APCI)m/z: 379[M + H]⁺ |
| 133 | H | 1-phenylethyl | colorless powder MS(APCI)m/z: 375[M + H]⁺ |

TABLE 19-continued

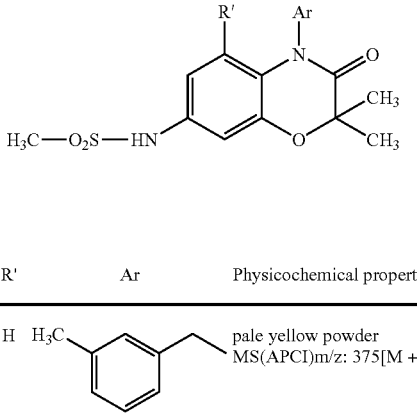

| Example Nos. | R' | Ar | Physicochemical properties etc. |
|---|---|---|---|
| 134 | H | 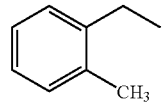 | pale yellow powder<br>MS(APCI)m/z: 375[M + H]⁺ |
| 135 | H | 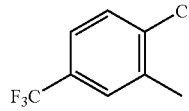 | colorless solid<br>MS(APCI)m/z: 375[M + H]⁺ |
| 136 | H | 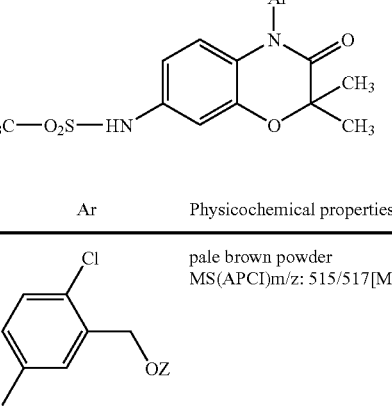 | colorless powder<br>MS(APCI)m/z: 429[M + H]⁺ |

TABLE 20

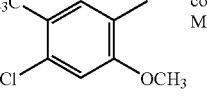

| Example Nos. | Ar | Physicochemical properties etc. |
|---|---|---|
| 137 | 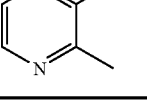 | colorless powder<br>MS(APCI)m/z: 427/429[M + H]⁺ |
| 138 | 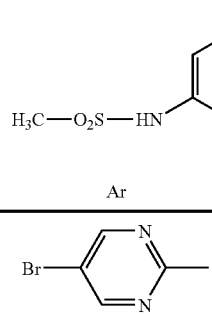 | colorless powder<br>MS(APCI)m/z: 398[M + H]⁺ |
| 139 | 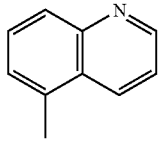 | colorless powder<br>MS(ESI)m/z: 399[M − H]⁻ |
| 140 | 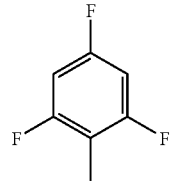 | pale yellow powder<br>MS(APCI)m/z: 498[M + NH₄]⁺ |

TABLE 20-continued

| Example Nos. | Ar | Physicochemical properties etc. |
|---|---|---|
| 141 | 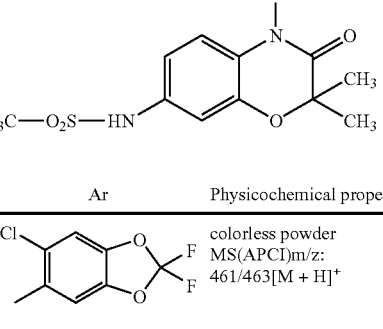 | pale brown powder<br>MS(APCI)m/z: 515/517[M + H]⁺ |
| 142 | 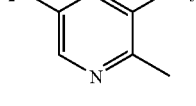 | colorless powder<br>MS(APCI)m/z: 425/427[M + H]⁺ |
| 143 | 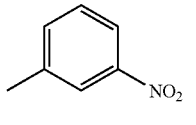 | colorless powder<br>MS(APCI)m/z: 362[M + H]⁺ |

Z = benzoyl group

TABLE 21

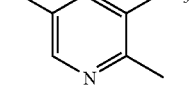

| Example Nos. | Ar | Physicochemical properties etc. |
|---|---|---|
| 144 | 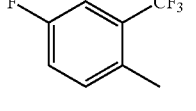 | colorless powder<br>MS(APCI)m/z:<br>461/463[M + H]⁺ |
| 145 | | yellow powder<br>MS(APCI)m/z: 407[M + H]⁺ |
| 146 | | colorless powder<br>MS(APCI)m/z: 409[M + NH₄]⁺ |
| 147 | | colorless powder<br>MS(APCI)m/z:<br>396/398[M + H]⁺ |
| 148 | | brown solid<br>MS(APCI)m/z: 433[M + H]⁺ |

TABLE 21-continued

Structure: Ar-N (benzoxazinone with CH₃, CH₃ groups), H₃C—O₂S—HN—

| Example Nos. | Ar | Physicochemical properties etc. |
|---|---|---|
| 149 | 2-CH₃-4-CF₃-phenyl (F₃C, CH₃ substituted phenyl) | colorless powder<br>MS(APCI)m/z: 429[M + H]⁺ |
| 150 | 5-CF₃-3-Cl-2-methylpyridinyl (F₃C, Cl, pyridine with CH₃) | colorless powder<br>MS(APCI)m/z: 450/452[M + H]⁺ |

TABLE 22

Structure: Ar-N (benzoxazinone with CH₃, CH₃), H₃C—O₂S—HN—

| Example Nos. | Ar | Physicochemical properties etc. |
|---|---|---|
| 151 | 3-chloro-phenyl (Cl-phenyl) | colorless powder<br>MS(APCI)m/z: 381/383[M + H]⁺ |
| 152 | 3-Br-2-CH₃-6-methylpyridinyl | pale purple powder<br>MS(APCI)m/z: 440/442[M + H]⁺ |
| 153 | 5-methyl-2-CF₃-thiophene | colorless powder<br>MS(APCI)m/z: 421[M + H]⁺ |
| 154 | 2-Cl-4-CH₃-5-methylpyridinyl | colorless powder<br>MS(APCI)m/z: 396/398[M + H]⁺ |
| 155 | 5-Br-pyridinyl | colorless powder<br>MS(APCI)m/z: 426/428[M + H]⁺ |
| 156 | 5-Br-4-CH₃-6-methylpyridinyl | colorless powder<br>MS(APCI)m/z: 440/442[M + H]⁺ |
| 157 | 6-CF₃-2-methylpyridinyl | colorless powder<br>MS(APCI)m/z: 416[M + H]⁺ |

TABLE 23

Structure: R'-Ar-N (benzoxazinone with CH₃, CH₃), H₃C—O₂S—HN—

| Example Nos. | R' | Ar | Physicochemical properties etc. |
|---|---|---|---|
| 158 | CH₂=CH— | 4-F-phenyl | pale pink powder<br>MS(APCI)m/z: 391[M + H]⁺ |
| 159 | CH₃—CO— | 4-F-phenyl | colorless powder<br>MS(APCI)m/z: 407[M + H]⁺ |
| 160 | F | 4-Cl-phenyl | colorless powder<br>MS(APCI)m/z: 399/401[M + H]⁺ |
| 161 | F | 5-Cl-2-pyridinyl | colorless powder<br>MS(APCI)m/z: 400/402[M + H]⁺ |

TABLE 23-continued

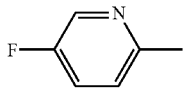

| Example Nos. | R' | Ar | Physicochemical properties etc. |
|---|---|---|---|
| 162 | F | 5-fluoro-pyridin-2-yl (F attached to pyridine) | colorless powder<br>MS(APCI)m/z: 384[M + H]$^+$ |

Example 163

To a solution of 2-chloro-5-{2,2-dimethyl-7-[(methylsulfonyl)amino]-3-oxo -2,3-dihydro-4H-1,4-benzoxazin-4-yl}benzyl benzoate (compound obtained in Example 141; 80 mg) in tetrahydrofuran (3 mL)-methanol (3 mL) was added an aqueous 2N sodium hydroxide solution (0.39 mL) under ice-cooling, and the mixture was stirred at the same temperature for 8 hours. The reaction mixture was acidified with an aqueous saturated ammonium chloride solution, and the mixture was extracted with ethyl acetate. The organic layer was washed with brine, dried over magnesium sulfate and concentrated in vacuo. The resultant residue was purified by column chromatography on silica gel (solvent; n-hexane/ethyl acetate=7/3→2/3) and triturated with diisopropylether/n-hexane (1/1) to give N-{4-[4-chloro-3-(hydroxymethyl)phenyl]-2,2-dimethyl-3-oxo-3,4-dihydro-2H-1,4-benzoxazin-7-yl]methanesulfonamide (39 mg) as a colorless powder.
MS (APCI) m/z: 411 [M+H]$^+$

Example 164

4-{2,2-Dimethyl-7-[(methylsulfonyl)amino]-3-oxo-2,3-dihydro-4H-1,4-benzoxazin-4-yl}benzyl benzoate (compound obtained in Example 140; 120 mg) was treated in the same manner as described in Example 163 to give N-{4-[4-(hydroxymethyl)phenyl]-2,2-dimethyl-3-oxo-3,4-dihydro-2H-1,4-benzoxazin-7-yl}methanesulfonamide (88 mg) as a colorless powder.
MS (APCI) m/z: 377 [M+H]$^+$

Example 165

To a solution of N-[2,2-dimethyl-4-(3-nitrophenyl)-3-oxo-3,4-dihydro-2H-1,4-benzoxazin-7-yl]methanesulfonamide (compound obtained in Example 146; 240 mg) in methanol (5 mL)-tetrahydrofuran (5 mL) was added 10% palladium-carbon (100 mg), and the mixture was stirred at room temperature under atmospheric pressure of hydrogen for 2 hours. The reaction mixture was filtered, and the filtrate was concentrated in vacuo to give N-[4-(3-aminophenyl)-2,2-dimethyl-3-oxo-3,4-dihydro -2H-1,4-benzoxazin-7-yl]-methanesulfonamide as a colorless powder.
MS (APCI) m/z: 362 [M+H]$^+$

Examples 166 to 177

The corresponding starting materials were treated in the same manner as described in Example 1 to give compounds shown in the following Tables 24 to 25.

TABLE 24

| Example Nos. | Ar | Physicochemical properties etc. |
|---|---|---|
| 166 | 6-bromo-5-methyl-pyridin-3-yl | colorless powder<br>MS(APCI)m/z: 440/442[M + H]$^+$ |
| 167 | 6-chloro-2-methyl-3-methyl-pyridin-... (Cl, CH₃, CH₃ substituted pyridinyl) | colorless powder<br>MS(APCI)m/z: 396/398[M + H]$^+$ |
| 168 | 5-trifluoromethyl-6-methyl-pyridin-2-yl | coloress powder<br>MS(APCI)m/z: 416[M + H]$^+$ |
| 169 | 6-trifluoromethyl-2-methyl-3-methyl-pyridinyl | colorless powder<br>MS(APCI)m/z: 430[M + H]$^+$ |
| 170 | 5-chloro-3-fluoro-2-methyl-pyridinyl | colorelss powder<br>MS(APCI)m/z: 400/402[M + H]$^+$ |
| 171 | 5-fluoro-3-methyl-2-methyl-pyridinyl | pale yellow powder<br>MS(APCI)m/z: 380[M + H]$^+$ |

TABLE 25

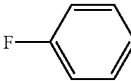

| Example Nos. | R' | Ar | Physicochemical properties etc. |
|---|---|---|---|
| 172 | CN | 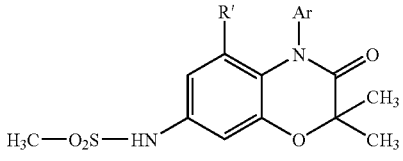 | pale yellow powder MS(APCI)m/z: 390[M + H]+ |
| 173 | F | 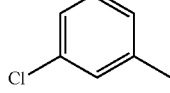 | colorless powder MS(APCI)m/z: 399/401[M + H]+ |
| 174 | F | 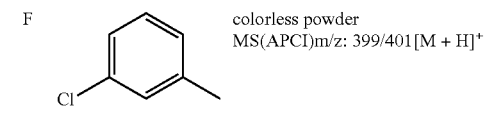 | colorless powder MS(APCI)m/z: 444/446[M + H]+ |
| 175 | F | 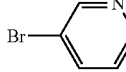 | pale yellow powder MS(APCI)m/z: 414/416[M + H]+ |
| 176 | F | 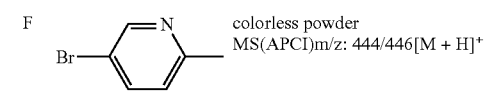 | colorless powder MS(APCI)m/z: 434[M + H]+ |
| 177 | F | 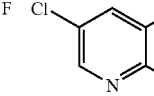 | pale yellow powder MS(APCI)m/z: 418/420[M + H]+ |

Example 178

To a solution of N-[4-(4-fluorophenyl)-2,2-dimethyl-3-oxo-5-vinyl-3,4-dihydro -2H-1,4-benzoxazin-7-yl]methanesulfonamide (compound obtained in Example 156, 200 mg) in ethanol (20 mL) was added 10% palladium-carbon (water content: ca. 50%, 200 mg), and the mixture was stirred under atmospheric pressure of hydrogen at room temperature for 20 hours. The reaction mixture was filtered through a celite pad, and the filtrate was concentrated in vacuo. The resultant residue was purified by column chromatography on silica gel (Solvent; chloroform→chloroform/ethyl acetate=10/1) to give N-[5-ethyl-4-(4-fluorophenyl)-2,2-dimethyl-3-oxo-3,4-dihydro-2H-1,4-benzoxazin-7-yl]methanesulfonamide (209 mg) as a colorless powder.
MS (APCI) m/z; 393 [M+H]+

Example 179

To a solution of N-[4-(4-fluorophenyl)-2,2-dimethyl-3-oxo-5-vinyl-3,4-dihydro -2H-1,4-benzoxazin-7-yl]methanesulfonamide (compound obtained in Example 156, 200 mg) in tetrahydrofuran (5 mL) was added 10 M borane-dimethylsulfide complex in tetrahydrofuran (0.03 mL) under ice-cooling, and the mixture was stirred at room temperature for 5 hours. Thereto was further added 10 M borane-dimethylsulfide complex in tetrahydrofuran (0.03 mL), and the mixture was stirred for 15 hours. To the reaction mixture were added successively tetrahydrofuran (5 mL), an aqueous 30% hydrogen peroxide solution (0.6 mL) and an aqueous 2N sodium hydroxide solution (0.77 mL), and the mixture was stirred at room temperature for 3 hours. The reaction mixture was poured to an aqueous saturated ammonium chloride solution, and the mixture was extracted with ethyl acetate. The organic layer was washed with water and brine, dried over sodium sulfate and concentrated in vacuo. The resultant residue was purified by column chromatography on silica gel (Solvent; chloroform→chloroform/ethyl acetate=100/0→0/100) to give N-[4-(4-fluorophenyl)-5-(2-hydroxyethyl)-2,2-dimethyl-3-oxo-3,4-dihydro-2H-1,4-benzoxazin-7-yl]methanesulfonamide (113 mg) as a colorless powder.
MS (APCI) m/z; 409 [M+H]+

Example 180

To solution of 7-amino-4-(4-fluorophenyl)-5-(hydroxymethyl)-2,2-dimethyl-2H -1,4-benzoxazin-3(4H)-one (compound obtained in Reference Example 175(3), 117 mg) and pyridine (0.12 mL) in dichloromethane (5 nm) was added dropwise methanesulfonyl chloride (0.085 mL) under ice-cooling, and the mixture was stirred at room temperature for 4 hours. To the reaction mixture was added water, and the mixture was extracted with ethyl acetate. The organic layer was washed with brine, dried over sodium sulfate and concentrated in vacuo. The resultant residue was dissolved in methanol (4 mL) and the solution was refluxed for 15 hours. The reaction mixture was concentrated in vacuo, and the resultant residue was purified by column chromatography on silica gel (Solvent; chloroform→chloroform/methanol=85/15) to give N-[4-(4-fluorophenyl)-5-(methoxymethyl)-2,2-dimethyl-3-oxo-3,4-dihydro-2H -1,4-benzoxazin-7-yl]methanesulfonamide as a pale yellow powder (40 mg, MS (APCI) m/z; 409 [M+H]+) and N-[4-(4-fluorophenyl)-5-(hydroxymethyl)-2,2-dimethyl-3-oxo-3,4-dihydro-2H-1,4-benzoxazin-7-yl]methanesulfonamide as a pale brown powder (52 mg, MS (APCI) m/z; 409 [M+H]+), respectively.

Examples 181 to 196

The corresponding starting materials were treated in the same manner as described in Example 1 to give compounds shown in the following Tables 26 to 27.

TABLE 26

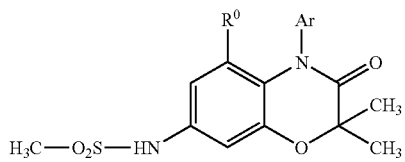

| Ex. Nos. | R⁰ | Ar | Physicochemical properties etc. |
|---|---|---|---|
| 181 | H | 6-bromo-3-methylpyridazin-3-yl | colorless powder<br>MS(APCI)m/z: 427/429[M + H]⁺ |
| 182 | H | 2-methyl-4-trifluoromethylpyridin-yl | colorless powder<br>MS(APCI)m/z: 416[M + H]⁺ |
| 183 | F | 2-chloro-5-methylbenzyl benzoate | colorless powder<br>MS(APCI)m/z: 533/535[M + H]⁺ |
| 184 | F | 4-chloro-2-methylpyridin-yl | colorless powder<br>MS(APCI)m/z: 400/402[M + H]⁺ |
| 185 | H | 2,3,6-trimethylpyridin-yl | yellow powder<br>MS(APCI)m/z: 376[M + H]⁺ |
| 186 | F | 3-fluoro-4-trifluoromethyl-phenyl | pale yellow powder<br>MS(APCI)m/z: 451[M + H]⁺ |
| 187 | F | 4-trifluoromethylphenyl | pale yellow powder<br>MS(APCI)m/z: 433[M + H]⁺ |
| 188 | F | 4-fluoro-3-trifluoromethyl-phenyl | colorless powder<br>MS(APCI)m/z: 451[M + H]⁺ |

TABLE 27

Common structure: 4-Ar-7-(methylsulfonylamino)-2,2-dimethyl-5-R⁰-2,3-dihydro-4H-1,4-benzoxazin-3-one

| Ex. Nos. | R⁰ | Ar | Physicochemical properties etc. |
|---|---|---|---|
| 189 | F | 3-chloro-4-fluorophenyl | colorless powder MS(APCI)m/z: 417/419[M + H]⁺ |
| 190 | F | 3,4-difluorophenyl | pale yellow powder MS(APCI)m/z: 401[M + H]⁺ |
| 191 | F | 2-methyl-3-fluoro-6-pyridyl | colorless powder MS(APCI)m/z: 398[M + H]⁺ |
| 192 | H | 3-fluoro-2-methyl-6-pyridyl | pale yellow powder MS(APCI)m/z: 380[M + H]⁺ |
| 193 | H | benzo[b]thiophen-2-yl | pale yellow powder MS(APCI)m/z: 403[M + H]⁺ |
| 194 | F | benzofuran-2-yl | pale brown powder MS(APCI)m/z: 387[M + H]⁺ |
| 195 | F | 5-methyl-3-trifluoromethyl-thiophen-2-yl | pale yellow powder MS(ESI)m/z: 437[M − H]⁻ |
| 196 | F | 5-fluoro-2-methyl-3-methyl-pyridyl | colorless powder MS(APCI)m/z: 398[M + H]⁺ |

Example 197

2-Chloro-5-{5-fluoro-2,2-dimethyl-[(methylsulfonyl)amino]-3-oxo-2,3-dihydro-4H-1,4-benzoxazin-4-yl}benzyl benzoate (compound obtained in Example 183, 128 mg) was treated in the same manner as described in Example 163 to give N-{4-[4-chloro-3-(hydroxymethyl)-phenyl]-5-fluoro-2,2-dimethyl-3-oxo-3,4-dihydro-2H-1,4-benzoxazin-7-yl]methanesulfonamide (28 mg) as a pale yellow powder.
MS (APCI) m/z; 429/431 [M+H]⁺

Examples 198 to 207

The corresponding starting materials were treated in the same manner as described in Example 1 give compounds shown in the following Table 28.

TABLE 28

| Ex. Nos. | R⁰ | Ar | Physicochemical properties etc. |
|---|---|---|---|
| 198 | F | 6-chloro-2-methyl-3-methyl-pyridyl | pale yellow powder MS(APCI)m/z: 414/416[M + H]⁺ |
| 199 | F | 5-chloro-2-fluoro-4-methylphenyl | pale yellow powder MS(APCI)m/z: 417/419[M + H]⁺ |
| 200 | H | 6-trifluoromethyl-2-chloro-3-methyl-pyridyl | colorless powder MS(APCI)m/z: 450/452[M + H]⁺ |

TABLE 28-continued

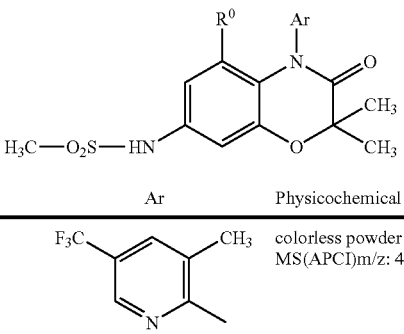

| Ex. Nos. | R⁰ | Ar | Physicochemical properties etc. |
|---|---|---|---|
| 201 | H | 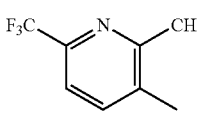 | colorless powder<br>MS(APCI)m/z: 430[M + H]⁺ |
| 202 | H | 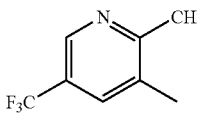 | colorless powder<br>MS(APCI)m/z: 430[M + H]⁺ |
| 203 | H | 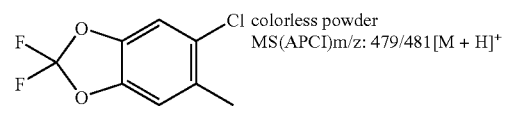 | colorless powder<br>MS(APCI)m/z: 430[M + H]⁺ |
| 204 | F | 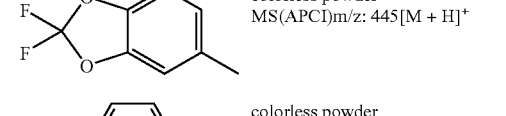 | colorless powder<br>MS(APCI)m/z: 479/481[M + H]⁺ |
| 205 | F |  | colorless powder<br>MS(APCI)m/z: 445[M + H]⁺ |
| 206 | 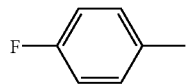 | 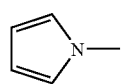 | colorless powder<br>MS(APCI)m/z: 405[M + H]⁺ |
| 207 | H | 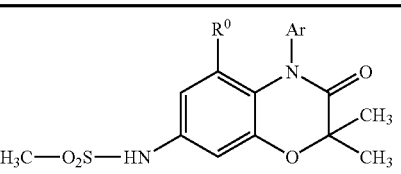 | yellow powder<br>MS(APCI)m/z: 336[M + H]⁺ |

Examples 208

The corresponding starting materials were treated in the same manner as described in Example 1 to give N-[4-(4-fluorophenyl)-2-methyl-3-oxo-2-phenyl-3,4-dihydro-2H-1,4-benzoxazin-7-yl]methanesulfonamide as a colorless powder.

MS (APCI) m/z: 427 [M+H]⁺

Examples 209 to 214

The corresponding starting materials were treated in the same manner as described in Example 1 to give compounds shown in the following Table 29.

TABLE 29

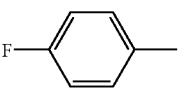

| Ex. Nos. | R⁰ | Ar | Physicochemical properties etc. |
|---|---|---|---|
| 209 | H |  | colorless powder<br>MS(APCI)m/z: 404[M + H]⁺ |
| 210 | CF₃ |  | colorless powder<br>MS(APCI)m/z: 433[M + H]⁺ |

TABLE 29-continued

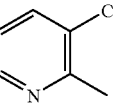

| Ex. Nos. | R⁰ | Ar | Physicochemical properties etc. |
|---|---|---|---|
| 211 | F | 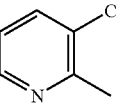 | colorless powder MS(APCI)m/z: 458/460[M + H]⁺ |
| 212 | F | 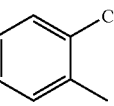 | colorless powder MS(APCI)m/z: 448[M + H]⁺ |
| 213 | F | 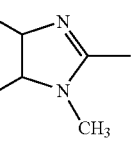 | colorless powder MS(APCI)m/z: 413/415[M + H]⁺ |
| 214 | H |  | colorless solid MS(APCI)m/z: 401[M + H]⁺ |

Reference Example 1

(1) To a suspension of potassium fluoride (4.71 g) in N,N-dimethylformamide (40 mL) was added 2-amino-5-nitrophenol (5.00 g), and the mixture was stirred at room temperature for 1 hour. To the suspension was added dropwise a solution of ethyl α-bromoisobutyrate (6.33 g) in N,N-dimethylformamide (10 mL) over a period of 20 minutes, and the mixture was stirred at 60° C. for 20 hours. After cooling, to the reaction mixture was added cool, water and the mixture was extracted with ethyl acetate. The organic layer was washed successively with an aqueous 10% HCl solution, water and brine, dried over sodium sulfate and concentrated in vacuo. The resultant residue was suspended in ethyl acetate, and the precipitates were collected by filtration and washed with ethyl acetate to give 2,2-dimethyl-7-nitro-2H-1,4-benzoxazin-3(4H)-one (2.80 g) as a pale brown powder.
ESI-MS m/z: 221 [M−H]⁻

(2) To a suspension of the compound obtained in the above step (1) (600 mg) in dichloromethane (12 mL) were added phenylboronic acid (659 mg), copper(II) acetate (589 mg) and Molecular sieves-4A powder (600 mg), and thereto was added triethylamine (753 μL). The mixture was vigorously stirred at room temperature for 20 hours. The reaction mixture was filtered and the residue was washed with chloroform. The filtrate and the washings were combined, concentrated in vacuo and purified by column chromatography on silica gel (solvent; n-hexane/ethyl acetate=9/1) to give 2,2-dimethyl-7-nitro-4-phenyl-2H-1,4-benzoxazin-3(4H)-one (755 mg) as a pale yellow solid.
MS (APCI) m/z: 316 [M+NH₄]⁺

(3) To a suspension of the compound obtained in the above step (2) (150 mg) in ethanol (6 mL) was added tin(II) chloride dihydrate (567 mg), and the mixture was stirred at 80° C. for 3 hours. After cooling, to the reaction mixture were added an aqueous saturated sodium hydrogencarbonate solution and ethyl acetate, and the mixture was stirred at room temperature for 1 hour. The reaction mixture was filtered through a celite pad, and filtrate was extracted with ethyl acetate. The organic layer was washed with brine, dried over sodium sulfate and concentrated in vacuo. The resultant residue was purified by column chromatography on NH-silica gel (solvent; n-hexane/ethyl acetate=4/1) to give 7-amino-2,2-dimethyl-4-phenyl-2H-1,4-benzoxazin-3(4H)-one (113 mg) as a colorless powder.
MS (APCI) m/z: 269 [M+H]⁺

Reference Example 2

(1) To a solution of the compound obtained in Reference Example 1(1) (200 mg) in N,N-dimethylformamide (3 mL) was added sodium hydride (60% dispersion in mineral oil, 43 mg) under ice cooling, and the mixture was stirred at room temperature for 0.5 hour. To the reaction mixture was added dropwise benzyl bromide (128 μL) under ice-cooling, and the mixture was stirred at room temperature for 3 hours. To the reaction mixture was added cold water, and the mixture was extracted with ethyl acetate. The organic layer was washed successively with water and brine, dried over sodium sulfate and concentrated in vacuo. The resultant residue was purified by column chromatography on NH-silica gel (solvent; n-hexane/ethyl acetate=9/1→4/1) to give 4-benzyl-2,2-dimethyl-7-nitro-2H-1,4-benzoxazin-3(4H)-one (216 mg) as a yellow powder.

(2) The compound obtained in the above step (1) (150 mg) was treated in the same manner as described in Reference Example 1(3) to give 7-amino-4-benzyl-2,2-dimethyl-2H-1,4-benzoxazin-3(4H)-one (102 mg) as a colorless powder.
MS (APCI) m/z: 283 [M+H]⁺

Reference Example 3

(1) To a solution of the compound obtained in Reference Example 1(1) (500 mg) in tetrahydrofuran (7 mL)-methanol (5 mL) was added 10% palladium-carbon (100 mg, water content: ca. 50%), and the mixture was stirred overnight at room temperature under atmospheric pressure of hydrogen. The insolubles were removed by filtration, and the filtrate was concentrated in vacuo to give 7-amino-2,2-dimethyl-2H-1,4-benzoxazin-3(4H)-one (429 mg) as a pale pink solid.
MS (APCI) m/z: 193 [M+H]⁺

(2) A mixture of the compound obtained in the above step (1) (43 mg), 2-bromo-5-fluoropyridine (79 mg), copper(I) iodide (4.3 mg), potassium phosphate (96 mg) and N,N'-dimethylethylenediamine (5 μL) was stirred in dioxane (2 mL) at 110° C. for 3 hours under argon atmosphere. To the reaction mixture were added copper(I) iodide (12.9 mg) and N,N'-dimethylethylenediamine (15 μL), and the mixture was stirred at the same temperature for 0.5 hour. After cooling, to the reaction mixture was added water, and the mixture was extracted with ethyl acetate. The organic layer was washed with brine, dried over magnesium sulfate and concentrated in vacuo. The resultant residue was purified by column chromatography on silica gel (solvent; n-hexane/ethyl acetate=9/1→1/1) to give 7-amino-4-(5-fluoropyridin-2-yl)-2,2-dimethyl-2H-1,4-benzoxazin-3(4H)-one (55 mg) as a pale orange powder.
MS (APCI) m/z: 288 [M+H]⁺

Reference Example 4

(1) The corresponding starting materials were treated in the same manner as described in Reference Example 1(1) to give 7-nitro-2H-1,4-benzoxazin-3(4H)-one (ESI-MS m/z: 193 [M−H]⁻), and then the compound was treated in the same manner as described in Reference Example 3(1) to give 7-amino-2H-1,4-benzoxazin-3(4H)-one as a pale brown powder.
MS (APCI) m/z: 165 [M+H]⁺

(2) To a solution of the compound obtained in the above step (1) (200 mg) in N,N-dimethylformamide (3 mL) was added sodium hydride (60% dispersion in mineral oil, 59 mg) under ice-cooling, and the mixture was stirred at room temperature for 15 minutes. To the reaction mixture was added dropwise benzyl bromide (160 µL) under ice-cooling, and the mixture was stirred at room temperature for 2 hours. To the reaction mixture was added cold water, and the mixture was extracted with ethyl acetate. The organic layer was washed successively with water and brine, dried over sodium sulfate and concentrated in vacuo. The resultant residue was purified by column chromatography on silica gel (solvent; n-hexane/ethyl acetate =5/1→1/1) to give 7-amino-4-benzyl-2H-1,4-benzoxazin-3(4H)-one (221 mg) as a yellow powder.
MS (APCI) m/z: 255 [M+H]⁺

Reference Example 5

(1) To a suspension of 2-amino-5-nitrophenol (3.00 g) in N,N-dimethylformamide (30 mL) was added potassium fluoride (3.40 g), and the mixture was stirred at room temperature for 15 minutes, and thereto was added 2-bromo-2-methylpropiophenone (4.42 g). The mixture was stirred at room temperature for 0.5 hour, at 60° C. for 20 hours and at 80° C. for 3 days. After cooling, to the reaction mixture was added cold water, and the mixture was extracted with ethyl acetate. The organic layer was washed successively with water and brine, dried over sodium sulfate and concentrated in vacuo. The resultant residue was purified by column chromatography on silica gel (solvent; n-hexane/ethyl acetate=10/1) to give 2,2-dimethyl-7-nitro-3-phenyl-2H-1,4-benzoxazine (3.65 g) as a pale yellow powder.
MS (APCI) m/z: 283 [M+H]⁺

(2) To a suspension of the compound obtained in the above step (1) (1.50 g) in methanol (15 mL) was added sodium borohydride (0.20 g) under ice-cooling, and the mixture was stirred at room temperature for 1 hour. To the reaction mixture was added an aqueous saturated sodium hydrogencarbonate solution, and the mixture was extracted with ethyl acetate. The organic layer was washed successively with water and brine, dried over sodium sulfate and concentrated in vacuo. The resultant residue was triturated with diethylether-n-hexane, and the precipitates were collected by filtration to give 2,2-dimethyl-7-nitro-3-phenyl-3,4-dihydro-2H-1,4-benzoxazine (1.06 g) as a pale yellow powder.
MS (APCI) m/z: 285 [M+H]⁺

(3) A mixture of the compound obtained in the above step (2) (200 mg), 4-bromo-fluorobenzene (116 µL), 2-dicyclohexylphosphino-2',4',6'-triisopropyl-1,1'-biphenyl (16.8 mg), tris(dibenzylideneacetone)dipalladium (6.4 mg), cesium carbonate (321 mg) and toluene (4 mL)-tert-butanol (0.8 mL) was stirred at 100° C. for 17 hours under argon atmosphere. After cooling, to the reaction mixture was added cold water, and the mixture was extracted with ethyl acetate. The organic layer was washed successively with water and brine, dried over sodium sulfate and concentrated in vacuo. The resultant residue was purified by column chromatography on silica gel (solvent; n-hexane/ethyl acetate=10/1→3/1) to give 4-(4-fluorophenyl)-2,2-dimethyl-7-nitro-3-phenyl-3,4-dihydro-2H-1,4-benzoxazine (186 mg) as a yellow powder.
MS (APCI) m/z: 379 [M+H]⁺

(4) To a suspension of the compound obtained in the above step (3) (265 mg) in ethanol (10 mL) was added tin(II) chloride dihydrate (790 mg) at room temperature, and the mixture was stirred at reflux for 6 hours. To the reaction mixture was added tin(II) chloride dihydrate (239 mg), and the mixture was refluxed for 2 hours. After cooling, to the reaction mixture was added a saturated sodium hydrogencarbonate solution and ethyl acetate, and the mixture was stirred at room temperature for 1 hour. The mixture was filtered, and the filtrate was extracted with ethyl acetate. The organic layer was washed with brine, dried over sodium sulfate and concentrated in vacuo. The resultant residue was purified by column chromatography on silica gel (solvent; n-hexane/ethyl acetate=10/1→1/1) to give 4-(4-fluorophenyl)-2,2-dimethyl-3-phenyl-3,4-dihydro -2H-1,4-benzoxazin-7-amine (219 mg) as a pale yellow gum.
MS (APCI) m/z: 349 [M+H]⁺

Reference Example 6

(1) The compound obtained in Reference Example 1(1) (200 mg) and 4-fluorophenylboronic acid (252 mg) were treated in the same manner as described in Reference Example 1(2) to give 4-(4-fluorophenyl)-2,2-dimethyl-7-nitro-2H-1,4-benzoxazin-3(4H)-one (220 mg) as a pale yellow solid.
MS (APCI) m/z: 334 [M+NH₄]⁺

(2) To a solution of the compound obtained in the above step (1) (300 mg) in tetrahydrofuran (10 mL) was added a solution of borane-dimethylsulfide complex in tetrahydrofuran (10 M, 0.38 mL) at room temperature, and the mixture was stirred at room temperature for 3 house and at 50° C. for 8 hours. After cooling, to the reaction mixture was gradually added methanol, and the mixture was refluxed under heating for 0.5 hour. The reaction mixture was concentrated in vacuo, and the resultant residue was purified by column chromatography on silica gel (solvent; n-hexane/ethyl acetate=10/1→4/1) to give 4-(4-fluorophenyl)-2,2-dimethyl-7-nitro-3,4-dihydro-2H-1,4-benzoxazine (273 mg) as a pale yellow powder.
MS (APCI) m/z: 303 [M+H]⁺

(3) The compound obtained in the above step (2) (200 mg) was treated in the same manner as described in Reference Example 5(4) to give 4-(4-fluorophenyl)-2,2-dimethyl-3,4-dihydro-2H-1,4-benzoxazin-7-amine (153 mg) as a colorless powder.
MS (APCI) m/z: 273 [M+H]⁺

Reference Example 7

(1) To a suspension of sodium hydride (60% dispersion in mineral oil, 0.68 g) in N,N-dimethylformamide (15 mL) was added dropwise a solution of 2-amino-5-bromopyridin-3-ol (3.22 g) in N,N-dimethylformamide (25 mL) at room temperature over a period of 10 minutes, and the mixture was stirred at room temperature for 20 minutes. To the mixture was added dropwise ethyl α-bromoisobutyrate (3.32 g) over a period of 20 minutes, and the reaction mixture was stirred at room temperature for 1 hour and at 80° C. for 2 hours. After cooling, to the reaction mixture was added cold water, and the mixture was extracted with ethyl acetate. The organic layer was washed successively water and brine, dried over magnesium sulfate and concentrated in vacuo by a half volume. The precipitates were collected by filtration to give 7-bromo-2,2-dimethyl-2H-pyrido[3,2-b][1,4]oxazin-3(4H)-one (0.90 g) was obtained as a powder.
MS (APCI) m/z: 257/279 [M+H]⁺

(2) The compound obtained in the above step (1) (500 mg) was treated in the same manner as described in Reference Example 1(2) to give 7-bromo-4-(4-fluorophenyl)-2,2-dimethyl-2H-pyrido[3,2-b][1,4]oxazin-3(4H)-one (477 mg) as a colorless powder.
MS (APCI) m/z: 351/353 [M+H]$^+$ (3) A mixture of palladium acetate (12 mg), 2-dicyclohexylphosphino-2',4',6'-triisopropyl-1,1'-biphenyl (63 mg), phenylboronic acid (6 mg) and tert-butanol (8 mL) was stirred at room temperature for 20 minutes under argon atmosphere. To the reaction mixture were added the compound obtained in the above step (2) (460 mg), potassium carbonate (543 mg), tert-butyl carbamate (307 mg) and tert-butanol (20 mL), and the mixture was refluxed under heating for 3 hours. After cooling, to the reaction mixture was added ethyl acetate, and the mixture was washed successively with Water and brine, dried over magnesium sulfate and concentrated in vacuo. The resultant residue was purified by column chromatography on NH-silica gel (Chromatorex NH-silica gel, solvent; n-hexane/ethyl acetate=9/1→7/3) to give tert-butyl 4-(4-fluorophenyl)-2,2-dimethyl-3-oxo-3,4-dihydro-2H-pyrido[3,2-b][1,4]oxazin-7-yl]carbamate.

(4) To a solution of the compound obtained in the above step (3) in chloroform (10 mL) was added 4 HCl-ethyl acetate solution (15 mL), and the mixture was stirred at room temperature for 2 hours. To the reaction mixture was added an aqueous saturated sodium hydrogencarbonate solution, and the mixture was extracted with ethyl acetate. The organic layer was dried over magnesium sulfate and concentrated in vacuo to give 7-amino-4-(4-fluorophenyl)-2,2-dimethyl-2H-pyrido[3,2-b][1,4]oxazin-3(4H)-one (129 mg) as a colorless powder.
MS (APCI) m/z: 288 [M+H]$^+$ Reference Examples 8 to 19

The corresponding materials were treated in the same manner as described in Reference Example 1 to give compounds shown in the following Tables 30 to 31.

TABLE 30

| Ref. Ex. Nos. | Ar | R$^3$ | Physicochemical properties etc. |
|---|---|---|---|
| 8 | phenyl | phenyl | MS(APCI)m/z: 317[M + H]$^+$ |
| 9 | 3-fluorophenyl | phenyl | MS(APCI)m/z: 335[M + H]$^+$ |
| 10 | 2-fluorophenyl | phenyl | MS(APCI)m/z: 335[M + H]$^+$ |
| 11 | 4-chlorophenyl | phenyl | MS(APCI)m/z: 351/353[M + H]$^+$ |
| 12 | 4-fluorophenyl | H | MS(APCI)m/z: 259[M + H]$^+$ |
| 13 | 4-fluorophenyl | CH$_3$ | MS(APCI)m/z: 273[M + H]$^+$ |

TABLE 31

| Ref. Ex. Nos. | Ar—Q— | Physicochemical properties etc. |
|---|---|---|
| 14 | 4-fluorophenyl | MS(APCI)m/z: 287[M + H]$^+$ |
| 15 | 3,4-difluorophenyl | MS(APCI)m/z: 305[M + H]$^+$ |

TABLE 31-continued

![structure: benzoxazinone with H2N on ring, N-O-Ar, two CH3 groups]

| Ref. Ex. Nos. | Ar—Q— | Physicochemical properties etc. |
|---|---|---|
| 16 | Cl—C6H4— | MS(APCI)m/z: 303/305[M + H]⁺ |
| 17 | F,Cl-disubstituted phenyl | MS(APCI)m/z: 321/323[M + H]⁺ |
| 18 | H3CO—C6H4— | MS(APCI)m/z: 299[M + H]⁺ |
| 19 | F-pyridinyl | MS(APCI)m/z: 288[M + H]⁺ |

Reference Examples 20 to 22

(1) The corresponding materials were treated in the same manner as described in Reference Example 1(1) to (2) to give compounds shown in the following compounds.

Reference Example 20(1): 4-(4-fluorophenyl)-7-nitro-2-phenyl-2H-1,4-benzoxazin-3(4H)-one, MS (APCI) m/z: 382 [M+NH₄]⁺

Reference Example 21(1): 4-(4-fluoro-3-methylphenyl)-2,2-dimethyl-7-nitro-2-phenyl-2H-1,4-benzoxazin-3(41)-one pale yellow powder
MS (APCI) m/z: 331 [M+H]⁺

Reference Example 22(1): 2,2-dimethyl-7-nitro-4-[(E)-2-phenylvinyl]-2H-1,4-benzoxazin-3(4H)-one
MS (APCI) m/z: 325 [M+H]⁺

(2) The compounds obtained in the above step (1) were treated in the same manner as described in Reference Example 1(3) to give the following compounds.

Reference Example 20(2): 7-amino-4-(4-fluorophenyl)-2-phenyl-2H-1,4-benzoxazin-3(4H)-one
MS (APCI) m/z: 335 [M+H]⁺

Reference Example 21(2): 7-amino-4-(4-fluoro-3-methylphenyl)-2,2-dimethyl -2H-1,4-benzoxazin-3(4H)-one, MS (APCI) m/z: 301 [M+H]⁺

Reference Example 22(2): 7-amino-2,2-dimethyl-4-[(E)-2-phenylvinyl]-2H-1,4-benzoxazin-3(4H)-one, MS (APCI) m/z: 295 [M+H]⁺

Reference Example 23

(1) The corresponding starting materials were treated in the same manner as described in Reference Example 1(1) to (2) to give 6-chloro-2,2-dimethyl-7-nitro-4-fluorophenyl-2H-1,4-benzoxazin-3(4H)-one as a yellow powder.
MS (APCI) m/z: 368/370 [M+NH₄]⁺

(2) The compound obtained in the above step (1) was treated in the same manner as described in Reference Example 1(3) to give 7-amino-6-chloro-2,2-dimethyl -4-fluorophenyl-2H-1,4-benzoxazin-3(4H)-one as a pale red powder.
MS (APCI) m/z: 321/323 [M+H]⁺

Reference Example 24

(1) The corresponding starting materials were treated in the same manner as described in Reference Example 2(1) to give 4-benzyl-2-(4-chlorophenyl)-7-nitro-2H -1,4-benzoxazin-3(4H)-one as a pale yellow powder.

(2) The compound obtained in the above step (1) was treated in the same manner as described in Reference Example 1(3) to give 7-amino-4-benzyl-2-(4-chlorophenyl)-2H-1,4-benzoxazin-3(4H)-one as a pale yellow powder.
MS (APCI) m/z: 365/367 [M+H]⁺

Reference Examples 25 to 27

The corresponding starting materials were treated in the same manner as described in Reference Example 2 to give compounds shown in the following Table 32.

TABLE 32

![structure: benzoxazinone with H2N, N-Q-Ar, R² and R³ substituents]

| Ref. Ex. Nos. | Ar—Q— | R² | R³ | Physicochemical properties etc. |
|---|---|---|---|---|
| 25 | benzyl (C6H5-CH2-) | H | phenyl | MS(APCI)m/z: 331[M + H]⁺ |
| 26 | 4-F-C6H4-CH2- | CH₃ | CH₃ | MS(APCI)m/z: 301[M + H]⁺ |

TABLE 32-continued

| Ref. Ex. Nos. | Ar—Q— | $R^2$ | $R^3$ | Physicochemical properties etc. |
|---|---|---|---|---|
| 27 | PhCH₂CH₂— | CH₃ | CH₃ | MS(APCI)m/z: 297[M + H]⁺ |

Reference Example 28

(1) A solution of 6-nitrobenzothiazole (5.00 g) and hydrazine hydrate (10 mL) in ethanol (50 mL) was refluxed for 2 hours. One third volume of the reaction mixture was separated and evaporated in vacuo. The residue was diluted with ethanol (20 mL), and thereto was added a solution of α-bromoisobutyric acid (5.51 g), sodium hydroxide (0.4 g) and water (2 mL), and the mixture was refluxed for 2 hours. The reaction mixture was concentrated in vacuo, and to the residue was added diluted acetic acid (5 mL), and the mixture was heated at 50° C. for 1 hour. After cooling, the precipitates were collected by filtration, washed successively with water and ethanol and recrystallized from ethyl acetate to give 2,2-dimethyl-7-nitro-2H-1,4-benzothiazin -3(4H)-one (0.63 g) as pale yellow crystals.
ESI-MS m/z: 237 [M−H]⁻

(2) The compound obtained in the above step (1) (310 mg) was treated in the same manner as described in Reference Example 1(2) to give 4-(4-fluorophenyl)-2,2-dimethyl-7-nitro-2H-1,4-benzothiazin-3(4H)-one (221 mg) as an orange solid.
MS (APCI) m/z: 333 [M+H]⁺

(3) The compound obtained in the above step (2) (218 mg) was treated in the same manner as described in Reference Example 1(3) to give 7-amino-4-(4-fluorophenyl)-2,2-dimethyl-2H-1,4-benzothiazin-3(4H)-one (126 mg) as a pale pink powder.
MS (APCI) m/z: 303 [M+H]⁺

Reference Example 29

(1) To a solution of 1,2-phenylenediamine (16.96 g) in N,N-dimethylformamide (80 ml) were added successively N,N-diisopropylethylamine (36.4 mL) and ethyl α-bromoisobutyrate (39.8 g), and the mixture was heated at 110° C. for 3 days. After cooling, to the reaction mixture was added cold water and the mixture was extracted with ethyl acetate. The aqueous layer was extracted with ethyl acetate, and the combined organic layer was washed successively with an aqueous 10% HCl solution, water, an aqueous saturated sodium hydrogencarbonate solution and brine, dried over sodium sulfate and concentrated in vacuo. The resultant residue was recrystallized from dichloromethane-n-hexane to give 3,3-dimethyl-3,4-dihydroquinoxalin-2(1H)-one (15.90 g) as pale yellow crystals.
MS (APCI) m/z: 177 [M+H]⁺

(2) A solution of the compound obtained in the above step (1) (300 mg) in concentrated sulfuric acid (12 mL) was cooled to −15° C., and thereto was added dropwise a solution of nitric acid (44 μL) in concentrated sulfuric acid (0.6 mL). The mixture was stirred at the same temperature for 3 hours. To the reaction mixture was added sodium hydroxide (5.4 g) and ice, and the mixture was extracted with ethyl acetate. The organic layer was washed successively with water and brine, dried over sodium sulfate and concentrated in vacuo. The resultant residue was suspended in ethyl acetate-diethylether, and the precipitates were collected by filtration. The resultant solid was purified by column chromatography on NH-silica gel (Chromatorex NH-silica gel, solvent; n-hexane/ethyl acetate=4/1→1/4) to give 3,3-dimethyl-6-nitro-3,4-dihydroquinoxalin-2(1H)-one (26 mg) as a yellow powder.
MS (APCI) m/z: 222 [M+H]⁺

(3) The compound obtained in the above step (2) (717 mg) was treated in the same manner as described in Reference Example 1(2) to give 1-(4-fluorophenyl)-3,3-dimethyl-6-nitro-3,4-dihydroquinoxalin-2(1H)-one (346 mg) as a yellow powder.
MS (APCI) m/z: 316 [M+H]⁺

(4) The compound obtained in the above step (3) (170 mg) was treated in the same manner as described in Reference Example 1(3) to give 6-amino-1-(4-fluorophenyl)-3,3-dimethyl-3,4-dihydroquinoxalin-2(1H)-one (114 mg) as a colorless powder.
MS (APCI) m/z: 286 [M+H]⁺

Reference Example 30

The corresponding starting materials were treated in the same manner as described in Reference Example 3 to give 7-amino-4-(5-chloro-2-thienyl)-2,2-dimethyl -2H-1,4-benzoxazin-3(4H)-one.
MS (APCI) m/z: 309/311 [M+H]⁺

Reference Example 31

The corresponding starting materials were treated in the same manner as described in Reference Example 28 to give 7-amino-4-(4-fluorophenyl)-2H-1,4-benzothiazin-3(4H)-one.
MS (APCI) m/z: 275 [M+H]⁺

Reference Examples 32 to 45

The corresponding materials were treated in the same manner as described in Reference Example 1 to give compounds shown in the following Tables 33 to 34.

TABLE 33

| Ref. Ex. Nos. | Ar | R²/R³ | Physicochemical properties etc. |
|---|---|---|---|
| 32 | 3-thienyl | C(CH₃)₂ (t-Bu, with one CH₃ implicit) | MS(APCI)m/z: 275[M + H]⁺ |
| 33 | 4-F, 3-CF₃-phenyl | C(CH₃)₂ | MS(APCI)m/z: 355[M + H]⁺ |
| 34 | 4-F-phenyl | CH(CH₃)-CH(CH₃) | MS(APCI)m/z: 301[M + H]⁺ |
| 35 | 4-F-phenyl | 1-methylcyclobutyl | MS(APCI)m/z: 299[M + H]⁺ |
| 36 | 4-F-phenyl | CH(iPr)(C₂H₅) | MS(APCI)m/z: 287[M + H]⁺ |

TABLE 34

| Ref. Ex. Nos. | Ar | R' | R² | R³ | Physicochemical properties etc. |
|---|---|---|---|---|---|
| 37 | 4-F-phenyl | H | CH₃ | EtOCO— | MS(APCI)m/z: 345 [M + H]⁺ |
| 38 | 3-CH₃, 4-F-phenyl | H | H | H | MS(APCI)m/z: 273 [M + H]⁺ |
| 39 | 3-Cl, 4-F-phenyl | H | H | H | MS(APCI)m/z: 293/295[M + H]⁺ |
| 40 | 4-Br-phenyl | H | CH₃ | CH₃ | MS(APCI)m/z: 347/349[M + H]⁺ |

TABLE 34-continued

Structure: benzoxazinone with H$_2$N- group, R' substituent, Ar on N, R$^2$ and R$^3$ on carbon adjacent to O, C=O at position 3.

| Ref. Ex. Nos. | Ar | R' | R$^2$ | R$^3$ | Physicochemical properties etc. |
|---|---|---|---|---|---|
| 41 | 2,5-dimethylphenyl (H$_3$C, CH$_3$) | H | CH$_3$ | CH$_3$ | MS(APCI)m/z: 297 [M + H]$^+$ |
| 42 | 3,4-dichlorophenyl (Cl, Cl) | H | CH$_3$ | CH$_3$ | MS(APCI)m/z: 337/339[M + H]$^+$ |
| 43 | 3,4-difluorophenyl (F, F) | F | CH$_3$ | CH$_3$ | MS(APCI)m/z: 305 [M + H]$^+$ |
| 44 | 4-fluorophenyl (F) | H | H | F | Note 1 |
| 45 | 3-chloro-4-methylphenyl (Cl, H$_3$C) | H | CH$_3$ | CH$_3$ | MS(APCI)m/z: 317/319[M + H]$^+$ |

Et: ethyl group
Note 1:
The compound was used as a starting material in the following step without further purification.

Reference Example 46

(1) The corresponding starting materials were treated in the same manner as described in Reference Example 1(1) to (2) to give 4-(3-chloro-4-methylphenyl)-2,2-dimethyl-7-nitro-2H-1,4-benzoxazin-3(4H)-one as a pale yellow powder.
MS (APCI) m/z: 347/349 [M+H]$^+$ (2) The compound obtained in the above step (1) (110 mg) was treated in the same manner as described in Reference Example 1(3) to give 7-amino-4-(3-chloro-4-methylphenyl)-2,2-dimethyl-2H-1,4-benzoxazin-3(4H)-one (100 mg) as a colorless viscous oil.
MS (APCI) m/z: 317/319 [M+H]$^+$

Reference Example 47

(1) The corresponding starting materials were treated in the same manner as described in Reference Example 2(1) to give 2,2-dimethyl-7-nitro-4-(1-phenylethyl) -2H-1,4-benzoxazin-3(4H)-one as a pale yellow viscous oil.
MS (APCI) m/z: 327 [M+H]$^+$ (2) The compound obtained in the above step (1) (200 mg) was treated in the same manner as described in Reference Example 2(2) to give 7-amino-2,2-dimethyl-4-(1-phenylethyl)-2H-1,4-benzoxazin-3(4H)-one (123 mg) as a pale brown powder.
MS (APCI) m/z: 297 [M+H]$^+$

Reference Example 48

(1) To a solution of methyl 2,2-dimethyl-3-oxo-3,4-dihydro-2H-1,4-benzoxazin -7-carboxylate (1.00 g) in tetrahydrofuran (50 mL) was added dropwise 1M diisobutyl aluminum hydride solution in toluene (13.1 mL) under cooling in dry ice/acetone bath under argon atmosphere, and the mixture was stirred at the same temperature for 2.5 hours. Thereto was further added 1M diisobutyl aluminum hydride solution in toluene (8.5 mL), and the mixture was stirred at the same temperature for 1.5 hours. The reaction mixture was poured to an aqueous 2N HCl solution, and the mixture was extracted with diethylether. The organic layer was washed successively with an aqueous saturated sodium hydrogencarbonate solution and brine, dried over sodium sulfate and concentrated in vacuo. The residue was triturated in ethyl acetate to give 7-(hydroxymethyl)-2,2-dimethyl-2H-1,4-benzoxazin-3 (4H)-one (389 mg) as a colorless powder.
MS (APCI) m/z: 222 [M+H+CH$_3$OH–H$_2$O]$^+$ (2) To a solution of the compound obtained in the above step (1) (388 mg) and N-(tert-butoxycarbonyl)methanesulfonamide (548 mg) in toluene (10 mL) was added cyanomethylene tri-n-butylphosphorane (678 mg), and the mixture was stirred at 50° C. for 8 hours. To the reaction mixture was further added cyanomethylene tri-n-butylphosphorane (678 mg), and the mixture was stirred at 80° C. for 18 hours. To the reaction mixture was added an aqueous saturated sodium hydrogencarbonate solution, and the mixture was extracted with ethyl acetate. The organic layer was washed with brine, dried over sodium sulfate and concentrated in vacuo. The residue was purified by column chromatography on silica gel (solvent, n-hexane/ethyl acetate=4/1→1/1) and triturated with diisopropylether to give tert-butyl [(2,2-dimethyl-3-oxo-3,4-dihydro-2H-1,4-benzoxazin-7-yl)methyl](methylsulfonyl)carbamate (217 mg) as a colorless powder.
MS (APCI) m/z: 402 [M+NH$_4$]$^+$ Reference Example 49

(1) 6-bromo-3,3-dimethylquinolin-2,4-(1H,3H)-dione (1.0 g) and 4-fluorophenyl-boronic acid (1.04 g) were treated in the same manner as described in Reference Example 1(2) to obtain 6-bromo-1-(4-fluorophenyl)-3,3-dimethylquinolin-2,4-(1H,3H)-dione (1.02 g) as a colorless solid.
MS (APCI) m/z: 362/364 [M+H]$^+$ (2) The compound obtained in the above step (1) (650 mg) was treated in the same manner as described in Reference Example 7(3) to give tert-butyl [1-(4-fluorophenyl)-3,3-dimethyl-2,4-dioxo-1,2,3,4-tetrahydroquinolin-6-yl]carbamate (209 mg) as a pale yellow powder.
MS (APCI) m/z: 399 [M+H]$^+$ (3) The compound obtained in the above step (2) (570 mg) was treated in the same manner as described in Reference Example 7(4) to give 6-amino-1-(4-fluorophenyl)-3,3-dimethylquinolin-2,4(1H,3H)-dione (342 mg) as a yellow powder.
MS (APCI) m/z: 299 [M+H]$^+$ (4) The compound obtained in the above step (3) (150 mg) was treated in the same manner as described in Example 1 to give N-[1-(4-fluorophenyl)-3,3-dimethyl-2,4-dioxo-1,2,3,4-tetrahydroquinolin-6-yl]methanesulfonamide (173 mg) as a pale yellow powder.
MS (APCI) m/z: 377 [M+H]$^+$ Reference Example 50

(1) 2-amino-4-chloro-5-nitrophenol (10.0 g) and ethyl α-bromoisobutyrate (7.4 mL) were treated in the same manner as described in Reference Example 1(1) to give 6-chloro-2,2-dimethyl-7-nitro-2H-1,4-benzoxazin-3(4H)-one (6.82 g) as a pale brown powder.
MS (APCI) m/z: 255/257 [M−H]$^-$ (2) The compound obtained in the above step (1) (6.82 g) and 4-fluorophenylboronic acid (7.44 g) were treated in the same manner as described in Reference Example 1(2) to give 6-chloro-4-(4-fluorophenyl)-2,2-dimethyl-7-nitro-2H-1,4-benzoxazin-3(4H)-one (6.22 g) as a pale yellow powder.
MS (APCI) m/z: 368/370 [M+NH$_4$]$^+$ (3) The compound obtained in the above step (2) (300 mg) was treated in the same manner as described in Example 43 to give tert-butyl [4-(4-fluorophenyl)-2,2-dimethyl-7-nitro-3-oxo-3,4-dihydro-2H-1,4-benzoxazin-6-yl]carbamate (63 mg) as a yellow solid.
MS (APCI) m/z: 432 [M+H]$^+$ (4) The compound obtained in the above step (3) (150 mg) was treated in the same manner as described in Reference Example 1(3) to give tert-butyl [7-amino-4-(4-fluorophenyl)-2,2-dimethyl-3-oxo-3,4-dihydro-2H-1,4-benzoxazin-6-yl]carbamate (78 mg) as a colorless powder.
MS (APCI) m/z: 402 [M+H]$^+$ Reference Example 51

(1) To a mixture of 6-chloro-4-(4-fluorophenyl)-2,2-dimethyl-7-nitro-2H-1,4-benzoxazin-3(4H)-one (compound obtained in Reference Example 50(2); 200 mg), potassium carbonate (236 mg), tetrakis(triphenylphosphine)palladium (0) (66 mg) and dioxane (2 mL) was added trimethylboroxin (80 μL) under argon atmosphere, and the mixture was refluxed under heating for 18 hours. After cooling, the reaction mixture was filtered through a celite pad, and the insolubles were washed with tetrahydrofuran. The filtrate and the washings were combined and concentrated in vacuo. The resultant residue was purified by column chromatography on silica gel (solvent; n-hexane/ethyl acetate=9/1) to give 4-(4-fluorophenyl)-2,2,6-trimethyl-7-nitro-2H-1,4-benzoxazin-3(4H)-one (10 mg) as a pale yellow powder.
MS (APCI) m/z: 331 [M+H]$^+$ (2) The compound obtained in the above step (1) (122 mg) was treated in the same manner as described in Reference Example 1(3) to give 7-amino-4-(4-fluorophenyl)-2,2,6-trimethyl-2H-1,4-benzoxazin-3(4H)-one (28 mg) as a colorless powder.
MS (APCI) m/z: 301 [M+H]$^+$ Reference Example 52

(1) A mixture of 6-chloro-4-(4-fluorophenyl)-2,2-dimethyl-7-nitro-2H-1,4-benzoxazin-3(4H)-one (compound obtained in Reference Example 50(2); 400 mg), palladium acetate (5.1 mg), racemic 2-(di-tert-butylphosphino)-1,1'-binaphthyl (11.4 mg), cesium carbonate (557 mg), methanol (1 mL) and toluene (4 mL) was stirred at 70° C. under argon atmosphere for 26 hours. After cooling, to the reaction mixture was added water, and the mixture was extracted with ethyl acetate. The organic layer was washed with brine, dried over sodium sulfate and concentrated in vacuo. The resultant residue was suspended in chloroform (4 mL) and thereto was added 1-hydroxybenzotriazole (154 mg) and 1-ethyl-3-(3-dimethylaminopropyl)carbodiimide hydrochloride (208 mg). The mixture was stirred at room temperature for 3 hours. To the reaction mixture was added water, and the mixture was extracted with chloroform. The organic layer was washed successively with an aqueous saturated sodium hydrogencarbonate solution and brine, dried over sodium sulfate and concentrated in vacuo. The residue was purified by column chromatography on NH-silica gel (Chromatorex NH-silica gel; solvent; n-hexane/ethyl acetate=9/1) to give 4-(4-fluorophenyl)-6-methoxy-2,2-dimethyl-7-nitro-2H-1,4-benzoxazin-3(4H)-one (147 mg) as a pale yellow powder.
MS (APCI) m/z: 347 [M+H]$^+$ (2) The compound obtained in the above step (1) (130 mg) was treated in the same manner as described in Reference Example 1(3) to give 7-amino-4-(4-fluorophenyl)-6-methoxy-2,2-dimethyl-2H-1,4-benzoxazin-3(4H)-one (110 mg) as a colorless powder.
MS (APCI) m/z: 317 [M+H]$^+$ Reference Example 53

(1) To a solution of 2-amino-5-nitrophenol (4.62 g) in N,N-dimethylformamide (150 no) was added potassium carbonate (12.44 g), and thereto was added dropwise chloromethylmethylether (2.73 mL). The mixture was stirred at room temperature for 2.5 hours. The reaction mixture was diluted with ethyl acetate and washed successively with water and brine. The organic layer was dried over magnesium sulfate and concentrated in vacuo. The resultant residue was purified by column chromatography on NH-silica gel (Chromatorex NH-silica gel; solvent; n-hexane/ethyl acetate=2/1) to give

[2-(methoxymethoxy)-4-nitrophenyl]amine (4.76 g) as a yellow oil.
MS (APCI) m/z: 199 [M+H]+

(2) To a solution of the compound obtained in the above step (1) (3.00 g) in chloroform (130 mL) was added N-bromosuccinimide (4.04 g), and the mixture was stirred at room temperature for 30 minutes. The reaction mixture was diluted with chloroform, washed successively with water, an aqueous saturated sodium hydrogencarbonate solution and brine, and dried over magnesium sulfate. The organic layer was filtered through a NH-silica gel pad (Chromatorex NH-silica gel) and a celite pad, and the filtrate was concentrated in vacuo. The residue was purified by column chromatography on silica gel (solvent; n-hexane/ethyl acetate=19/1→1/1) and triturated with n-hexane/diisopropylether to give [2-bromo-6-(methoxymethoxy)-4-nitrophenyl]-amine (2.19 g) as an orange powder.
ESI-MS m/z: 275/277 [M−H]−

(3) To a solution of the compound obtained in the above step (2) (1.51 g) and pyridine (0.89 mL) in chloroform (40 mL) was added dropwise 2-bromo-2-methylpropionyl bromide (1.35 mL) under ice-cooling, and the mixture was stirred at room temperature for 24 hours. The reaction mixture was diluted with chloroform, washed successively with water, an aqueous saturated sodium hydrogencarbonate solution and brine, dried over magnesium sulfate and concentrated in vacuo. The resultant residue was purified by column chromatography on silica gel (solvent; n-hexane/ethyl acetate=4/1) to give 2-bromo-N-[2-bromo-6-(methoxymethoxy)-4-nitrophenyl]-2-methylpropionamide (1.81 g) as an orange oil.
MS (ESI) m/z: 423/425 [M−H]−

(4) To a solution of the compound obtained in the above step (3) (1.43 g) in dichloromethane (100 mL) was added trifluoroacetic acid (4 mL), and the mixture was stirred at room temperature for 2 hours. The reaction mixture was diluted with dichloromethane, washed successively with water and brine, dried over magnesium sulfate and concentrated in vacuo. The resultant residue was purified by column chromatography on silica gel (solvent; n-hexane/ethyl acetate=17/3→1/1) to give 2-bromo-N-(2-bromo-6-hydroxy-4-nitrophenyl)-2-methylpropionamide (1.09 g) as a pale yellow powder.
ESI-MS m/z: 379/381/383 [M−H]−

(5) To a solution of the compound obtained in the above step (4) (1.09 g) in N,N-dimethylformamide (40 mL) was added potassium carbonate (1.19 g), and the mixture was stirred at 50° C. for 17 hours. After cooling, the reaction mixture was diluted with ethyl acetate and washed successively with water and brine. The organic layer was dried over magnesium sulfate and concentrated in vacuo. The resultant residue was triturated with diisopropylether to give 5-bromo-2,2-dimethyl-7-nitro-2H -1,4-benzoxazin-3(4H)-one (0.79 g) as a colorless powder.
ESI-MS m/z: 299/301 [M−H]−

(6) The compound obtained in the above step (5) (570 mg) and 4-fluorophenylboronic acid (529 mg) were treated in the same manner as described in Reference Example 1(2) to give 5-bromo-4-(4-fluorophenyl)-2,2-dimethyl-7-nitro-2H-1,4-benzoxazin-3(4H)-one (306 mg) as a pale yellow powder.
MS (APCI) m/z: 395/397 [M+H]+

(7) The compound obtained in the above step (6) (305 mg) was treated in the same manner as described in Reference Example 1(3) to give 7-amino-5-bromo-4-(4-fluorophenyl)-2,2-dimethyl-2H-1,4-benzoxazin-3(4H)-one (218 mg) as a pale yellow powder.
MS (APCI) m/z: 365/367 [M+H]+

Reference Example 54

(1) The compound obtained in the Reference Example 53(1) (3.39 g) and N-chlorosuccinimide (3.43 g) were treated in the same manner as described in Reference Example 53(2), and then the resultant product (1.76 g) was treated in the same manner as described in Reference Example 53(3) to (5) to give 5-chloro-2,2-dimethyl-7-nitro -2H-1,4-benzoxazin-3(4H)-one (0.85 g) as a colorless powder.
ESI-MS m/z: 255/257 [M−H]−

(2) The compound obtained in the above step (1) (134 mg) and 4-fluorophenylboronic acid (292 mg) were treated in the same manner as described in Reference Example 1(2) to give 5-chloro-4-(4-fluorophenyl)-2,2-dimethyl-7-nitro-2H-1,4-benzoxazin-3(4H)-one (206 mg) as a yellow powder (crude product).

(3) The compound obtained in the above step (2) (206 mg) was treated in the same manner as described in Reference Example 1(3) to give 7-amino-5-chloro-4-(4-fluorophenyl)-2,2-dimethyl-2H-1,4-benzoxazin-3(4H)-one (107 mg) as a pale yellow powder.
MS (APCI) m/z: 321/323 [M+H]+

Reference Example 55

A mixture of 7-amino-5-bromo-4-(4-fluorophenyl)-2,2-dimethyl-2H-1,4-benzoxazin-3(4H)-one (compound obtained in Reference Example 53(7); 140 mg), potassium carbonate (159 mg), dioxane (11 mL), trimethylboroxin (134 μL) and [1,1'-bis(diphenylphosphino)ferrocene]dichloropalladium(II) (31 mg) was refluxed under argon atmosphere for 2 hours. After cooling, to the reaction mixture was added water, and the mixture was extracted with ethyl acetate. The organic layer was washed with brine, dried over magnesium sulfate and concentrated in vacuo. The resultant residue was purified by column chromatography on silica gel (solvent; n-hexane/ethyl acetate=3/1→3/7) to give 7-amino-4-(4-fluorophenyl)-2,2,5-trimethyl-2H-1,4-benzoxazin -3(4H)-one (102 mg) as a pale yellow powder.
MS (APCI) m/z: 301 [M+H]+

Reference Example 56

(1) To a suspension of 6-amino-2,4-xylenol (0.69 g) and potassium carbonate (3.46 g) in N,N-dimethylformamide (20 mL) was added ethyl α-bromoisobutylate (1.3 mL), and the mixture was stirred at room temperature for 16 hours. After cooling, the reaction mixture was diluted with ethyl acetate, and the mixture was washed successively with water and brine. The organic layer was dried over magnesium sulfate and concentrated in vacuo. The resultant residue was purified by column chromatography on silica gel (solvent; n-hexane/ethyl acetate=19/1→3/1) and triturated with diisopropylether to give 2,2,6,8-tetramethyl-2H-1,4-benzoxazin-3(4H)-one (0.28 g) as a gray powder.
MS (APCI) m/z: 206 [M+H]+

(2) To a solution of the compound obtained in the above step (1) (337 mg) in acetic anhydride (6 mL) was added 70% nitric acid (115 μL), and the mixture was stirred at room temperature for 1.5 hours. To the reaction mixture was added 70% nitric acid (94 μL), and the mixture was stirred at room temperature for 17 hours. The reaction mixture was gradually poured to a mixture of ice and an aqueous saturated sodium hydrogencarbonate solution, and the mixture was extracted with diethylether. The organic layer was washed successively with an aqueous saturated sodium hydrogencarbonate solution and brine, dried over magnesium sulfate and concentrated in vacuo. The residue was triturated with n-hexane/diisopropylether to give 2,2,6,8-tetramethyl-7-nitro-2H-1,4-benzoxazin-3(4H)-one (138 mg) as a colorless powder.
ESI-MS m/z: 249 [M−H]⁻

(3) The compound obtained in the above step (2) (185 mg) and 4-fluorophenylboronic acid (207 mg) were treated in the same manner as described in Reference Example 1(2) to give 4-(4-fluorophenyl)-2,2,6,8-tetramethyl-7-nitro-2H-1,4-benzoxazin-3(4H)-one (128 mg) as a colorless powder.
MS (APCI) m/z: 362 [M+NH$_4$]$^+$ (4) To a solution of the compound obtained in the above step (3) (125 mg) in methanol (17 mL) was added 10% palladium-carbon (100 mg), and the mixture was stirred at room temperature under atmospheric pressure of hydrogen for 2 hours. The reaction mixture was filtered, and the filtrate was concentrated in vacuo. The resultant residue was purified by column chromatography on silica gel (solvent; n-hexane/ethyl acetate (19/1)→ethyl acetate) and triturated with diisopropylether to give 7-amino-4-(4-fluorophenyl)-2,2,6,8-tetramethyl-2H-1,4-benzoxazin-3(4H)-one (103 mg) as a colorless powder.
MS (APCI) m/z: 315 [M+H]$^+$ Reference Example 57

(1) To a suspension of 2-amino-5-nitrophenol (1.98 g) and potassium fluoride (2.24 g) in N,N-dimethylformamide (40 mL) was added ethyl bromofluoroacetate (2.85 g), and the mixture was stirred at 60° C. for 44 hours. After cooling, the reaction mixture was diluted with ethyl acetate, and the mixture was washed successively with water and brine. The organic layer was dried over magnesium sulfate and concentrated in vacuo. The resultant residue was purified by column chromatography on silica gel (solvent; n-hexane/ethyl acetate=19/1→1/1) and triturated with n-hexane/diisopropylether to give 2-fluoro-7-nitro-2H-1,4-benzoxazin-3(4H)-one (1.14 g) as a yellow powder.
ESI-MS m/z: 211 [M−H]⁻

(2) The compound obtained in the above step (1) (0.86 g) and 4-fluorophenylboronic acid (1.13 g) were treated in the same manner as described in Reference Example 1(2) to give 2-fluoro-4-(4-fluorophenyl)-7-nitro-2H-1,4-benzoxazin-3(4H)-one (0.65 g) as a yellow powder.
MS (APCI) m/z: 339 [M+H+MeOH]$^+$ Reference Example 58

To a solution of 1-hydroxycyclopentanecarboxylic acid (2.00 g) in methanol (15 mL) was added conc. sulfuric acid (0.1 mL), and the mixture was stirred at room temperature for 18 hours. The reaction mixture was concentrated in vacuo, and the resultant residue was diluted with diethylether. The mixture was washed successively with an aqueous saturated sodium hydrogencarbonate solution and brine. The organic layer was dried over sodium sulfate and concentrated in vacuo to give methyl 1-hydroxy-cyclopentanecarboxylate (2.06 g) as a pale brown oil.
MS (APCI) m/z: 162 [M+NH$_4$]$^+$ Reference Example 59

1-Hydroxycyclohexanecarboxylic acid (2.50 g) was treated in the same manner as described in Reference Example 58 to give methyl 1-hydroxycyclohexanecarboxylate (2.55 g) as a pale yellow oil.
MS (APCI) m/z: 176 [M+NH$_4$]$^+$ Reference Example 60

(1) To a solution of 2-ethyl-2-hydroxybutyric acid (5.00 g) in methanol (35 mL) was added conc. sulfuric acid (0.25 mL), and the mixture was refluxed at room temperature for 18 hours and then refluxed under heating for 18 hours. After cooling, the reaction mixture was concentrated in vacuo, and the resultant residue was diluted with diethylether. The mixture was washed successively with an aqueous saturated sodium hydrogencarbonate solution and brine, dried over sodium sulfate and concentrated in vacuo. The residue was distilled to give methyl 2-ethyl-2-hydroxybutyrate (3.70 g) as a colorless oil,
b.p. 60-61° C./20 mmHg (2) To a solution of the compound obtained in the above step (1) (525 mg) and 4-chloro-2-fluoronitrobenzene (600 mg) in tetrahydrofuran (10 mL) was added 60% sodium hydride (oily dispersion, 150 mg) under ice-cooling, and the mixture was stirred at room temperature for 2 hours. To the reaction mixture was added an aqueous saturated ammonium chloride solution, and the mixture was extracted with ethyl acetate. The organic layer was washed with brine, dried over sodium sulfate and concentrated in vacuo. The resultant residue was purified by column chromatography on silica gel (solvent; n-hexane/ethyl acetate=20/1→3/1) to give methyl 2-(5-chloro-2-nitrophenoxy)-2-ethylbutyrate (788 mg) as a colorless oil.
MS (APCI) m/z: 319/321 [M+NH$_4$]$^+$ (3) To a solution of the compound obtained in the above step (2) (0.77 g) in ethyl acetate (10 mL) was added tin(II) chloride dihydrate (2.88 g), and the mixture was stirred at 80° C. for 4 hours. After cooling, to the reaction mixture were added an aqueous saturated sodium hydrogencarbonate solution and ethyl acetate, and the mixture was stirred at room temperature for 1 hour. The mixture was filtered through a celite pad, and the filtrate was extracted with ethyl acetate. The organic layer was washed with brine, dried over sodium sulfate and concentrated in vacuo. The residue was purified by column chromatography on silica gel (solvent; n-hexane/ethyl acetate=10/1→2/1) to give 7-chloro-2,2-diethyl-2H-1,4-benzoxazin-3(4H)-one (490 mg) as a colorless powder.
ESI-MS m/z: 238/240 [M−H]⁻

(4) The compound obtained in the above step (3) (475 mg) and 4-fluorophenylboronic acid (554 mg) were treated in the same manner as described in Reference Example 1(2) to give 7-chloro-2,2-diethyl-4-(4-fluorophenyl)-2H-1,4-benzoxazin-3(4H)-one (514 mg) as a colorless powder.
MS (APCI) m/z: 334/336 [M+H]$^+$ (5) The compound obtained in the above step (4) (150 mg) was treated in the same manner as described in Reference Example 7(3) to give tert-butyl [2,2-diethyl-4-(4-fluorophenyl)-3-oxo-3,4-dihydro-2H-1,4-benzoxazin-7-yl]carbamate (187 mg) as a colorless powder.
MS (APCI) m/z: 415 [M+H]$^+$ (6) The compound obtained in the above step (5) (175 mg) was treated in the same manner as described in Reference Example 7(4) to give 7-amino-2,2-diethyl-4-(4-fluorophenyl)-2H-1,4-benzoxazin-3(4H)-one (126 mg) as a colorless powder.
MS (APCI) m/z: 315 [M+H]$^+$ Reference Example 61

A mixture of 7-amino-2,2-dimethyl-2H-1,4-benzoxazin-3(4H)-one (compound obtained in Reference Example 3(1);

150 mg), 5-bromo-2-chlorotoluene (321 mg), copper(I) iodide (37 mg), potassium carbonate (216 mg), N,N'-dimethylethylenediamine (40 µL) and toluene (8 mL) was heated at 110° C. overnight under argon atmosphere. After cooling, to the reaction mixture was added water, and the mixture was extracted with ethyl acetate. The organic layer was washed with brine, dried over magnesium sulfate and concentrated in vacuo. The residue was purified by column chromatography on silica gel (solvent; n-hexane/ethyl acetate=4/1→1/1) to give 7-amino-4-(4-chloro-3-methylphenyl)-2,2-dimethyl-2H-1,4-benzoxazin-3(4H)-one (98 mg) as a pale orange powder.
MS (APCI) m/z: 317/319 [M+H]$^+$ Reference Example 62

(1) To a solution of 2-bromo-5-nitrophenol (1.83 g) and cesium carbonate (5.48 g) in N,N-dimethylformamide (31 mL) was added ethyl α-bromoisobutylate (2.46 g), and the mixture was stirred at room temperature for 3 days. The reaction mixture was diluted with ethyl acetate, and the mixture was washed successively with water and brine, dried over magnesium sulfate and concentrated in vacuo. The resultant residue was purified by column chromatography on silica gel (solvent; n-hexane/ethyl acetate=19/1→87/13) to give ethyl 2-(2-bromo-5-nitrophenoxy)-2-methylpropionate (1.93 g) as a colorless viscous oil.
MS (APCI) m/z: 349/351 [M+NH$_4$]$^+$ (2) To a solution of the compound obtained in the above step (1) (150 mg) and 2-chloro-4-fluoroaniline (263 mg) in dichloromethane (10 mL) was added dropwise 2M trimethylaluminum solution in toluene (903 µL) under argon atmosphere, and the mixture was stirred at room temperature for 1.5 hours. To the reaction mixture was added 1N hydrochloric acid (20 mL) under ice-cooling, and the mixture was extracted with chloroform. The organic layer was dried over magnesium sulfate and concentrated in vacuo. The residue was purified by column chromatography on silica gel (solvent; n-hexane/ethyl acetate=24/1→17/3) to give 2-(2-bromo-5-nitrophenoxy)-N-(2-chloro-4-fluorophenyl)-2-methylpropionamide (194 mg) as a pale yellow viscous oil.
MS (APCI) m/z: 448/450 [M+NH$_4$]$^+$ (3) A mixture of the compound obtained in the above step (2) (190 mg), copper(I) iodide (168 mg), potassium carbonate (73 mg) and pyridine (8 mL) was heated at 100° C. overnight under argon atmosphere. After cooling, the reaction mixture was diluted with ethyl acetate, and the mixture was washed successively with an aqueous citric acid solution, water and brine, dried over magnesium sulfate and concentrated in vacuo. The residue was purified by column chromatography on NH-silica gel (Chromatorex NH-silica gel; solvent; n-hexane/ethyl acetate=24/1→41/9) and triturated with n-hexane/diethylether to give 4-(2-chloro-4-fluorophenyl)-2,2-dimethyl-7-nitro-2H-1,4-benzoxazin-3(4M)-one (73 mg) as an orange solid.
MS (APCI) m/z: 351/353 [M+H]$^+$ (4) The compound obtained in the above step (3) (63 mg) was treated in the same manner as described in Reference Example 1(3) to give 7-amino-4-(2-chloro-4-fluorophenyl)-2,2-dimethyl-2H-1,4-benzoxazin-3(4H)-one (54 mg) as an orange powder.
MS (APCI) m/z: 321/323 [M+H]$^+$ Reference Example 63

(1) To a solution of ethyl 2-(2-bromo-5-nitrophenoxy)-2-methylpropionate (compound obtained in Reference Example 62(1); 332 mg) in tetrahydrofuran (1 mL)-ethanol (2 mL) was added an aqueous 5N sodium hydroxide solution (2 mL), and the mixture was stirred at room temperature for 2 hours. The reaction mixture was acidified with 6N HCl (3 mL) and the mixture was extracted with diethylether. The organic layer was washed with brine, dried over magnesium sulfate and concentrated in vacuo to give 2-(2-bromo-5-nitrophenoxy)-2-methylpropionic acid (297 mg) as colorless crystals.
ESI-MS m/z: 302/304 [M–H]$^-$ (2) To a solution of the compound obtained in the above step (1) (295 mg) in dichloromethane (10 mL) were added oxalyl chloride (253 µL) and a drop of N,N-dimethylformamide, and the mixture was stirred at room temperature overnight. The reaction mixture was concentrated in vacuo to give crude 2-(2-bromo-5-nitrophenoxy)-2-methylpropionyl chloride. To a solution of 4-fluoro-2,6-dimethyl-aniline (149 mg) in tetrahydrofuran (15 mL) was added dropwise 1.6N n-butyl lithium/hexane solution (680 µL) over a period of one minute under cooling in dry ice-acetone bath under argon atmosphere. The mixture was stirred at the same temperature for 5 minutes. Thereto was added quickly a solution of 2-(2-bromo-5-nitrophenoxy)-2-methylpropionyl chloride in tetrahydrofuran (10 mL), and the mixture was stirred at the same temperature for 30 minutes. To the reaction mixture was added an aqueous citric acid solution, and the mixture was basified with an aqueous saturated sodium hydrogencarbonate solution and extracted with ethyl acetate. The organic layer was washed successively with water and brine, dried over magnesium sulfate and concentrated in vacuo. The resultant residue was purified by column chromatography on NH-silica gel (Chromatorex NH-silica gel; solvent; n-hexane/ethyl acetate=19/1→3/1) to give 2-(2-bromo-5-nitrophenoxy)-N-(4-fluoro-2,6-dimethylphenyl)-2-methylpropionamide (262 mg) as a colorless solid.
MS (APCI) m/z: 425/427 [M+H]$^+$ (3) The compound obtained in the above step (2) (260 mg) was treated in the same manner as described in Reference Example 62(3) to give 4-(4-fluoro-2,6-dimethyl-phenyl)-2,2-dimethyl-7-nitro-2H-1,4-benzoxazin-3(4H)-one (76 mg) as a pale yellow powder.
MS (APCI) m/z: 345 [M+H]$^+$ (4) The compound obtained in the above step (3) (69 mg) was treated in the same manner as described in Reference Example 1(3) to give 7-amino-4-(4-fluoro-2,6-dimethylphenyl)-2,2-dimethyl-2H-1,4-benzoxazin-3(4H)-one (62 mg) as an orange powder.
MS (APCI) m/z: 315 [M+H]$^+$ Reference Example 64

(1) To a solution of the compound obtained in Reference Example 63(1) (295 mg) in dichloromethane (10 mL) were added oxalyl chloride (253 µL) and a drop of N,N-dimethylformamide, and the mixture was stirred at room temperature overnight. The reaction mixture was concentrated in vacuo to give crude 2-(2-bromo-5-nitrophenoxy)-2-methylpropionyl chloride. To a solution of 2-amino-5-bromo-3-methylpyridine (727 mg) in tetrahydrofuran (20 mL) was added dropwise 1M lithium bis(trimethylsilyl)amide-tetrahydrofuran solution (3.88 mL) over a period of one minute under cooling in dry ice-acetone bath under argon atmosphere. The mixture was stirred at the same temperature for 5 minutes. Thereto was added quickly a solution of 2-(2-bromo-5-nitrophenoxy)-2-methylpropionyl chloride in tetrahydrofuran (10 mL), and the mixture was stirred at the same temperature for 30 minutes. To the reaction mixture was added an aqueous citric acid solution, and the mixture was basified with an aqueous saturated sodium hydrogencarbonate solution and extracted with ethyl acetate. The organic layer was washed successively with water and brine, dried over magnesium sulfate and concentrated in vacuo. The residue was purified by column chromatography on NH-silica gel (Chromatorex NH-silica gel; solvent; n-hexane/ethyl acetate=19/1→3/1) to give N-(5-bromo-3-methylpyridin-2-yl)-2-(2-bromo-5-nitrophenoxy)-2-methylpropionamide (599 mg) as a colorless powder.

MS (APCI) m/z: 472/474 [M+H]$^+$ (2) The compound obtained in the above step (1) (598 mg) and copper(I) bromide (733 mg) were treated in the same manner as described in Reference Example 62(3) to give 4-(5-bromo-3-methylpyridin-2-yl)-2,2-dimethyl-7-nitro-2H-1,4-benzoxazin-3(4H)-one (154 mg) as a pale orange powder.

MS (APCI) m/z: 392/394 [M+H]$^+$ (3) The compound obtained in the above step (2) (148 mg) was treated in the same manner as described in Reference Example 1(3) to give 7-amino-4-(5-bromo-3-methylpyridin-2-yl)-2,2-dimethyl-2H-1,4-benzoxazin-3(4H)-one (136 mg) as a colorless powder.

MS (APCI) m/z: 362/364 [M+H]$^+$

Reference Example 65

(1) The corresponding starting materials were treated in the same manner as described in Reference Example 62(1) to (3) to give 2,2-dimethyl-4-[4-methyl-3-(trifluoromethyl)phenyl]-7-nitro-2H-1,4-benzoxazin-3(4H)-one as a pale yellow powder.

MS (APCI) m/z: 381 [M+H]$^+$ (2) The compound obtained in the above step (1) (75 mg) was treated in the same manner as described in Reference Example 1(3) to give 7-amino-2,2-dimethyl-4-[4-methyl-3-(trifluoromethyl)phenyl]-2H-1,4-benzoxazin-3(4H)-one (65 mg) as an orange solid.

MS (APCI) m/z: 351 [M+H]$^+$

Reference Example 66

(1) The corresponding starting materials were treated in the same manner as described in Reference Example 62(1) to (3) to give 4-(2,2-difluoro-1,3-benzodioxol-5-yl)-2,2-dimethyl-7-nitro-2H-1,4-benzoxazin-3(4H)-one as a pale orange powder.

(2) The compound obtained in the above step (1) (40 mg) was treated in the same manner as described in Reference Example 1(3) to give 7-amino-4-(2,2-difluoro-1,3-benzodioxol-5-yl)-2,2-dimethyl-2H-1,4-benzoxazin-3(4H)-one (13 mg) as a colorless powder.

MS (APCI) m/z: 349 [M+H]$^+$

Reference Examples 68 to 71

The corresponding starting materials were treated in the same manner as described in Reference Example 3 to give compounds shown in the following Table 35.

TABLE 35

| Ref. Ex. Nos. | Ar | Physicochemical properties etc. |
|---|---|---|
| 68 | H$_3$C–C$_6$H$_4$– | MS(APCI)m/z: 283[M + H]$^+$ |
| 69 | F$_3$C–C$_6$H$_4$– | MS(APCI)m/z: 337[M + H]$^+$ |
| 70 | C$_2$H$_5$–C$_6$H$_4$– | MS(APCI)m/z: 297[M + H]$^+$ |
| 71 | H$_3$CS–C$_6$H$_4$– | MS(APCI)m/z: 315[M + H]$^+$ |

Reference Examples 72 to 74

The corresponding starting materials were treated in the same manner as described in Reference Example 2 to give compounds shown in the following Table 36.

TABLE 36

| Ref. Ex. Nos. | Ar | Physicochemical properties etc. |
|---|---|---|
| 72 | 3-CH$_3$, C$_2$H$_5$-phenyl | MS(APCI)m/z: 297[M + H]$^+$ |
| 73 | 2-CH$_3$, C$_2$H$_5$-phenyl | MS(APCI)m/z: 297[M + H]$^+$ |
| 74 | 5-Br-pyrimidin-2-yl | MS(APCI)m/z: 349/351[M + H]$^+$ |

Reference Examples 75 to 109

The corresponding starting materials were treated in the same manner as described in Reference Example 61 to give compounds shown in the following Tables 37 to 41.

TABLE 37

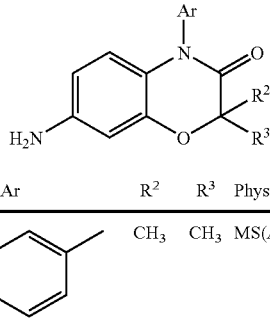

| Ref. Ex. Nos. | Ar | R² | R³ | Physicochemical properties etc. |
|---|---|---|---|---|
| 75 | H₃CO-C₆H₄- (3-methoxyphenyl) | CH₃ | CH₃ | MS(APCI)m/z: 299[M + H]⁺ |
| 76 | 3-methoxy-4-chlorophenyl | CH₃ | CH₃ | MS(APCI)m/z: 333/335[M + H]⁺ |
| 77 | 2,3-dihydrobenzo[1,4]dioxin-6-yl | CH₃ | CH₃ | MS(APCI)m/z: 327[M + H]⁺ |
| 78 | 5-chlorothien-2-yl | H | H | MS(APCI)m/z: 281/283[M + H]⁺ |
| 79 | 2-(difluoromethyl)-4-fluorophenyl | CH₃ | CH₃ | MS(APCI)m/z: 337[M + H]⁺ |
| 80 | 4-cyclopropylphenyl | CH₃ | CH₃ | MS(APCI)m/z: 309[M + H]⁺ |
| 81 | 3,4-difluoro-5-methoxyphenyl | CH₃ | CH₃ | MS(APCI)m/z: 335[M + H]⁺ |
| 82 | 3-(methoxysulfonyl)phenyl | CH₃ | CH₃ | MS(APCI)m/z: 347[M + H]⁺ |

TABLE 38

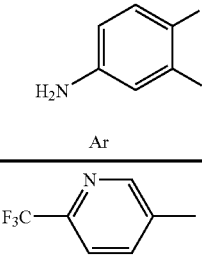

| Ref. Ex. Nos. | Ar | Physicochemical properties etc. |
|---|---|---|
| 83 | 6-(trifluoromethyl)pyridin-3-yl | MS(APCI)m/z: 338[M + H]⁺ |

TABLE 38-continued

| Ref. Ex. Nos. | Ar | Physicochemical properties etc. |
|---|---|---|
| 84 | 2-naphthyl | MS(APCI)m/z: 319[M + H]+ |
| 85 | 3-(t-BuO-C(O)-CH2-O)-phenyl | MS(APCI)m/z: 399[M + H]+ |
| 86 | 4-bromo-3-methylphenyl (H3C, Br substituents) | MS(APCI)m/z: 361/363[M + H]+ |
| 87 | 3-(trifluoromethoxy)phenyl | MS(APCI)m/z: 353[M + H]+ |
| 88 | 4-chloro-3-methoxyphenyl | MS(APCI)m/z: 333/335[M + H]+ |
| 89 | 3-fluoro-4-(trifluoromethyl)phenyl | MS(APCI)m/z: 355[M + H]+ |
| 90 | 4-chloro-3-(trifluoromethyl)phenyl | MS(APCI)m/z: 371/373[M + H]+ | t-Bu: tert-butyl group

TABLE 39

| Ref. Ex. Nos. | Ar | Physicochemical properties etc. |
|---|---|---|
| 91 | 5-chloropyridin-2-yl | MS(APCI)m/z: 304/306[M + H]+ |
| 92 | 4-chloro-3-fluorophenyl | MS(APCI)m/z: 321/323[M + H]+ |

TABLE 39-continued

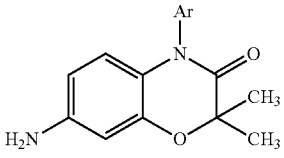

| Ref. Ex. Nos. | Ar | Physicochemical properties etc. |
|---|---|---|
| 93 | (3-methyl-4-fluorophenyl) | MS(APCI)m/z: 301[M + H]$^+$ |
| 94 | (3-trifluoromethyl-5-methylphenyl) | MS(APCI)m/z: 337[M + H]$^+$ |
| 95 | (4-methylphenyl-CH$_2$OZ) | MS(APCI)m/z: 403[M + H]$^+$ |
| 96 | (3-nitro-5-methylphenyl) | MS(APCI)m/z: 314[M + H]$^+$ |
| 97 | (3-chloro-5-methylphenyl) | MS(APCI)m/z: 303/305[M + H]$^+$ |

Z = benzoyl group

TABLE 40

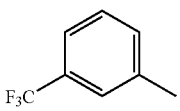

| Ref. Ex. Nos. | Ar | Physicochemical properties etc. |
|---|---|---|
| 98 | (2-chloro-5-methylphenyl-CH$_2$OZ) | MS(APCI)m/z: 437/439[M + H]$^+$ |
| 99 | (5-chloro-3-methyl-2-methylpyridyl) | MS(APCI)m/z: 318/320[M + H]$^+$ |
| 100 | (3-methyl-2-methylpyridyl) | MS(APCI)m/z: 284[M + H]$^+$ |
| 101 | (5-nitro-3-methyl-2-methylpyridyl) | MS(APCI)m/z: 329[M + H]$^+$ |
| 102 | (5-trifluoromethyl-3-chloro-2-methylpyridyl) | MS(APCI)m/z: 372/374[M + H]$^+$ |
| 103 | (5-bromo-2-methylpyridyl) | MS(APCI)m/z: 348/350[M + H]$^+$ |
| 104 | (5-methyl-2-trifluoromethylthienyl) | MS(APCI)m/z: 343[M + H]$^+$ |

Z = benzoyl group

TABLE 41

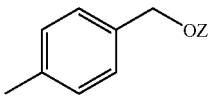

| Ref. Ex. Nos. | R' | Ar | Physicochemical properties etc. |
|---|---|---|---|
| 105 | H | (5-bromo-4-methyl-2-methylpyridyl) | MS(APCI)m/z: 362/364[M + H]$^+$ |
| 106 | H | (6-methyl-2-trifluoromethylpyridyl) | MS(APCI)m/z: 338[M + H]$^+$ |
| 107 | F | (4-chlorophenyl-methyl) | MS(APCI)m/z: 321/323[M + H]$^+$ |
| 108 | F | (5-chloro-2-methylpyridyl) | MS(APCI)m/z: 322/324[M + H]$^+$ |

TABLE 41-continued

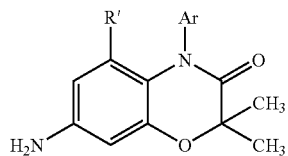

| Ref. Ex. Nos. | R' | Ar | Physicochemical properties etc. |
|---|---|---|---|
| 109 | F | (5-fluoro-2-pyridyl with methyl) | MS(APCI)m/z: 306[M + H]$^+$ |

Reference Examples 110 to 126

The corresponding starting materials were treated in the same manner as described in Reference Example 62 to give compounds shown in the following Tables 42 to 44.

TABLE 42

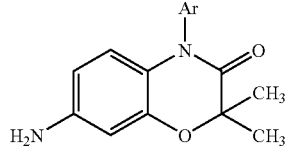

| Ref. Ex. Nos. | Ar | Physicochemical properties etc. |
|---|---|---|
| 110 | 2,4-difluorophenyl | MS(APCI)m/z: 305[M + H]$^+$ |
| 111 | 5-fluoro-2-methoxyphenyl with methyl | MS(APCI)m/z: 317[M + H]$^+$ |
| 112 | 4-chloro-2-fluorophenyl | MS(APCI)m/z: 321/323[M + H]$^+$ |
| 113 | 4-chloro-2-methylphenyl | MS(APCI)m/z: 317/319[M + H]$^+$ |
| 114 | 5-chloro-2-cyanophenyl | MS(APCI)m/z: 328/330[M + H]$^+$ |
| 115 | 4-fluoro-2,3-dimethylphenyl | MS(APCI)m/z: 315[M + H]$^+$ |

TABLE 42-continued

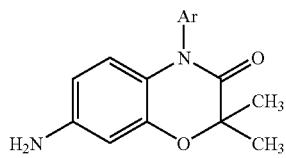

| Ref. Ex. Nos. | Ar | Physicochemical properties etc. |
|---|---|---|
| 116 | 3-chloro-2-methylphenyl | MS(APCI)m/z: 317/319[M + H]$^+$ |

TABLE 43

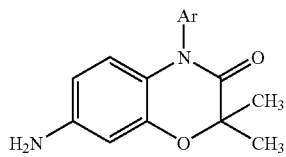

| Ref. Ex. Nos. | Ar | Physicochemical properties etc. |
|---|---|---|
| 117 | 4-trifluoromethyl-2-methylphenyl | MS(APCI)m/z: 351[M + H]$^+$ |
| 118 | 2-methoxy-4-fluorophenyl | MS(APCI)m/z: 317[M + H]$^+$ |
| 119 | 4-fluoro-2-methylphenyl | MS(APCI)m/z: 301[M + H]$^+$ |
| 120 | 4-cyano-2-methylphenyl | MS(APCI)m/z: 308[M + H]$^+$ |
| 121 | 4-bromo-2-methylphenyl | MS(APCI)m/z: 361/363[M + H]$^+$ |
| 122 | 2-trifluoromethyl-3-methylphenyl | MS(APCI)m/z: 351[M + H]$^+$ |
| 123 | 4-fluoro-2-methylphenyl | MS(APCI)m/z: 301[M + H]$^+$ |

TABLE 43-continued

Structure: Ar-N of benzoxazinone with H₂N- substituent, 2,2-dimethyl

| Ref. Ex. Nos. | Ar | Physicochemical properties etc. |
|---|---|---|
| 124 | 4-pyridyl | Note 2 |

Note 2:
The compound was used as a starting material in the following step without further purification.

TABLE 44

Structure: R''-substituted benzoxazinone with Ar on N, H₂N-, 2,2-dimethyl

| Ref. Ex. Nos. | R'' | Ar | Physicochemical properties etc. |
|---|---|---|---|
| 125 | F | 4-F-phenyl | MS(APCI)m/z: 305[M + H]⁺ |
| 126 | H | 2-Cl-4-methyl-5-methoxy-phenyl (with H₃C) | MS(APCI)m/z: 347/349 [M + H]⁺ |

Reference Examples 127 to 128

The corresponding starting materials were treated in the same manner as described in Reference Example 53 to give compounds shown in the following Table 45.

TABLE 45

Structure: 5-Cl-benzoxazinone with Ar on N, 7-H₂N-, 2,2-dimethyl

| Ref. Ex. Nos. | Ar | Physicochemical properties etc. |
|---|---|---|
| 127 | 4-F-phenyl | MS(APCI)m/z: 321/323[M + H]⁺ |
| 128 | 4-Cl-phenyl | MS(APCI)m/z: 337/339[M + H]⁺ |

Reference Examples 129 to 131

The corresponding starting materials were treated in the same manner as described in Reference Example 60(1) to (6) or Reference Example 60(2) to (6) to give compounds shown in the following Table 46.

TABLE 46

Structure: benzoxazinone with Ar on N, H₂N-, R²/R³ at 2-position

| Ref. Ex. Nos. | Ar | $\begin{array}{c}R^2\\R^3\end{array}$ | Physicochemical properties etc. |
|---|---|---|---|
| 129 | 4-F-phenyl | spirocyclopropyl | MS(APCI)m/z: 285[M + H]⁺ |
| 130 | 4-F-phenyl | spirocyclopentyl | MS(APCI)m/z: 313[M + H]⁺ |

TABLE 46-continued

Structure: Ar-N, benzoxazinone core with H₂N- substituent, R², R³ groups

| Ref. Ex. Nos. | Ar | R²/R³ | Physicochemical properties etc. |
|---|---|---|---|
| 131 | 4-F-phenyl | 1-methylcyclohexyl | MS(APCI)m/z: 327[M + H]⁺ |

Reference Examples 132 to 136

The corresponding starting materials were treated in the same manner as described in Reference Example 63 to give compounds as shown in the following Table 47.

TABLE 47

Structure: Ar-N benzoxazinone with H₂N-, CH₃, CH₃ substituents

| Ref. Ex. Nos. | Ar | Physicochemical properties etc. |
|---|---|---|
| 132 | 3,4,5-trimethylphenyl | MS(APCI)m/z: 311[M + H]⁺ |
| 133 | 4-Cl-3,5-dimethylphenyl | MS(APCI)m/z: 331[M + H]⁺ |
| 134 | 2,3-dimethylphenyl | MS(APCI)m/z: 297[M + H]⁺ |
| 135 | 4-F-2-CF₃-phenyl | MS(APCI)m/z: 355[M + H]⁺ |
| 136 | 4-CF₃-2-CH₃-phenyl | MS(APCI)m/z: 351[M + H]⁺ |

Reference Examples 137 to 141

The corresponding starting materials were treated in the same manner as described in Reference Example 64 to give compounds as shown in the following Table 48.

TABLE 48

Structure: Ar-N benzoxazinone with H₂N-, CH₃, CH₃ substituents

| Ref. Ex. Nos. | Ar | Physicochemical properties etc. |
|---|---|---|
| 137 | 3,5-dichloro-2-methylpyridin-yl | MS(APCI)m/z: 338/340[M + H]⁺ |
| 138 | 2,4,6-trifluoro-3-methylphenyl | MS(APCI)m/z: 323[M + H]⁺ |
| 139 | 2-Cl-4-CH₃-5-methylpyridinyl | MS(APCI)m/z: 318/320[M + H]⁺ |
| 140 | 3-Br-2-CH₃-6-methylpyridinyl | MS(APCI)m/z: 362/364[M + H]⁺ |
| 141 | 5-methylquinolinyl | MS(APCI)m/z: 320[M + H]⁺ |

Reference Example 142

(1) To a solution of 5-bromo-2-chlorobenzylalcohol (1.0 g) and pyridine (0.44 mL) in chloroform (40 mL) was added benzoyl chloride (0.58 mL) under ice-cooling, and the mixture was stirred at room temperature overnight. To the reaction mixture was added 1N HCl under ice-cooling, and the mixture was extracted with chloroform. The organic layer was washed successively with water, an aqueous saturated sodium hydrogencarbonate solution and brine, dried over magnesium sulfate and concentrated in vacuo. The resultant residue was triturated with diisopropylether to give 5-bromo-2-chlorobenzyl benzoate (753 mg) as a colorless powder.
MS (APCI) m/z: 325/327 [M+H]$^+$ (2) The compound obtained in Reference Example 3(1) (150 mg) and the compound obtained in the above step (1) (508 mg) were treated in the same manner as described in Reference Example 61 to give 5-(7-amino-2,2-dimethyl-3-oxo-2,3-dihydro-4H-1,4-benzoxazin-4-yl)-2-benzyl benzoate (163 mg) as a green powder.
MS (APCI) m/z: 437/439 [M+H]$^+$

Reference Example 143

(1) 4-Bromobenzylalcohol (2.00 g) was treated in the same manner as described in Reference Example 142(1) to (3) to give 4-bromobenzyl benzoate (2.96 g) as a colorless oil.
MS (APCI) m/z: 308/310 [M+NH$_4$]$^+$ (2) The compound obtained in the above step (1) (454 mg) and the compound obtained in Reference Example 3(1) were treated in the same manner as described in Reference Example 61 to give 4-(7-amino-2,2-dimethyl-3-oxo-2,3-dihydro-4H-1,4-benzoxazin-4-yl)benzyl benzoate (220 mg) as an orange powder.
MS (APCI) m/z: 403 [M+H]$^+$

Reference Example 143B (1) A mixture of 7-amino-5-bromo-4-(4-fluorophenyl)-2,2-dimethyl-2H-1,4-benzoxazin-3(4H)-one (compound obtained in Reference Example 53(7); 100 mg), tributyl(1-ethoxyvinyl)tin (278 μL), dichlorobis(triphenylphosphine)palladium(II) (19 mg) and toluene was heated at 100° C. under argon atmosphere for 4 hours. After cooling, the reaction mixture was filtered through a NH-silica gel pad, and the filtrate was concentrated in vacuo to give 7-amino-5-(1-ethoxyvinyl)-4-(4-fluorophenyl)-2,2-dimethyl-2H-1,4-benzoxazin-3(4H)-one as a crude product.

(2) To a solution of the compound obtained in the above step (1) in dioxane (8 mL) was added 6N HCl (1 mL), and the mixture was stirred at room temperature for 1.5 hours. To the reaction mixture was added an aqueous saturated sodium hydrogencarbonate solution, and the mixture was extracted with ethyl acetate. The organic layer was washed with brine, dried over magnesium sulfate and concentrated in vacuo. The residue was purified by column chromatography on silica gel (solvent; n-hexane/ethyl acetate=2/1→1/1) to give 5-acetyl-7-amino-4-(4-fluorophenyl)-2,2-dimethyl-2H-1,4-benzoxazin-3(4H)-one (64 mg) as a yellow oil
MS (APCI) m/z: 329 [M+H]$^+$

Reference Example 144

(1) A mixture of 5-bromo-4-(4-fluorophenyl)-2,2-dimethyl-7-nitro-2H-1,4-benzoxazin-3(4H)-one (compound obtained in Reference Example 53(6); 100 mg), tributyl(vinyl)tin (78 μL) and tetrakis(triphenylphosphine)palladium(0) (59 mg) and dioxane was refluxed under argon atmosphere for 6 hours. After cooling, the reaction mixture was concentrated in vacuo, and the resultant residue was diluted with acetonitrile and n-hexane. The n-hexane layer was removed from the mixture, and the acetonitrile layer was concentrated in vacuo. The resultant residue was purified by column chromatography on silica gel (solvent; n-hexane/ethyl acetate=8/1→4/1) and filtered through NH-silica gel. The filtrate was concentrated in vacuo to give 4-(4-fluorophenyl)-2,2-dimethyl-7-nitro-5-vinyl-2H-1,4-benzoxazin-3(4H)-one (40 mg) as a pale yellow oil.

(2) The compound obtained in the above step (1) (40 mg) was treated in the same manner as described in Reference Example 1(3) to give 7-amino-4-(4-fluorophenyl)-2,2-dimethyl-5-vinyl-2H-1,4-benzoxazin-3(4H)-one (23 mg) as a pale yellow oil.
MS (APCI) m/z: 313 [M+H]$^+$

Reference Example 145

(1) To a solution of 2-(2-bromo-5-nitrophenoxy)-2-methylpropionic acid (compound obtained in Reference Example 63(1); 304 mg) in dichloromethane (5 mL) were added oxalyl chloride (174 μL) and a drop of N,N-dimethylformamide, and the mixture was stirred at room temperature for 2 hours. The reaction mixture was concentrated in vacuo, and the residual (2-(2-bromo-5-nitrophenoxy)-2-methylpropionyl chloride) was dissolved in chloroform (5 mL). To the solution were added 5-amino-6-chloro-2,2-difluoro-1,3-benzodioxole (228 mg) and pyridine (0.12 mL), and the mixture was stirred at room temperature overnight. The reaction mixture was diluted with chloroform, and the mixture was washed with 2N HCl, dried over magnesium sulfate and concentrated in vacuo. The residue was purified by column chromatography on NH-silica gel (Chromatorex NH-silica gel; solvent; n-hexane/ethyl acetate=97/3→85/15) to give 2-(2-bromo-5-nitrophenoxy)-N-(6-chloro-2,2-difluoro-1,3-benzodioxol-5-yl)-2-methylpropionamide (401 mg) as colorless crystals.
MS (APCI) m/z: 493/495 [M+H]$^+$ (2) The compound obtained in the above step (1) (400 mg) was treated in the same manner as described in Reference Example 62(3) to give 4-(6-chloro-2,2-difluoro-1,3-benzodioxol-5-yl)-2,2-dimethyl-7-nitro-2H-1,4-benzoxazin-3(4H)-one (245 mg) as colorless crystals.
MS (APCI) m/z: 413/415 [M+H]$^+$ (3) A mixture of the compound obtained in the above step (2) (140 mg), methanol (2 mL), tetrahydrofuran (4 mL), ethyl acetate (4 mL) and Raney-nickel was stirred at room temperature under atmospheric pressure of hydrogen for 4 hours. The reaction mixture was filtered, and the filtrate was washed with brine, dried over magnesium sulfate and concentrated in vacuo to give 7-amino-4-(6-chloro-2,2-difluoro-1,3-benzodioxol-5-yl)-2,2-dimethyl-2H-1,4-benzoxazin-3(4H)-one (122 mg) as a colorless powder.
MS (APCI) m/z: 383/385 [M+H]$^+$

Reference Example 146

(1) A mixture of 5-bromo-4-(4-fluorophenyl)-2,2-dimethyl-7-nitro-2H-1,4-benzoxazin-3(4H)-one (compound obtained in Reference Example 53(6), 2.00 g), zinc cyanide (0.60 g), tetrakis(triphenylphosphine)palladium(0) (0.60 g) and N,N-dimethylformamide (30 mL) was heated at 175° C. under microwave irradiation for 5 minutes under argon atmosphere. After cooling, to the reaction mixture was added water, and the mixture was extracted with ethyl acetate. The organic layer was washed with water and brine, dried over sodium sulfate and concentrated in vacuo. The resultant residue was purified by column chromatography on silica gel (Solvent; n-hexane/ethyl acetate=95/5→65/35) to give 4-(4-fluorophenyl)-2,2-dimethyl-7-nitro-3-oxo-3,4-dihydro-2H-1,4-benzoxazin-5-carbonitrile (1.42 g) as a pale yellow powder.
MS (APCI) m/z: 342 [M+H]+

(2) The compound obtained in the above step (1) (70 mg) was treated in the same manner as described in Reference Example 1(3) to give 7-amino-4-(4-fluorophenyl)-2,2-dimethyl-3-oxo-3,4-dihydro-2H-1,4-benzoxazin-5-carbonitrile (41 mg) as a pale yellow powder.
MS (APCI) m/z; 342 [M+H]+

Reference Example 147

The corresponding starting materials were treated in the same manner as described in Reference example 64 to give 7-amino-4-(6-chloro-2-methylpyridin-3-yl) -2,2-dimethyl-2H-1,4-benzoxazin-3(4H)-one as a pale yellow powder.
MS (APCI) m/z; 318/320 [M+H]+

Reference Examples 148 to 173

The corresponding starting materials were treated in the same manner as described in Reference Example 61 to give compounds shown in the following Tables 49 to 51.

TABLE 49

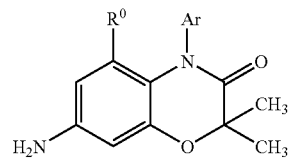

| Ref. Ex. Nos. | R⁰ | Ar | Physicochemical properties etc. |
|---|---|---|---|
| 148 | H | (2-Br, 5-CH₃ pyridyl w/ 3-H₃C) | MS(APCI)m/z: 362/364[M + H]+ |
| 149 | H | (5-F₃C pyridyl) | MS(APCI)m/z: 338[M + H]+ |

TABLE 49-continued

| Ref. Ex. Nos. | R⁰ | Ar | Physicochemical properties etc. |
|---|---|---|---|
| 150 | H | (6-F₃C, 2-CH₃, 3-CH₃ pyridyl) | MS(APCI)m/z: 352[M + H]+ |
| 151 | H | (5-Cl, 3-F, 2-CH₃ pyridyl) | MS(APCI)m/z: 322/324[M + H]+ |
| 152 | F | (5-Br, 2-CH₃ pyridyl) | MS(APCI)m/z: 366/368[M + H]+ |
| 153 | F | (5-F₃C, 2-CH₃ pyridyl) | MS(APCI)m/z: 356[M + H]+ |
| 154 | H | (5-F, 2-CH₃, 3-CH₃ pyridyl) | MS(APCI)m/z: 302[M + H]+ |
| 155 | F | (3-Cl phenyl) | MS(APCI)m/z: 321/323[M + H]+ |
| 156 | F | (5-Cl, 2-CH₃, 3-CH₃ pyridyl) | MS(APCI)m/z: 336/338[M + H]+ |
| 157 | F | (5-Cl, 3-F, 2-CH₃ pyridyl) | MS(APCI)m/z: 340/342[M + H]+ |

TABLE 50

| Ref. Ex. Nos. | R⁰ | Ar | Physicochemical properties etc. |
|---|---|---|---|
| 158 | H | (6-Br, 3-CH₃ pyridazinyl) | MS(APCI)m/z: 349/351[M + H]+ |

TABLE 50-continued
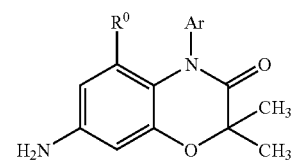
| Ref. Ex. Nos. | R⁰ | Ar | Physicochemical properties etc. |
|---|---|---|---|
| 159 | H | 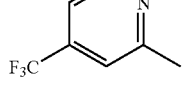 | MS(APCI)m/z: 338[M + H]⁺ |
| 160 | H | 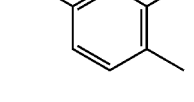 | MS(APCI)m/z: 298[M + H]⁺ |
| 161 | F | 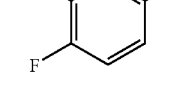 | MS(APCI)m/z: 320[M + H]⁺ |
| 162 | H | 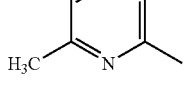 | MS(APCI)m/z: 302[M + H]⁺ |
| 163 | F | 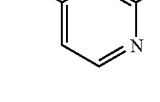 | MS(ESI)m/z: 320/322[M + H]⁺ |
| 164 | F | 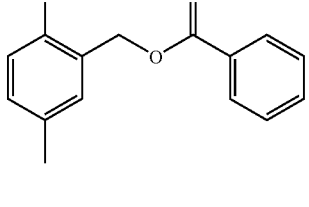 | MS(APCI)m/z: 455/457[M + H]⁺ |
| 165 | F | 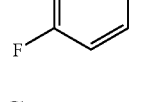 | MS(APCI)m/z: 323[M + H]⁺ |
| 166 | F | 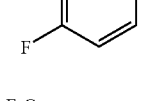 | MS(APCI)m/z: 339/341[M + H]⁺ |
| 167 | F | 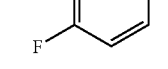 | MS(APCI)m/z: 373[M + H]⁺ |

TABLE 51

Structure: benzoxazin-3(4H)-one with R⁰ at 5-position, Ar at N-4, 2,2-dimethyl, H₂N at 7-position.

| Ref. Ex. Nos. | R⁰ | Ar | Physicochemical properties etc. |
|---|---|---|---|
| 168 | F | 4-(CF₃)phenyl | MS(APCI)m/z: 355[M + H]⁺ |
| 169 | F | 3-F-4-(CF₃)phenyl | MS(APCI)m/z: 373[M + H]⁺ |
| 170 | H | benzothiophen-2-yl | MS(APCI)m/z: 325[M + H]⁺ |
| 171 | H | benzofuran-2-yl | MS(APCI)m/z: 309[M + H]⁺ |
| 172 | F | 5-(CF₃)thiophen-2-yl | MS(APCI)m/z: 302[M + H]⁺ |
| 173 | F | 5-F-3-methyl-2-methylpyridinyl | MS(APCI)m/z: 320[M + H]⁺ |

Reference Example 174

(1) A mixture of 5-bromo-4-(4-fluorophenyl)-2,2-dimethyl-7-nitro-2H-1,4-benzoxazin-3(4H)-one (compound obtained in Reference Example 53(6), 200 mg), cyclopropylboronic acid (65 mg), potassium phosphate (410 mg), tetrakis-(triphenylphosphine)palladium(0) (66 mg), water (0.1 mL) and toluene (5 mL) was heated at 100° C. under argon atmosphere for 4 hours. After cooling, to the reaction mixture was added water, and the mixture was extracted with ethyl acetate. The organic layer was washed with water and brine, dried over sodium sulfate and concentrated in vacuo. The resultant residue was purified by column chromatography on silica gel (Solvent; n-hexane/ethyl acetate=95/5→65/35) to give 5-cyclopropyl-4-(4-fluorophenyl) -2,2-dimethyl-7-nitro-2H-1,4-benzoxazin-3(4H)-one (146 mg) as a pale yellow powder.
MS (APCI) m/z: 357 [M+H]⁺

(2) The compound obtained in the above step (1) (140 mg) was treated in the same manner as described in Reference Example 1(3) to give 7-amino-5-cyclopropyl -4-(4-fluorophenyl)-2,2-dimethyl-2H-1,4-benzoxazin-3(4H)-one (116 mg) as a brown powder.
MS (APCI) m/z; 327 [M+H]⁺

Reference Example 175

(1) Ozone was passed through a solution of 4-(4-fluorophenyl)-2,2-dimethyl-7-nitro-5-vinyl-2H-1,4-benzoxazin-3(4H)-one (compound obtained in Reference Example 144 (1), 500 mg) in dichloromethane (20 mL) under cooling in a dry ice-acetone bath for 15 minutes. Argon was passed through the reaction mixture to remove excess amount of ozone, and thereto was added dimethylsulfide (0.22 mL). The mixture was stirred at room temperature and concentrated in vacuo. The resultant residue was purified by column chromatography on silica gel (Solvent; n-hexane/ethyl acetate=90/10→65/35) to give 5-cyclopropyl-4-(4-fluorophenyl)-2,2-dimethyl-7-nitro-3-oxo-3,4-dihydro-2H-1,4-benzoxazin-5-carbaldehyde (1.42 g) as a pale yellow powder.

(2) To a solution of the compound obtained in the above step (1) (200 mg) in ethanol (7 mL) was added sodium borohydride (33 mg), and the mixture was stirred at room temperature for 2 hours. The reaction mixture was poured to water, and the mixture was extracted with ethyl acetate. The organic layer was washed with brine, dried over sodium sulfate and concentrated in vacuo. The resultant residue was purified by column chromatography on silica gel (Solvent; n-hexane/ethyl acetate=95/5→50/50) to give 4-(4-fluorophenyl)-5-(hydroxymethyl-2,2-dimethyl-7-nitro-2H-1,4-benzoxazin-3(4H)-one (156 mg) as a pale yellow powder.
MS (APCI) m/z: 364 [M+NH₄]⁺

(3) The compound obtained in the above step (2) (150 mg) was treated in the same manner as described in Reference Example 1(3) to give 7-amino-4-(4-fluorophenyl) -5-(hydroxymethyl)-2,2-dimethyl-2H-1,4-benzoxazin-3(4H)-one (120 mg) as a pale brown powder.
MS (APCI) m/z: 317 [M+H]⁺

Reference Example 176

The corresponding starting materials were treated in the same manner as described in Reference Example 63 to give 7-amino-2,2-dimethyl-4-(1H-pyrrol-1-yl) -2H-1,4-benzoxazin-3(4H)-one as a colorless powder.
MS (APCI) m/z: 258 [M+H]⁺

Reference Examples 177 to 184

The corresponding starting materials were treated in the same manner as described in Reference Example 145 to give compounds shown in the following Table 52.

TABLE 52

Structure: benzoxazin-3(4H)-one with R⁰ at 5-position, Ar at N-4, 2,2-dimethyl, H₂N at 7-position.

| Ref. Ex. Nos. | R⁰ | Ar | Physicochemical properties etc. |
|---|---|---|---|
| 177 | F | 4-Cl-2-F-phenyl | MS(APCI)m/z: 339/341 [M + H]⁺ |
| 178 | F | 6-Cl-3-methylpyridin-2-yl | MS(APCI)m/z: 336/338 [M + H]⁺ |

TABLE 52-continued

[Structure: benzoxazinone with R⁰ at top-left position, Ar on N, H₂N on ring, and geminal dimethyl with O in ring; two CH₃ groups on carbon adjacent to O]

| Ref. Ex. Nos. | R⁰ | Ar | Physicochemical properties etc. |
|---|---|---|---|
| 179 | H | F₃C-pyridine-Cl (2-CF₃, 6-Cl, 3-methyl pyridinyl) | MS(APCI)m/z: 372/374 [M + H]⁺ |
| 180 | H | F₃C-pyridine-CH₃ | MS(APCI)m/z: 352[M + H]⁺ |
| 181 | H | pyridine with CH₃ and F₃C | MS(APCI)m/z: 352[M + H]⁺ |
| 182 | H | pyridine with CH₃ and F₃C | MS(APCI)m/z: 352[M + H]⁺ |
| 183 | F | difluorobenzodioxole-Cl | MS(APCI)m/z: 401/403 [M + H]⁺ |
| 184 | F | difluorobenzodioxole-methyl | MS(APCI)m/z: 367[M + H]⁺ |

Reference Example 185

The corresponding starting materials were treated in the same manner as described in Reference Example 60 to give 7-amino-4-(4-fluorophenyl)-2-methyl-2-phenyl-2H-1,4-benzoxazin-3(4H)-one as a colorless powder.
MS (APCI) m/z: 349 [M+H]⁺

Reference Example 186

(1) To a solution of diisopropylamine (1.42 mL) in tetrahydrofuran (15 mL) was added dropwise 1.6 M n-butyl lithium-n-hexane solution (6.37 mL) cooled in a dry ice-acetone bath under argon atmosphere, and the mixture was stirred at the same temperature for 20 minutes. Thereto was added dropwise a solution of 2-chloro-6-(trifluoromethyl)pyridine (1.81 g) in tetrahydrofuran (5 mL), and the mixture was stirred for 2 hours. To the reaction mixture was added methyl iodide (0.69 mL), and the mixture was stirred at room temperature for 2 hours. The reaction mixture was diluted with water and extracted with diethylether. The organic layer was washed successively with 0.5N HCl, water, an aqueous saturated sodium hydrogencarbonate solution and bribe, dried over sodium sulfate and concentrated in vacuo. The resultant residue was purified by column chromatography on silica gel (Solvent; n-hexane→n-hexane/ethyl acetate=90/10) to give 2-chloro-3-methyl-6-(trifluoromethyl)pyridine (0.90 g) as a yellow powder.
MS (APCI) m/z: 196/198 [M+H]⁺

(2) To a mixture of the compound obtained in the above step (1) (0.78 g), sodium iodide (1.80 g) and propionitrile (8 mL) was added trimethylsilyl chloride (0.51 mL), and the mixture was heated at 105° C. for 2 days. The reaction mixture was poured to ice-water and extracted with diethylether. The organic layer was washed successively with water, an aqueous 10% sodium thiosulfate solution, water and brine, dried over sodium sulfate and concentrated in vacuo. The resultant residue was triturated with cooled n-hexane to give 2-iodo-3-methyl-6-(trifluoromethyl)-pyridine (0.27 g) as a pale yellow powder.
MS (APCI) m/z: 288 [M+H]⁺

Reference Example 187

A mixture of 2-amino-3-chloro-5-(trifluoromethyl)pyridine (393 mg), trimethylboroxine (0.42 mL), 2-dicyclohexylphosphino-2',4',6'-triisopropyl-1,1'-biphenyl (38 mg), tris(dibenzylideneacetone)dipalladium(0) (18 mg), potassium phosphate (850 mg) and dioxane (4 mL) was heated at 100° C. under argon atmosphere for 1 hour. After cooling, to the reaction mixture was added cold water, and the mixture was extracted with ethyl acetate. The organic layer was washed successively with water and brine, dried over sodium sulfate and concentrated in vacuo. The resultant residue was purified by column chromatography on silica gel (Solvent; n-hexane/ethyl acetate=70/30→30/70) to give 2-chloro-3-methyl-5-(trifluoromethyl)pyridine (264 mg) as a colorless powder.
MS (APCI) m/z: 177 [M+H]⁺

Reference Example 188

3-Amino-2-chloro-6-(trifluoromethyl)pyridine (393 mg) was treated in the same manner as described in Reference Example 187 to give 3-amino-2-methyl-6-(trifluoromethyl)pyridine (118 mg) as a pale green powder.
MS (APCI) m/z: 177 [M+H]⁺

Reference Example 189

(1) To a solution of 2-chloro-3-nitro-5-(trifluoromethyl)pyridine (1.87 g) in ethyl acetate (40 mL) was added tin(II) chloride dihydrate (8.22 g), and the mixture was stirred at 80° C. for 2 hours. After cooling, to the reaction mixture was added an aqueous saturated sodium hydrogencarbonate solution, and the mixture was vigorously stirred at room temperature and filtered through a celite pad. The residue was washed with ethyl acetate. The filtrate was combined with the washings, washed successively with an aqueous saturated sodium hydrogencarbonate solution, water and brine, dried over sodium sulfate and concentrated in vacuo. The resultant residue was triturated with n-hexane to give 3-amino-2-chloro-5-(trifluoromethyl)pyridine (0.99 g) as a pale yellow powder.
MS (APCI) m/z: 197/199 [M+H]⁺

(2) To a solution of the compound obtained in the above step (1) (0885 mg), triethylamine (1.25 mL) and 4-dimethylaminopyridine (550 mg) in dichloromethane (30 mL) was added dropwise acetyl chloride (0.48 mL) under ice-cooling, and the mixture was stirred at room temperature for 15 hours. Thereto were further added acetyl chloride (0.48 mL) and triethylamine 1.25 mL), and the mixture was stirred at room temperature for 5 hours. To the reaction mixture was added water, and the mixture was stirred at room temperature for 30 minutes. The organic layer was separated, washed successively with an aqueous saturated sodium hydrogencarbonate solution and brine, dried over sodium sulfate and concentrated in vacuo. The resultant residue was purified by column chromatography on silica gel (Solvent; n-hexane/ethyl acetate=70/30→30/70) and triturated in n-hexane/ethyl acetate to give N-[2-chloro-5-(trifluoromethyl)pyridin-3-yl]-acetamide (0.38 g) as a pale yellow powder.
MS (ESI) m/z: 237/239 [M−H]⁻

(3) A mixture of the compound obtained in the above step (2) (358 mg), trimethylboroxine (315 µL), 2-dicyclohexylphosphino-2',6'-dimethoxybiphenyl (62 mg), palladium acetate (17 mg, potassium carbonate (622 mg) and acetonitrile/water (2.5 mL/1.5 mL) was heated at 100° C. under argon atmosphere—for 1 hour. To the reaction mixture were further added trimethylboroxine (315 µL), 2-dicyclohexylphosphino-2',6'-dimethoxybiphenyl (62 mg) and palladium acetate (17 mg), and the mixture was stirred under heating (100° C.) for 14 hours. After cooling, to the reaction mixture were added water and ethyl acetate and filtered through a celite pad. The organic layer was separated, and the aqueous layer was extracted with ethyl acetate again. The combined organic layer was washed with brine, dried over sodium sulfate, treated with activated charcoal and concentrated in vacuo. The resultant residue was purified by column chromatography on silica gel (Solvent; n-hexane/ethyl acetate=50/50→ethyl acetate) and triturated with n-hexane/ethyl acetate to give N-[2-methyl-5-(trifluoromethyl)-pyridin-3-yl]acetamide (179 mg) as a colorless powder.
MS (APCI) m/z: 219 [M+H]⁺

(4) A suspension of the compound obtained in the above step (3) (170 mg) in 6N HCl was refluxed under heating for 1 hour. The reaction mixture was basified with an aqueous saturated sodium carbonate solution, extracted with ethyl acetate, dried over sodium sulfate and concentrated in vacuo. The resultant residue was recrystallized from n-hexane to give 3-amino-2-methyl-5-(trifluoromethyl)pyridine (98 mg) as a colorless powder.
MS (APCI) m/z: 177 [M+H]⁺

Reference Example 190

(1) To a suspension of 2,2-dimethyl-7-nitro-2H-1,4-benzoxazin-3(4H)-one (compound obtained in Reference Example 1(1), 1.00 g) in dichloromethane (50 mL) was added bis(pyridine)iodonium tetrafluoroborate (1.68 g), and the mixture was stirred at room temperature for 1 hour. To the reaction mixture were further added bis(pyridine)-iodonium tetrafluoroborate (0.84 g) and trifluoromethanesulfonic acid (1.2 mL), and the mixture was stirred at room temperature for 15 hours. The reaction mixture was concentrated in vacuo. The resultant residue was diluted with ethyl acetate, tetrahydrofuran and water, and the mixture was extracted with ethyl acetate. The organic layer was washed successively with an aqueous saturated sodium hydrogencarbonate solution, an aqueous 15% sodium thiosulfate solution, water and brine, dried over sodium sulfate and concentrated in vacuo. The resultant residue was triturated in n-hexane/ethyl acetate to give 5-iodo-2,2-dimethyl-7-nitro-2H-1,4-benzoxazin-3(4H)-one (0.90 g) as a pale brown powder.
MS (ESI) m/z: 347 [M−H]⁻

(2) The compound obtained in the above step (1) (0.90 g) and 4-fluorophenylboronic acid (1.44 g) were treated in the same manner as described in Reference Example 1(2) to give 4-(4-fluorophenyl)-5-iodo-2,2-dimethyl-7-nitro-2H -1,4-benzoxazin-3(4H)-one (0.16 g) as a brown powder.
MS (APCI) m/z: 443 [M+H]⁺

(3) To a solution of the compound obtained in the above step (2) (160 mg) in N-methylpyrrolidone (3 mL) were added successively methyl 2,2-difluoro-2-(fluorosulfonyl)acetate (0.046 mL) and copper(I) bromide (5.5 mg), and the mixture was stirred at 120° C. for 17 hours. The reaction mixture was diluted with water, and the mixture was extracted with ethyl acetate. The organic layer was washed with water and brine, dried over sodium sulfate and concentrated in vacuo. The resultant residue was purified by column chromatography on silica gel (Solvent; n-hexane/ethyl acetate=95/5 to 70/30) to give 4-(4-fluorophenyl)-2,2-dimethyl-7-nitro-5-(trifluoromethyl)-2H -1,4-benzoxazin-3(4H)-one (94 mg) as a pale yellow powder.

(4) The compound obtained in the above step (3) (90 mg) was treated in the same manner as described in Reference Example 1(3) to give 7-amino-4-(4-fluorophenyl)-2,2-dimethyl-5-(trifluoromethyl)-2H-1,4-benzoxazin-3(4H)-one (73 mg) as a pale brown powder.
MS (APCI) m/z: 355 [M+H]⁺

Reference Example 191

7-Amino-4-(4-fluorophenyl)-2,2-dimethyl-5-(trifluoromethyl)-2H-1,4-benzoxazin-3(4H)-one (compound obtained in Reference Example 3(1), 200 mg) and 2-bromobenzothiazole (445 mg) were treated in the same manner as described in Reference Example 61 to give 7-amino-4-(1,3-benzothiazol-2-yl)-2,2-dimethyl-5-(trifluoromethyl)-2H-1,4-benzoxazin-3(4H)-one (12 mg) as a pale yellow powder.
MS (APCI) m/z: 326 [M+H]⁺

Reference Example 192

(1) To 2-amino-3-fluoro-5-nitrophenol (1.00 g) was added water (7 mL) and 48% hydrobromic acid (3 mL), and thereto was added dropwise gradually a solution of sodium nitrite (0.41 g) in water (2 ml) under cooling in ice/NaCl bath to obtain a diazonium salt solution. The mixture was stirred at the same temperature for 15 minutes. To a solution of copper (I) bromide (0.96 g) in water (5 mL) and 48% hydrobromic acid was added dropwise gradually the diazonium salt solution under ice-cooling. The mixture was stirred at 50° C. for 30 minutes. After cooling to room temperature, the reaction mixture was extracted with ethyl acetate. The organic layer was washed with water and brine, dried over magnesium sulfate and concentrated in vacuo. The resultant residue was purified by column chromatography on silica gel (Solvent; n-hexane/ethyl acetate=90/10→70/30) to obtain 2-bromo-3-fluoro-5-nitrophenol (1.15 g) as a pale yellow powder.
MS (ESI) m/z: 234/236 [M−H]⁻

(2) The compound obtained in the above step (1) (1.14 g) and ethyl α-bromoisobutyrate (0.93 mL) were treated in the same manner as described in Reference Example 62(1) to give ethyl 2-(2-bromo-3-fluoro-5-nitrophenoxy)-2-methylpropionate (0.85 g) as a pale yellow viscous oil.
MS (APCI) m/z: 367/369 [M+NH₄]⁺

(3) The compound obtained in the above step (2) (0.85 g) was treated in the same manner as described in Reference Example 63(1) to give 2-(2-bromo-3-fluoro-5-nitrophenoxy)-2-methylpropionic acid (0.60 g) as a pale yellow powder.
MS (ESI) m/z: 320/322 [M−H]⁻

(4) The compound obtained in the above step (3) (150 mg) and 2-amino-5-bromo-3-methylpyridine (104 mg) were treated in the same manner as described in Reference Example 145(1) to give 2-(2-bromo-3-fluoro-5-nitrophenoxy)-N-(5-bromo-3-methyl-pyridin-2-yl)-2-methylpropionamide (117 mg) as a colorless powder.
MS (APCI) m/z: 490/492 [M+H]$^+$ (5) To a solution of the compound obtained in the above step (4) (115 mg) in dimethylsulfoxide (7 mL) was added potassium carbonate (35 mg), and the mixture was stirred at 50° C. for 1.5 hours. After cooling to room temperature, the reaction mixture was diluted with ethyl acetate and washed successively with an aqueous ammonium chloride solution and water. The organic layer was dried over magnesium sulfate and concentrated in vacuo. The resultant residue was purified by column chromatography on silica gel (Solvent; n-hexane/ethyl acetate=95/5→80/20) to give 4-(5-bromo-3-methylpyridin-2-yl)-5-fluoro-2,2-dimethyl-7-nitro-2H-1,4-benzoxazin-3(4H)-one (72 mg) as a colorless powder.
MS (APCI) m/z: 410/412 [M+H]$^+$ (6) The compound obtained in the above step (5) (66 mg) was treated in the same manner as described in Reference Example 1(3) to give 7-amino-4-(5-bromo-3-methylpyridin-2-yl)-5-fluoro-2,2-dimethyl-2H-1,4-benzoxazin-3(4H)-one (55 mg) as a colorless powder.
MS (APCI) m/z: 380/382 [M+H]$^+$ Reference Examples 193 to 196

The corresponding starting materials were treated in the same manner as described in Reference Example 192(2) to (6) to give compounds shown in the following Table 53.

TABLE 53

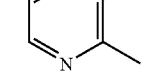

| Ref. Ex. Nos. | R$^0$ | Ar | Physicochemical properties etc. |
|---|---|---|---|
| 193 | F | 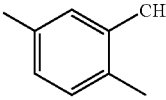 | MS(APCI)m/z: 370[M + H]$^+$ |
| 194 | F | 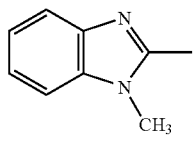 | MS(APCI)m/z: 335/337[M + H]$^+$ |
| 195 | H |  | MS(APCI)m/z: 323[M + H]$^+$ |

Experiment 1

[Aldosterone Receptor Binding Assay]

(1) Preparation of Kidney Cytosol Fraction:

Kidneys derived from post-adrenalectomy Sprague-Dawley male rats (7 weeks old) were homogenized in the following buffer solution and the homogenate was centrifuged at 100,000×g for 1 hour to give a supernatant as a kidney cytosol fraction (protein concentration: 15 mg/mL) for the present biding assay.

Composition of Buffer solution: 50 mM Tris-HCl (pH 7.5), 250 mM Sucrose, 50 mM Potassium chloride, 3 mM Magnesium chloride, 20 mM Sodium molybdate and 1 mM Mercaptoethanol (2) Binding Assay:

A mixture of 5 µL of a solution of each test compound in dimethylsulfoxide, 200 µL of kidney cytosol fraction, 50 µL of physiological saline (or 50 µL of unlabeled aldosterone solution (final concentration: 1 µM) and (50 µL of [$^3$H]aldosterone solution (ca. 2 nM) was incubated in a test tube at 4° C. overnight. Thereto was added 100 µL of dextrane-coated charcoal/10 mM Tris-HCl buffer and the mixture was incubated at 4° C. for 30 minutes. The reaction mixture was centrifuged at 3000 rpm for 10 minutes and to the supernatant (150 µL) was added 5 mL of a scintillator (Clearsol II, Nakarai Tesque). The radioactivity was measured by a liquid scintillation counter (TRI CARB 2200CA, Packard). The concentration of each test compound required to produce 50% inhibition of aldosterone-binding to receptors (IC$_{50}$; µM) was calculated on the basis of the above quantitated radioactivity. Moreover, the dissociation constant (Ki) of each test compound was calculated on Cheng and Prusoff's equation (Ki=IC$_{50}$/(1+[L]/Kd), wherein [L] is [$^3$H]aldosterone concentration and Kd is the affinity constant of aldosterone).

(3) Results:

The results of the present binding assay are shown in the following Table 54. Meanwhile, the symbols (++ and +++) are defined as follows:

TABLE 54

| Test compound | Ki |
|---|---|
| Compound of Example 6 | +++ |
| Compound of Example 9 | +++ |
| Compound of Example 10 | +++ |
| Compound of Example 11 | +++ |
| Compound of Example 12 | +++ |
| Compound of Example 15 | +++ |
| Compound of Example 19 | +++ |
| Compound of Example 31 | +++ |
| Compound of Example 37 | ++ |
| Compound of Example 45 | +++ |
| Compound of Example 46 | +++ |
| Compound of Example 50 | +++ |
| Compound of Example 53 | +++ |
| Compound of Example 55 | +++ |
| Compound of Example 64 | +++ |
| Compound of Example 67 | ++ |
| Compound of Example 72 | +++ |
| Compound of Example 73 | +++ |
| Compound of Example 77 | +++ |
| Compound of Example 78 | +++ |
| Compound of Example 79 | +++ |
| Compound of Example 84 | +++ |
| Compound of Example 101 | +++ |
| Compound of Example 110 | ++ |
| Compound of Example 112 | +++ |
| Compound of Example 129 | +++ |

++: 0.5 µM < Ki < 1 µM
+++: ki ≤ 0.5 µM

INDUSTRIAL APPLICABILITY OF INVENTION

The compound [I] of the present invention shows a high affinity to mineralocorticoid receptor (MR) and thereby a modulating activity (e.g., antagonizing activity) on the receptor. For example, in a binding assay using rat MR and $^3$H-aldosterone, which was conducted in accordance with a manner as described in The Journal of Pharmacology and Experimental Therapeutics, 1987; 240: p. 650-656, N-(3-oxo-2,4-diphenyl-3,4-dihydro-2H-1,4-benzoxazin-7-yl)methanesulfonamide or N-(2,2-dimethyl-3-oxo-4-phenyl-3,4-dihydro-2H-1, 4-benzoxazin-7-yl)methanesulfonamide, the compound of the present invention, showed an $IC_{50}$ value lower than 10 μM in aldosterone-binding to MR. Therefore, the compound [I] of the present invention is useful as a medicament for prevention or treatment of various diseases associated with the receptor and/or aldosterone, such as cardiovascular diseases including hypertension and heart failure.

The invention claimed is:
1. A compound of the following formula [I]:

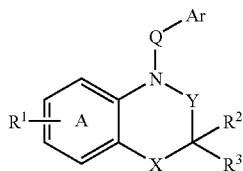

wherein
Ring A is a benzene ring optionally substituted by one to three group(s) selected from (a) a halogen atom, (b) a $C_{1-6}$ alkyl group, said alkyl group being optionally substituted by one to three group(s) selected from a halogen atom, a hydroxyl group, and a $C_{1-6}$ alkoxy group, (c) a hydroxyl group, (d) a $C_{1-6}$ alkoxy group, (e) an amino group, (f) a cyano group, (g) a $C_{2-12}$ alkenyl group, (h) a $C_{1-7}$ alkanoyl group, and (j) a $C_{3-10}$ cycloalkyl group,
$R^1$ is located at the 7-position of the 1,4-benzoxazine moiety and is a group of the formula: $R^aSO_2NH-$, $R^aSO_2NH-CH_2-$ or $(R^b)(R^c)NSO_2-$, wherein $R^a$ is a $C_{1-6}$ alkyl group, a $C_{3-10}$ cycloalkyl group, an amino group optionally substituted by one or two $C_{1-6}$ alkyl group(s), a 6- to 10-membered monocyclic or bicyclic aryl group, or a 5- to 10-membered monocyclic or bicyclic heteroaryl group containing one to two heteroatom(s) selected from an oxygen atom, a sulfur atom, and a nitrogen atom, $R^b$ and $R^c$ are the same or different and are each a hydrogen atom, a $C_{1-6}$ alkyl group, or a $C_{3-10}$ cycloalkyl group,
one of $R^2$ and $R^3$ is a hydrogen atom, a halogen atom, or a $C_{1-6}$ alkyl group, and the other is a hydrogen atom, a $C_{1-6}$ alkyl group, a $C_{1-6}$ alkoxycarbonyl group, or a phenyl group, or both $R^2$ and $R^3$ combine each other together with the adjacent carbon atom to form a $C_{3-10}$ cycloalkyl group,
X is an oxygen atom,
Y is a group of the formula: $-C(=O)-$, $-C(=S)-$, or $-CH(R^5)-$, wherein $R^5$ is a hydrogen atom or a phenyl group,
Ar is a 6- to 10-membered monocyclic or bicyclic aryl group or a 5- to 10-membered monocyclic or bicyclic heteroaryl group containing one to two heteroatom(s) selected from an oxygen atom, a sulfur atom, and a nitrogen atom, and said aryl or heteroaryl group is optionally substituted by one to three group(s) selected from (a) a halogen atom, (b) a hydroxyl group, (c) a cyano group, (d) a $C_{1-6}$ alkyl group optionally substituted by one to three halogen atom(s), (e) a hydroxyl-$C_{1-6}$ alkyl group, (f) a benzoyloxymethyl group, (g) a $C_{1-6}$ alkoxy group optionally substituted by one to three halogen atom(s), (h) a $C_{1-6}$ alkoxycarbonyl-$C_{1-6}$ alkoxy group, (i) a $C_{1-6}$ alkylthio group, (j) a $C_{1-6}$ alkylenedioxy group optionally substituted by one to two halogen atom(s), (k) an amino group optionally substituted by one to two $C_{1-6}$ alkyl group(s), (l) an acylamino group, said acyl group being a $C_{1-6}$ alkanoyl group or a benzoyl group, (m) $C_{3-10}$ cycloalkyl group, and (n) a $C_{1-6}$ alkylsulfonyl group, and
Q is a single bond, a $C_{1-6}$ alkylene group or a $C_{1-6}$ alkenylene group, or
a pharmaceutically acceptable salt thereof.
2. A compound of the following formula [I-a]:

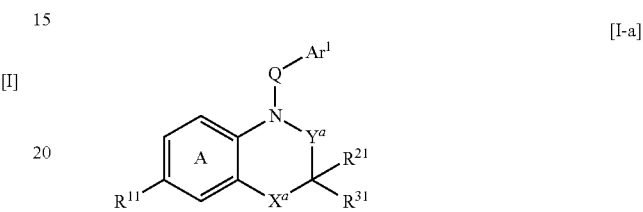

wherein
Ring A is a benzene ring optionally substituted by one to three group(s) selected from (a) a halogen atom, (b) a $C_{1-6}$ alkyl group, said alkyl group being optionally substituted by one to three group(s) selected from a halogen atom, a hydroxyl group, and a $C_{1-6}$ alkoxy group, (c) a hydroxyl group, (d) a $C_{1-6}$ alkoxy group, (e) an amino group, (i) a $C_{2-12}$ alkenyl group, (j) a $C_{1-7}$ alkanoyl group, and (k) a $C_{3-10}$ cycloalkyl group,
$R^{11}$ is a group of the formula: $R^{aa}SO_2NH-$, $R^{aa}SO_2NH-CH_2-$ or $(R^b)(R^c)NSO_2-$, wherein $R^a$ is a $C_{1-6}$ alkyl group, a $C_{3-10}$ cycloalkyl group, an amino group optionally substituted by one or two $C_{1-6}$ alkyl group(s), a phenyl group, or a 5- to 6-membered monocyclic heteroaryl group containing one to two heteroatom(s) selected from an oxygen atom, a sulfur atom, and a nitrogen atom, $R^b$ and $R^c$ are the same or different and are each a hydrogen atom, a $C_{1-6}$ alkyl group, or a $C_{3-10}$ cycloalkyl group,
one of $R^{21}$ and $R^{31}$ is a hydrogen atom, a halogen atom or a $C_{1-6}$ alkyl group, and another is a hydrogen atom, a $C_{1-6}$ alkyl group, a $C_{1-6}$ alkoxycarbonyl group, or a phenyl group, or both of them combine each other together with the adjacent carbon atom to form a $C_{3-8}$ cycloalkyl group,
$X^a$ is an oxygen atom,
$Y^a$ is a group of the formula: $-C(=O)-$, $-C(=S)-$ or $-CH(R^{51})-$, wherein $R^{51}$ is a hydrogen atom or a phenyl group,
$Ar^1$ is
(a) a phenyl group optionally substituted by one to three group(s) selected from a halogen atom, a hydroxyl group, a cyano group, a nitro group, a $C_{1-6}$ alkyl group optionally substituted by one to three halogen atom(s), a hydroxy-$C_{1-6}$ alkyl group, a benzoyloxymethyl group, a $C_{1-6}$ alkoxy group optionally substituted by one to three halogen atom(s), a $C_{1-6}$ alkoxycarbonyl-$C_{1-6}$alkoxy group, a $C_{1-6}$ alkylthio group, a $C_{1-6}$ alkylenedioxy group optionally substituted by one to two halogen atom(s), an amino group optionally substituted by one or two $C_{1-6}$ alkyl group(s), a $C_{1-7}$ alkanoylamino group, a $C_{1-6}$ alkoxycarbonylamino group, a $C_{3-10}$ cycloalkyl group, and a $C_{1-6}$ alkylsulfonyl group;

(b) a thienyl group optionally substituted by one to two group(s) selected from a halogen atom and a trihalogeno$C_{1-6}$ alkyl group, said thienyl group being optionally fused to a benzene ring;

(c) a pyridyl group optionally substituted by one to two group(s) selected from a halogen atom, a nitro group, a $C_{1-6}$ alkyl group and a trihalogeno$C_{1-6}$ alkyl group;

(d) a pyrimidinyl group optionally substituted by a halogen atom;

(e) a quinolyl group;

(f) a pyridazinyl group optionally substituted by a halogen atom;

(g) a pyrrolyl group;

(h) a furyl group optionally fused to a benzene ring;

(i) a thiazolyl group optionally fused to a benzene ring;

(j) an imidazolyl group optionally fused to a benzene ring and optionally substituted by a $C_{1-6}$ alkyl group; or (k) a naphthyl group, and Q is a single bond, a $C_{1-6}$ alkylene group, or a $C_{1-6}$ alkenylene group, or a pharmaceutically acceptable salt thereof.

3. The compound according to claim 2 wherein both $R^{21}$ and $R^{31}$ are a hydrogen atom.

4. The compound according to claim 2 wherein $R^{21}$ is a hydrogen atom and $R^{31}$ is a $C_{1-4}$ alkyl group.

5. The compound according to claim 2 wherein $R^{21}$ is a hydrogen atom or a $C_{1-4}$ alkyl group and $R^{31}$ is a phenyl group.

6. The compound according to claim 2 wherein both $R^{21}$ and $R^{31}$ are a $C_{1-4}$ alkyl group.

7. The compound according to claim 2 wherein $R^{21}$ is a hydrogen atom and $R^{31}$ is a halogen atom.

8. The compound according to claim 2 wherein $R^{21}$ and $R^{31}$ combine each other together with the adjacent carbon atom to form a $C_{3-8}$ cycloalkyl group.

9. A compound selected from the group consisting of:
N-(3-oxo-2,4-diphenyl-3,4-dihydro-2H-1,4-benzoxazin-7-yl)-methanesulfonamide;
N-[4-(4-fluorophenyl)-3-oxo-2-phenyl-3,4-dihydro-2H-1,4-benzoxazin-7-yl]methanesulfonamide;
N-[4-(4-chlorophenyl)-3-oxo-2-phenyl-3,4-dihydro-2H-1,4-benzoxazin-7-yl]-methanesulfonamide;
N-(2,2-dimethyl-3-oxo-4-phenyl-3,4-dihydro-2H-1,4-benzoxazin-7-yl)-methanesulfonamide;
N-[4-(4-fluorophenyl)-2,2-dimethyl-3-oxo-3,4-dihydro-2H-1,4-benzoxazin-7-yl]-methanesulfonamide;
N-[4-(4-chlorophenyl)-2,2-dimethyl-3-oxo-3,4-dihydro-2H-1,4-benzoxazin-7-yl]-methanesulfonamide;
N-[4-(3,4-difluorophenyl)-2,2-dimethyl-3-oxo-3,4-dihydro-2H-1,4-benzoxazin-7-yl]methanesulfonamide;
N-[4-(4-fluoro-3-methylphenyl)-2,2-dimethyl-3-oxo-3,4-dihydro-2H-1,4-benzoxazin-7-yl]methanesulfonamide;
N-[4-(3-chloro-4-fluorophenyl)-2,2-dimethyl-3-oxo-3,4-dihydro-2H-1,4-benzoxazin-7-yl]methanesulfonamide;
N-[4-(4-methoxyphenyl)-2,2-dimethyl-3-oxo-3,4-dihydro-2H-1,4-benzoxazin-7-yl]methanesulfonamide;
N-[4-(4-fluorophenyl)-2,2-dimethyl-3-oxo-3,4-dihydro-2H-1,4-benzoxazin-7-yl]ethanesulfonamide;
N-[4-(5-fluoropyridin-2-yl)-2,2-dimethyl-3-oxo-3,4-dihydro-2H-1,4-benzoxazin-7-yl]methanesulfonamide;
N-(4-benzyl-2,2-dimethyl-3-oxo-3,4-dihydro-2H-1,4-benzoxazin-7-yl)-methanesulfonamide;
N-(4-benzyl-3-oxo-3,4-dihydro-2H-1,4-benzoxazin-7-yl)methanesulfonamide;
N-[4-(4-fluorophenyl)-2-methyl-3-oxo-3,4-dihydro-2H-1,4-benzoxazin-7-yl]-methanesulfonamide;
4-(4-fluorophenyl)-N,2,2-trimethyl-3-oxo-3,4-dihydro-2H-1,4-benzoxazine-7-sulfonamide;
N-[4-(5-chloro-2-thienyl)-2,2-dimethyl-3-oxo-3,4-dihydro-2H-1,4-benzoxazin-7-yl]methanesulfonamide;
N'-[4-(4-fluorophenyl)-2,2-dimethyl-3-oxo-3,4-dihydro-2H-1,4-benzoxazin-7-yl]-N,N-dimethylsulfamide;
N-[4-(4-fluorophenyl)-2,2-dimethyl-3,4-dihydro-2H-1,4-benzoxazin-7-yl]-methanesulfonamide;
N-[2,2-dimethyl-3-oxo-4-(3-thienyl)-3,4-dihydro-2H-1,4-benzoxazin-7-yl]-methanesulfonamide;
N-[4-(4-fluorophenyl)-3-oxo-3,4-dihydrospiro[1,4-benzoxazine-2,1'-cyclobutan]-7-yl]methanesulfonamide;
N-[4-(4-fluoro-3-trifluoromethyl)phenyl]-2,2-dimethyl-3-oxo-3,4-dihydro-2H-1,4-benzoxazin-7-yl]methanesulfonamide;
N-[2,2-dimethyl-4-(4-methylphenyl)-3-oxo-3,4-dihydro-2H-1,4-benzoxazin-7-yl]methanesulfonamide;
N-[4-(4-fluorophenyl)-3-oxo-3,4-dihydrospiro[1,4-benzoxazin-2,1'-cyclopropan]-7-yl]methanesulfonamide;
N-[2,2-diethyl-4-(4-fluorophenyl)-3-oxo-3,4-dihydro-2H-1,4-benzoxazin-7-yl]-methanesulfonamide;
N-[2-ethyl-4-(4-fluorophenyl)-3-oxo-3,4-dihydro-2H-1,4-benzoxazin-7-yl]-methanesulfonamide;
N-[2,2-dimethyl-3-oxo-4-[(4-trifluoromethyl)phenyl]-3,4-dihydro-2H-1,4-benzoxazin-7-yl]methanesulfonamide;
N-[4-(4-fluorophenyl)-2,2-dimethyl-3-oxo-3,4-dihydro-2H-1,4-benzoxazin-7-yl]sulfamide;
N-[4-(2,4-difluorophenyl)-2,2-dimethyl-3-oxo-3,4-dihydro-2H-1,4-benzoxazin-7-yl]methanesulfonamide;
N-[4-(4-fluorophenyl)-2,2-dimethyl-3-thioxo-3,4-dihydro-2H-1,4-benzoxazin-7-yl]methanesulfonamide;
N-[4-(4-fluoro-2-methylphenyl)-2,2-dimethyl-3-oxo-3,4-dihydro-2H-1,4-benzoxazin-7-yl]methanesulfonamide;
N-[4-(4-chloro-3-methoxyphenyl)-2,2-dimethyl-3-oxo-3,4-dihydro-2H-1,4-benzoxazin-7-yl]methanesulfonamide;
N-[4-(4-fluoro-3-methoxyphenyl)-2,2-dimethyl-3-oxo-3,4-dihydro-2H-1,4-benzoxazin-7-yl]methanesulfonamide;
4-(4-fluoro-3-methylphenyl)-N,2,2-trimethyl-3-oxo-3,4-dihydro-2H-1,4-benzoxazine-7-sulfonamide;
N-[4-[3-(dimethylamino)-4-fluorophenyl]-2,2-dimethyl-3-oxo-3,4-dihydro-2H-1,4-benzoxazin-7-yl]methanesulfonamide;
N-[4-(3-chloro-4-fluorophenyl)-3-oxo-3,4-dihydro-2H-1,4-benzoxazin-7-yl]-methanesulfonamide;
N-[4-(2-chloro-4-fluorophenyl)-2,2-dimethyl-3-oxo-3,4-dihydro-2H-1,4-benzoxazin-7-yl]methanesulfonamide;
N-[4-(4-chloro-2-fluorophenyl)-2,2-dimethyl-3-oxo-3,4-dihydro-2H-1,4-benzoxazin-7-yl]methanesulfonamide;
N-[4-(4-chloro-2-methylphenyl)-2,2-dimethyl-3-oxo-3,4-dihydro-2H-1,4-benzoxazin-7-yl]methanesulfonamide;
N-[4-(4-bromophenyl)-2,2-dimethyl-3-oxo-3,4-dihydro-2H-1,4-benzoxazin-7-yl]methanesulfonamide;
N-[4-(4-fluorophenyl)-2,2,6-trimethyl-3-oxo-3,4-dihydro-2H-1,4-benzoxazin-7-yl]methanesulfonamide;
N-[6-amino-4-(4-fluorophenyl)-2,2-dimethyl-3-oxo-3,4-dihydro-2H-1,4-benzoxazin-7-yl]methanesulfonamide;

N-[4-[3-(difluoromethyl)-4-fluorophenyl]-2,2-dimethyl-3-oxo-3,4-dihydro-2H -1,4-benzoxazin-7-yl]methanesulfonamide;
4-(4-chlorophenyl)-N,2,2-trimethyl-3-oxo-3,4-dihydro-2H-1,4-benzoxazine -7-sulfonamide;
N-[4-(4-chloro-2-cyanophenyl)-2,2-dimethyl-3-oxo-3,4-dihydro-2H-1,4-benzoxazin-7-yl]methanesulfonamide;
4-(4-bromophenyl)-N,2,2-trimethyl-3-oxo-3,4-dihydro-2H-1,4-benzoxazine -7-sulfonamide;
N-[4-(5-chloropyridin-2-yl)-2,2-dimethyl-3-oxo-3,4-dihydro-2H-1,4-benzoxazin-7-yl]methanesulfonamide;
N-[5-chloro-4-(4-fluorophenyl)-2,2-dimethyl-3-oxo-3,4-dihydro-2H-1,4-benzoxazin-7-yl]methanesulfonamide;
N-[4-(4-bromo-2-methylphenyl)-2,2-dimethyl-3-oxo-3,4-dihydro-2H-1,4-benzoxazin-7-yl]methanesulfonamide;
N-[4-[4-chloro-3-(trifluoromethyl)phenyl]-2,2-dimethyl-3-oxo-3,4-dihydro-2H -1,4-benzoxazin-7-yl]methanesulfonamide;
N-[4-[3-fluoro-4-(trifluoromethyl)phenyl]-2,2-dimethyl-3-oxo-3,4-dihydro-2H -1,4-benzoxazin-7-yl]methanesulfonamide;
N-[4-(4-chloro-3-fluorophenyl)-2,2-dimethyl-3-oxo-3,4-dihydro-2H-1,4-benzoxazin-7-yl]methanesulfonamide;
N-[4-(4-chloro-3-methylphenyl)-2,2-dimethyl-3-oxo-3,4-dihydro-2H-1,4-benzoxazin-7-yl]methanesulfonamide;
N-[4-(3-fluoro-4-methylphenyl)-2,2-dimethyl-3-oxo-3,4-dihydro-2H-1,4-benzoxazin-7-yl]methanesulfonamide;
4-(4-chloro-2-methylphenyl)-N,2,2-trimethyl-3-oxo-3,4-dihydro-2H-1,4-benzoxazine-7-sulfonamide;
N-[4-(2,4-dimethylphenyl)-2,2-dimethyl-3-oxo-3,4-dihydro-2H-1,4-benzoxazin -7-yl]methanesulfonamide;
N-[4-(3-chloro-4-methylphenyl)-2,2-dimethyl-3-oxo-3,4-dihydro-2H-1,4-benzoxazin-7-yl]methanesulfonamide;
N-[4-(3,4-difluoro-5-methoxyphenyl)-2,2-dimethyl-3-oxo-3,4-dihydro-2H-1,4-benzoxazin-7-yl]methanesulfonamide;
N-[4-(3,4-dichlorophenyl)-2,2-dimethyl-3-oxo-3,4-dihydro-2H-1,4-benzoxazin -7-yl]methanesulfonamide;
N-[2,2-dimethyl-4-(2-naphthyl)-3-oxo-3,4-dihydro-2H-1,4-benzoxazin-7-yl]-methanesulfonamide;
N-[4-(4-fluoro-2,6-dimethylphenyl)-2,2-dimethyl-3-oxo-3,4-dihydro-2H-1,4-benzoxazin-7-yl]methanesulfonamide;
N-[5-bromo-4-(4-fluorophenyl)-2,2-dimethyl-3-oxo-3,4-dihydro-2H-1,4-benzoxazin-7-yl]methanesulfonamide;
N-[4-(5-chloro-2-methylphenyl)-2,2-dimethyl-3-oxo-3,4-dihydro-2H-1,4-benzoxazin-7-yl]methanesulfonamide;
N-[5-chloro-4-(4-chlorophenyl)-2,2-dimethyl-3-oxo-3,4-dihydro-2H-1,4-benzoxazin-7-yl]methanesulfonamide;
N-[4-(4-fluorophenyl)-2,2,5-trimethyl-3-oxo-3,4-dihydro-2H-1,4-benzoxazin -7-yl]methanesulfonamide;
N-[4-(4-bromo-3-methylphenyl)-2,2-dimethyl-3-oxo-3,4-dihydro-2H-1,4-benzoxazin-7-yl]methanesulfonamide;
N-[4-(2,2-difluoro-1,3-benzodioxol-5-yl)-2,2-dimethyl-3-oxo-3,4-dihydro-2H -1,4-benzoxazin-7-yl]methanesulfonamide;
N-(4-mesityl-2,2-dimethyl-3-oxo-3,4-dihydro-2H-1,4-benzoxazin-7-yl) -methanesulfonamide;
N-[4-(2,6-dimethylphenyl)-2,2-dimethyl-3-oxo-3,4-dihydro-2H-1,4-benzoxazin -7-yl]methanesulfonamide;
N-[4-(4-chloro-2,6-dimethylphenyl)-2,2-dimethyl-3-oxo-3,4-dihydro-2H-1,4-benzoxazin-7-yl]methanesulfonamide;
N-[4-(5-bromo-3-methylpyridin-2-yl)-2,2-dimethyl-3-oxo-3,4-dihydro-2H-1,4-benzoxazin-7-yl]methanesulfonamide;
N-[5-fluoro-4-(4-fluorophenyl)-2,2-dimethyl-3-oxo-3,4-dihydro-2H-1,4-benzoxazin-7-yl]methanesulfonamide;
N-[4-(3,5-dichloropyridin-2-yl)-2,2-dimethyl-3-oxo-3,4-dihydro-2H-1,4-benzoxazin-7-yl]methanesulfonamide;
N-[4-(4-fluoro-2,3-dimethylphenyl)-2,2-dimethyl-3-oxo-3,4-dihydro-2H-1,4-benzoxazin-7-yl]methanesulfonamide;
N-[4-(3-chloro-2-methylphenyl)-2,2-dimethyl-3-oxo-3,4-dihydro-2H-1,4-benzoxazin-7-yl]methanesulfonamide;
N-[4-(5-fluoro-2-methylphenyl)-2,2-dimethyl-3-oxo-3,4-dihydro-2H-1,4-benzoxazin-7-yl]methanesulfonamide;
N-[2,2-dimethyl-3-oxo-4-(1-phenylethyl)-3,4-dihydro-2H-1,4-benzoxazin -7-yl]methanesulfonamide;
N-[2,2-dimethyl-4-(3-methylbenzyl)-3-oxo-3,4-dihydro-2H-1,4-benzoxazin -7-yl]methanesulfonamide;
N-[2,2-dimethyl-4-[2-methyl-5-(trifluoromethyl)phenyl]-3-oxo-3,4-dihydro-2H -1,4-benzoxazin-7-yl]methanesulfonamide;
N-[2,2-dimethyl-3-oxo-4-(2,4,6-trifluorophenyl)-3,4-dihydro-2H-1,4-benzoxazin-7-yl]methanesulfonamide;
2-chloro-5-[2,2-dimethyl-7-[(methylsulfonyl)amino]-3-oxo-2,3-dihydro-4H-1,4-benzoxazin-4-yl]benzyl benzoate;
N-[4-(4-chloro-2-methoxy-5-methylphenyl)-2,2-dimethyl-3-oxo-3,4-dihydro -2H-1,4-benzoxazin-7-yl]methanesulfonamide;
N-[4-(6-chloro-2,2-difluoro-1,3-benzodioxol-5-yl)-2,2-dimethyl-3-oxo-3,4-dihydro-2H-1,4-benzoxazin-7-yl]methanesulfonamide;
N-[2,2-dimethyl-4-(3-methyl-5-nitropyridin-2-yl)-3-oxo-3,4-dihydro-2H-1,4-benzoxazin-7-yl]methanesulfonamide;
N-[4-(5-chloro-3-methylpyridin-2-yl)-2,2-dimethyl-3-oxo-3,4-dihydro-2H-1,4-benzoxazin-7-yl]methanesulfonamide;
N-[4-[4-fluoro-2-(trifluoromethyl)phenyl]-2,2-dimethyl-3-oxo-3,4-dihydro-2H -1,4-benzoxazin-7-yl]methanesulfonamide;
N-[2,2-dimethyl-4-[2-methyl-4-(trifluoromethyl)phenyl]-3-oxo-3,4-dihydro-2H -1,4-benzoxazin-7-yl]methanesulfonamide;
N-[4-(4-fluorophenyl)-2,2-dimethyl-3-oxo-5-vinyl-3,4-dihydro-2H-1,4-benzoxazin-7-yl]methanesulfonamide;
N-[4-(4-chlorophenyl)-5-fluoro-2,2-dimethyl-3-oxo-3,4-dihydro-2H-1,4-benzoxazin-7-yl]methanesulfonamide;
N-[4-(5-chloropyridin-2-yl)-5-fluoro-2,2-dimethyl-3-oxo-3,4-dihydro-2H-1,4-benzoxazin-7-yl]methanesulfonamide;
N-[4-[3-chloro-5-(trifluoromethyl)pyridin-2-yl]-2,2-dimethyl-3-oxo-3,4-dihydro-2H-1,4-benzoxazin-7-yl]methanesulfonamide;

N-[4-(3-chlorophenyl)-2,2-dimethyl-3-oxo-3,4-dihydro-2H-1,4-benzoxazin-7-yl]methanesulfonamide;

N-[4-[5-bromo-6-methylpyridin-2-yl)-2,2-dimethyl-3-oxo-3,4-dihydro-2H-1,4-benzoxazin-7-yl]methanesulfonamide;

N-[5-fluoro-4-(5-fluoropyridin-2-yl)-2,2-dimethyl-3-oxo-3,4-dihydro-2H-1,4-benzoxazin-7-yl]methanesulfonamide;

N-[2,2-dimethyl-3-oxo-4-[5-(trifluoromethyl)-2-thienyl]-3,4-dihydro-2H-1,4-benzoxazin-7-yl]methanesulfonamide;

N-[4-(6-chloro-4-methylpyridin-3-yl)-2,2-dimethyl-3-oxo-3,4-dihydro-2H-1,4-benzoxazin-7-yl]methanesulfonamide;

N-[4-(5-bromopyridin-2-yl)-2,2-dimethyl-3-oxo-3,4-dihydro-2H-1,4-benzoxazin-7-yl]methanesulfonamide;

N-[4-[4-chloro-3-(hydroxymethyl)phenyl]-2,2-dimethyl-3-oxo-3,4-dihydro-2H-1,4-benzoxazin-7-yl]methanesulfonamide;

N-[4-(6-bromo-5-methylpyridin-3-yl)-2,2-dimethyl-3-oxo-3,4-dihydro-2H-1,4-benzoxazin-7-yl]methanesulfonamide;

N-[4-(6-chloro-2-methylpyridin-3-yl)-2,2-dimethyl-3-oxo-3,4-dihydro-2H-1,4-benzoxazin-7-yl]methanesulfonamide;

N-{2,2-dimethyl-3-oxo-4-[5-(trifluoromethyl)pyridin-2-yl]-3,4-dihydro-2H-1,4-benzoxazin-7-yl}methanesulfonamide;

N-{2,2-dimethyl-4-[3-methyl-6-(trifluoromethyl)pyridin-2-yl]-3-oxo-3,4-dihydro-2H-1,4-benzoxazin-7-yl}methanesulfonamide;

N-[4-(5-chloro-3-fluoropyridin-2-yl)-2,2-dimethyl-3-oxo-3,4-dihydro-2H-1,4-benzoxazin-7-yl]methanesulfonamide;

N-[4-(3-chlorophenyl)-5-fluoro-2,2-dimethyl-3-oxo-3,4-dihydro-2H-1,4-benzoxazin-7-yl]methanesulfonamide;

N-[4-(5-bromopyridin-2-yl)-5-fluoro-2,2-dimethyl-3-oxo-3,4-dihydro-2H-1,4-benzoxazin-7-yl]methanesulfonamide;

N-[4-(5-chloro-3-methylpyridin-2-yl)-5-fluoro-2,2-dimethyl-3-oxo-3,4-dihydro-2H-1,4-benzoxazin-7-yl]methanesulfonamide;

N-{5-fluoro-2,2-dimethyl-3-oxo-4-[5-(trifluoromethyl)pyridin-2-yl]-3,4-dihydro-2H-1,4-benzoxazin-7-yl}methanesulfonamide;

N-[4-(5-fluoro-3-methylpyridin-2-yl)-2,2-dimethyl-3-oxo-3,4-dihydro-2H-1,4-benzoxazin-7-yl]methanesulfonamide;

N-[4-(5-chloro-3-fluoropyridin-2-yl)-5-fluoro-2,2-dimethyl-3-oxo-3,4-dihydro-2H-1,4-benzoxazin-7-yl]methanesulfonamide;

N-[4-[4-chloro-3-(hydroxymethyl)phenyl]-5-fluoro-2,2-dimethyl-3-oxo-3,4-dihydro-2H-1,4-benzoxazin-7-yl]methanesulfonamide;

2-chloro-5-[5-fluoro-2,2-dimethyl-7-[(methylsulfonyl)amino]-3-oxo-2,3-dihydro-4H-1,4-benzoxazin-4-yl]benzyl benzoate;

N-[4-(2,6-dimethylpyridin-3-yl)-2,2-dimethyl-3-oxo-3,4-dihydro-2H-1,4-benzoxazin-7-yl]methanesulfonamide;

N-[5-cyclopropyl-4-(4-fluorophenyl)-2,2-dimethyl-3-oxo-3,4-dihydro-2H-1,4-benzoxazin-7-yl]methanesulfonamide;

N-[5-fluoro-4-[3-fluoro-4-(trifluoromethyl)phenyl]-2,2-dimethyl-3-oxo-3,4-dihydro-2H-1,4-benzoxazin-7-yl]methanesulfonamide;

N-[5-fluoro-2,2-dimethyl-3-oxo-4-[4-(trifluoromethyl)phenyl]-3,4-dihydro-2H-1,4-benzoxazin-7-yl]methanesulfonamide;

N-[5-fluoro-4-[4-fluoro-3-(trifluoromethyl)phenyl]-2,2-dimethyl-3-oxo-3,4-dihydro-2H-1,4-benzoxazin-7-yl]methanesulfonamide;

N-[4-(3-chloro-4-fluorophenyl)-5-fluoro-2,2-dimethyl-3-oxo-3,4-dihydro-2H-1,4-benzoxazin-7-yl]methanesulfonamide;

N-[4-(3,4-difluorophenyl)-5-fluoro-2,2-dimethyl-3-oxo-3,4-dihydro-2H-1,4-benzoxazin-7-yl]methanesulfonamide;

N-[5-fluoro-4-(5-fluoro-6-methylpyridin-2-yl)-2,2-dimethyl-3-oxo-3,4-dihydro-2H-1,4-benzoxazin-7-yl]methanesulfonamide;

N-[4-(6-chloro-2-methylpyridin-3-yl)-5-fluoro-2,2-dimethyl-3-oxo-3,4-dihydro-2H-1,4-benzoxazin-7-yl]methanesulfonamide;

N-[4-(4-chloro-2-fluorophenyl)-5-fluoro-2,2-dimethyl-3-oxo-3,4-dihydro-2H-1,4-benzoxazin-7-yl]methanesulfonamide;

N-[4-(5-fluoro-6-methylpyridin-2-yl)-2,2-dimethyl-3-oxo-3,4-dihydro-2H-1,4-benzoxazin-7-yl]methanesulfonamide;

N-[4-(benzothien-2-yl)-2,2-dimethyl-3-oxo-3,4-dihydro-2H-1,4-benzoxazin-7-yl]methanesulfonamide;

N-[4-(benzofuran-2-yl)-2,2-dimethyl-3-oxo-3,4-dihydro-2H-1,4-benzoxazin-7-yl]methanesulfonamide;

N-[4-[2-chloro-6-(trifluoromethyl)pyridin-3-yl]-2,2-dimethyl-3-oxo-3,4-dihydro-2H-1,4-benzoxazin-7-yl]methanesulfonamide;

N-[4-(4-fluorophenyl)-5-(methoxymethyl)-2,2-dimethyl-3-oxo-3,4-dihydro-2H-1,4-benzoxazin-7-yl]methanesulfonamide;

N-[2,2-dimethyl-4-[3-methyl-5-(trifluoromethyl)pyridin-2-yl]-3-oxo-3,4-dihydro-2H-1,4-benzoxazin-7-yl]methanesulfonamide;

N-[2,2-dimethyl-4-[2-methyl-6-(trifluoromethyl)pyridin-3-yl]-3-oxo-3,4-dihydro-2H-1,4-benzoxazin-7-yl]methanesulfonamide;

N-[2,2-dimethyl-4-[2-methyl-5-(trifluoromethyl)pyridin-3-yl]-3-oxo-3,4-dihydro-2H-1,4-benzoxazin-7-yl]methanesulfonamide;

N-[5-ethyl-4-(4-fluorophenyl)-2,2-dimethyl-3-oxo-3,4-dihydro-2H-1,4-benzoxazin-7-yl]methanesulfonamide;

N-[5-fluoro-2,2-dimethyl-3-oxo-4-[5-(trifluoromethyl)-2-thienyl]-3,4-dihydro-2H-1,4-benzoxazin-7-yl]methanesulfonamide;

N-[5-fluoro-4-(5-fluoro-3-methylpyridin-2-yl)-2,2-dimethyl-3-oxo-3,4-dihydro-2H-1,4-benzoxazin-7-yl]methanesulfonamide;

N-[4-(6-chloro-2,2-difluoro-1,3-benzodioxol-5-yl)-5-fluoro-2,2-dimethyl-3-oxo-3,4-dihydro-2H-1,4-benzoxazin-7-yl]methanesulfonamide;

N-[4-(2,2-difluoro-1,3-benzodioxol-5-yl)-5-fluoro-2,2-dimethyl-3-oxo-3,4-dihydro-2H-1,4-benzoxazin-7-yl]methanesulfonamide;

N-[4-(5-bromo-3-methylpyridin-2-yl)-5-fluoro-2,2-dimethyl-3-oxo-3,4-dihydro-2H-1,4-benzoxazin-7-yl]methanesulfonamide;

N-[5-fluoro-2,2-dimethyl-4-(3-methyl-5-(trifluoromethyl)pyridin-2-yl]-3-oxo-3,4-dihydro-2H-1,4-benzoxazin-7-yl]methanesulfonamide;

N-[4-(4-chloro-2-methylphenyl)-5-fluoro-2,2-dimethyl-3-oxo-3,4-dihydro-2H-1,4-benzoxazin-7-yl]methanesulfonamide;

N-[4-(3-amino-4-fluorophenyl)-2,2-dimethyl-3-oxo-3,4-dihydro-2H-1,4-benzoxazin-7-yl]methanesulfonamide;

N-[4-(4-fluoro-2-methoxyphenyl)-2,2-dimethyl-3-oxo-3,4-dihydro-2H-1,4-benzoxazin-7-yl]methanesulfonamide;

4-(3-chloro-4-fluorophenyl)-N,2,2-trimethyl-3-oxo-3,4-dihydro-2H-1,4-benzoxazine-7-sulfonamide;

N-{2,2-dimethyl-3-oxo-4-[3-(trifluoromethyl)phenyl]-3,4-dihydro-2H-1,4-benzoxazin-7-yl}methanesulfonamide; and N-{2,2-dimethyl-4-[2-methyl-3-(trifluoromethyl)phenyl]-3-oxo-3,4-dihydro-2H -1,4-benzoxazin-7-yl}methanesulfonamide;

or a pharmaceutically acceptable salt thereof.

10. A pharmaceutical composition comprising as an active ingredient a compound of the following formula [I]:

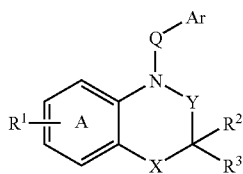

[I]

wherein
Ring A is a benzene ring optionally substituted by one to three group(s) selected from (a) a halogen atom, (b) a $C_{1-6}$ alkyl group, said alkyl group being optionally substituted by one to three group(s) selected from a halogen atom, a hydroxyl group, and a $C_{1-6}$ alkoxy group, (c) a hydroxyl group, (d) a $C_{1-6}$ alkoxy group, (e) an amino group, (f) a cyano group, (g) a $C_{2-12}$ alkenyl group, (h) a $C_{1-7}$ alkanoyl group, and (j) a $C_{3-10}$ cycloalkyl group, $R^1$ is located at the 7-position of the 1,4-benzoxazine moiety and is a group of the formula: $R^aSO_2NH$—, $R^aSO_2NH$—$CH_2$— or $(R^b)(R^c)NSO_2$—, wherein $R^a$ is a $C_{1-6}$ alkyl group, a $C_{3-10}$ cycloalkyl group, an amino group optionally substituted by one or two $C_{1-6}$ alkyl group(s), a 6- to 10-membered monocyclic or bicyclic aryl group, or a 5- to 10-membered monocyclic or bicyclic heteroaryl group containing one to two heteroatom(s) selected from an oxygen atom, a sulfur atom, and a nitrogen atom, $R^b$ and $R^c$ are the same or different and are each a hydrogen atom, a $C_{1-6}$ alkyl group, or a $C_{3-10}$ cycloalkyl group, one of $R^2$ and $R^3$ is a hydrogen atom, a halogen atom, or a $C_{1-6}$ alkyl group, and the other is a hydrogen atom, a $C_{1-6}$ alkyl group, a $C_{1-6}$ alkoxycarbonyl group, or a phenyl group, or both $R^2$ and $R^3$ combine each other together with the adjacent carbon atom to form a $C_{3-10}$ cycloalkyl group, X is an oxygen atom, Y is a group of the formula: —C(=O)—, —C(=S)—, or —CH($R^5$)—, wherein $R^5$ is a hydrogen atom or a phenyl group, Ar is a 6- to 10-membered monocyclic or bicyclic aryl group or a 5- to 10-membered monocyclic or bicyclic heteroaryl group containing one to two heteroatom(s) selected from an oxygen atom, a sulfur atom, and a nitrogen atom, and said aryl or heteroaryl group is optionally substituted by one to three group(s) selected from (a) a halogen atom, (b) a hydroxyl group, (c) a cyano group, (d) a $C_{1-6}$ alkyl group optionally substituted by one to three halogen atom(s), (e) a hydroxyl-$C_{1-6}$ alkyl group, (f) a benzoyloxymethyl group, (g) a $C_{1-6}$ alkoxy group optionally substituted by one to three halogen atom(s), (h) a $C_{1-6}$ alkoxycarbonyl-$C_{1-6}$ alkoxy group, (i) a $C_{1-6}$ alkylthio group, (j) a $C_{1-6}$ alkylenedioxy group optionally substituted by one to two halogen atom(s), (k) an amino group optionally substituted by one to two $C_{1-6}$ alkyl group(s), (l) an acylamino group, said acyl group being a $C_{1-6}$ alkanoyl group or a benzoyl group, (m) $C_{3-10}$ cycloalkyl group, and (n) a $C_{1-6}$ alkylsulfonyl group, and Q is a single bond, a $C_{1-6}$ alkylene group or a $C_{1-6}$ alkenylene group, or a pharmaceutically acceptable salt thereof, and a pharmaceutically acceptable carrier therefor.

11. A pharmaceutical composition comprising as an active ingredient a compound of the following formula [I-a]:

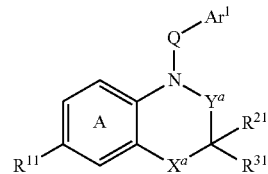

[I-a]

wherein
Ring A is a benzene ring optionally substituted by one to three group(s) selected from (a) a halogen atom, (b) a $C_{1-6}$ alkyl group, said alkyl group being optionally substituted by one to three group(s) selected from a halogen atom, a hydroxyl group, and a $C_{1-6}$ alkoxy group, (c) a hydroxyl group, (d) a $C_{1-6}$ alkoxy group, (e) an amino group, (i) a $C_{2-12}$ alkenyl group, (j) a $C_{1-7}$ alkanoyl group, and (k) a $C_{3-10}$ cycloalkyl group, $R^{11}$ is a group of the formula: $R^{aa}SO_2NH$—, $R^{aa}SO_2NH$—$CH_2$— or $(R^b)(R^c)NSO_2$—, wherein $R^a$ is a $C_{1-6}$ alkyl group, a $C_{3-10}$ cycloalkyl group, an amino group optionally substituted by one or two $C_{1-6}$ alkyl group(s), a phenyl group, or a 5- to 6-membered monocyclic heteroaryl group containing one to two heteroatom(s) selected from an oxygen atom, a sulfur atom, and a nitrogen atom, $R^b$ and $R^c$ are the same or different and are each a hydrogen atom, a $C_{1-6}$ alkyl group, or a $C_{3-10}$ cycloalkyl group, one of $R^{21}$ and $R^{31}$ is a hydrogen atom, a halogen atom or a $C_{1-6}$ alkyl group, and another is a hydrogen atom, a $C_{1-6}$ alkyl group, a $C_{1-6}$ alkoxycarbonyl group, or a phenyl group, or both of them combine each other together with the adjacent carbon atom to form a $C_{3-8}$ cycloalkyl group, $X^a$ is an oxygen atom, $Y^a$ is a group of the formula: —C(=O)—, —C(=S)— or —CH($R^{51}$)—, wherein $R^{51}$ is a hydrogen atom or a phenyl group, $Ar^j$ is
(a) a phenyl group optionally substituted by one to three group(s) selected from a halogen atom, a hydroxyl group, a cyano group, a nitro group, a $C_{1-6}$ alkyl group optionally substituted by one to three halogen atom(s), a hydroxy-$C_{1-6}$ alkyl group, a benzoyloxymethyl group, a $C_{1-6}$ alkoxy group optionally substituted by one to three halogen atom(s), a $C_{1-6}$ alkoxycarbonyl-$C_{1-6}$alkoxy group, a $C_{1-6}$ alkylthio group, a $C_{1-6}$ alkylenedioxy group optionally substituted by one to two halogen atom(s), an amino group optionally substituted by one or two $C_{1-6}$ alkyl group(s), a $C_{1-7}$ alkanoylamino group, a $C_{1-6}$ alkoxycarbonylamino group, a $C_{3-10}$ cycloalkyl group, and a $C_{1-6}$ alkylsulfonyl group;
(b) a thienyl group optionally substituted by one to two group(s) selected from a halogen atom and a trihalogeno$C_{1-6}$ alkyl group, said thienyl group being optionally fused to a benzene ring;
(c) a pyridyl group optionally substituted by one to two group(s) selected from a halogen atom, a nitro group, a $C_{1-6}$ alkyl group and a trihalogeno$C_{1-6}$ alkyl group;
(d) a pyrimidinyl group optionally substituted by a halogen atom;
(e) a quinolyl group;
(f) a pyridazinyl group optionally substituted by a halogen atom;
(g) a pyrrolyl group;
(h) a furyl group optionally fused to a benzene ring;
(i) a thiazolyl group optionally fused to a benzene ring;
(j) an imidazolyl group optionally fused to a benzene ring and optionally substituted by a $C_{1-6}$ alkyl group; or
(k) a naphthyl group, and Q is a single bond, a $C_{1-6}$ alkylene group, or a $C_{1-6}$ alkenylene group,
or a pharmaceutically acceptable salt thereof, and
a pharmaceutically acceptable carrier therefor.

12. The pharmaceutical composition according to claim 11 which is an agent for prevention and/or treatment of cardiovascular diseases including hypertension, heart failure, cardiac infarction, angina pectoris, cardiac hypertrophy, cardiomyositis, cardiac/vascular fibrosis, baroreceptor dysfunction, excessive body fluid and arrhythmia, or endocrine diseases including primary/secondary aldosteronism, Addisson's disease, Cushing's syndrome, and Bartter's syndrome.

13. A compound of the following formula [ii]:

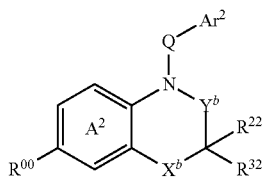

[ii]

wherein Ring $A^2$ is a benzene ring optionally substituted by one to two group(s) selected from a halogen atom and a $C_{1-6}$ alkoxy group, $R^{00}$ is a nitro group or an amino group, one of $R^{22}$ and $R^{32}$ is a hydrogen atom or a $C_{1-6}$ alkyl group and another is a $C_{1-6}$ alkyl group, a phenyl group or a halogenophenyl group, $X^b$ is an oxygen atom, $Y^b$ is a group of the formula: —C(=O)— or —CH($R^{52}$)—, wherein $R^{52}$ is a hydrogen atom or a phenyl group, $Ar^2$ is a phenyl group optionally substituted by one to three group(s) selected from a halogen atom, a cyano group, a $C_{1-6}$ alkyl group, a trihalogeno$C_{1-6}$ alkyl group and a $C_{1-6}$ alkylenedioxy group optionally substituted by one to two halogen atom(s) or a pyridyl group optionally substituted by one to two group(s) selected from a halogen atom and a $C_{1-6}$ alkyl group and Q is a single bond, a $C_{1-6}$ alkylene group or a $C_{1-6}$ alkenylene group, or a pharmaceutically acceptable salt thereof.

14. A pharmaceutical composition comprising as an active ingredient a compound of the following formula [ii]:

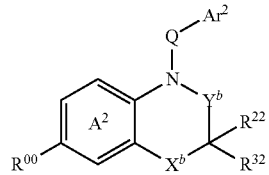

[ii]

wherein Ring $A^2$ is a benzene ring optionally substituted by one to two group(s) selected from a halogen atom and a $C_{1-6}$ alkoxy group, $R^{00}$ is a nitro group or an amino group, one of $R^{22}$ and $R^{32}$ is a hydrogen atom or a $C_{1-6}$ alkyl group and another is a $C_{1-6}$ alkyl group, a phenyl group or a halogenophenyl group, $X^b$ is an oxygen atom, $Y^b$ is a group of the formula: —C(=O)— or —CH($R^{52}$)—, wherein $R^{52}$ is a hydrogen atom or a phenyl group, $Ar^2$ is a phenyl group optionally substituted by one to three group(s) selected from a halogen atom, a cyano group, a $C_{1-6}$ alkyl group, a trihalogeno$C_{1-6}$ alkyl group and a $C_{1-6}$ alkylenedioxy group optionally substituted by one to two halogen atom(s) or a pyridyl group optionally substituted by one to two group(s) selected from a halogen atom and a $C_{1-6}$ alkyl group and Q is a single bond, a $C_{1-6}$ alkylene group or a $C_{1-6}$ alkenylene group, or a pharmaceutically acceptable salt thereof, and
a pharmaceutically acceptable carrier therefor.

15. The compound of claim 9 which is
N-[4-(4-fluoro-3-methylphenyl)-2,2-dimethyl-3-oxo-3,4-dihydro-2H-1,4-benzoxazin-7-yl]methanesulfonamide,
or a pharmaceutically acceptable salt thereof.

16. The compound of claim 9 which is
N-(2,2-dimethyl-3-oxo-4-phenyl-3,4-dihydro-2H-1,4-benzoxazin-7-yl)methanesulfonamide,
or a pharmaceutically acceptable salt thereof.

17. The compound of claim 9 which is
N-[4-(4-fluorophenyl)-2,2-dimethyl-3-oxo-3,4-dihydro-2H-1,4-benzoxazin-7-yl]methanesulfonamide,
or a pharmaceutically acceptable salt thereof.

18. The compound of claim 9 which is
N-[6-chloro-4-(4-fluorophenyl)-2,2-dimethyl-3-oxo-3,4-dihydro-2H-1,4-benzoxazin-7-yl]methanesulfonamide,
or a pharmaceutically acceptable salt thereof.

19. The pharmaceutical composition according to claim 11 which is
N-[4-(4-fluoro-3-methylphenyl)-2,2-dimethyl-3-oxo-3,4-dihydro-2H-1,4-benzoxazin-7-yl]methanesulfonamide,
or a pharmaceutically acceptable salt thereof.

20. The pharmaceutical composition according to claim 11 which is
N-(2,2-dimethyl-3-oxo-4-phenyl-3,4-dihydro-2H-1,4-benzoxazin-7-yl)methanesulfonamide,
or a pharmaceutically acceptable salt thereof.

21. The pharmaceutical composition according to claim 11 which is
N-[4-(4-fluorophenyl)-2,2-dimethyl-3-oxo-3,4-dihydro-2H-1,4-benzoxazin-7-yl]methanesulfonamide,
or a pharmaceutically acceptable salt thereof.

22. The pharmaceutical composition according to claim 11 which is
N-[6-chloro-4-(4-fluorophenyl)-2,2-dimethyl-3-oxo-3,4-dihydro-2H-1,4-benzoxazin-7-yl]methanesulfonamide,
or a pharmaceutically acceptable salt thereof.

* * * * *